(12) United States Patent
Eigler et al.

(10) Patent No.: US 11,458,287 B2
(45) Date of Patent: *Oct. 4, 2022

(54) DEVICES WITH DIMENSIONS THAT CAN BE REDUCED AND INCREASED IN VIVO, AND METHODS OF MAKING AND USING THE SAME

(71) Applicant: V-Wave Ltd., Caesarea (IL)

(72) Inventors: Neal Eigler, Agoura Hills, CA (US); Nir Nae, Binyamina (IL); Nathan Bukhdruker, Haifa (IL); James S. Whiting, Los Angeles, CA (US); Lior Rosen, Or Akiva (IL); Erez Rozenfeld, Shoham (IL); Werner Hafelfinger, Thousand Oaks, CA (US); Tamir Ben-David, Tel Aviv (IL)

(73) Assignee: V-Wave Ltd., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/660,384

(22) Filed: Apr. 22, 2022

(65) Prior Publication Data
US 2022/0241565 A1    Aug. 4, 2022

Related U.S. Application Data

(63) Continuation of application No. 17/092,081, filed on Nov. 6, 2020, which is a continuation of application
(Continued)

(51) Int. Cl.
*A61F 2/90* (2013.01)
*A61M 27/00* (2006.01)
*A61F 2/95* (2013.01)

(52) U.S. Cl.
CPC ............. *A61M 27/002* (2013.01); *A61F 2/90* (2013.01); *A61F 2/95* (2013.01);
(Continued)

(58) Field of Classification Search
CPC ...... A61F 2/90; A61F 2/95; A61F 2210/0023; A61F 2230/0069; A61F 2230/0078;
(Continued)

(56) References Cited

U.S. PATENT DOCUMENTS 3,852,334 A    12/1974    Dusza et al.
3,874,388 A    4/1975     King et al.
(Continued)

FOREIGN PATENT DOCUMENTS

AU    2003291117 B2    4/2009
CA    2378920 A1       2/2001
(Continued)

OTHER PUBLICATIONS

Abraham et al., "Hemodynamic Monitoring in Advanced Heart Failure: Results from the LAPTOP-HF Trial," J Card Failure, 22:940 (2016) (Abstract Only).
(Continued)

*Primary Examiner* — Suzette J Gherbi
(74) *Attorney, Agent, or Firm* — Eversheds Sutherland (US) LLP; Christopher C. Bolten; Nicola A. Pisano

(57) ABSTRACT

Devices are provided with an internal dimension that can be reduced and increased in vivo. In one example, an interatrial shunt for placement at an atrial septum of a patient's heart includes a body. The body includes first and second regions coupled in fluid communication by a neck region. The body includes a shape-memory material. The body defines a passageway through the neck region for blood to flow between a first atrium and a second atrium. The first and second regions are superelastic at body temperature, and the neck region is malleable at body temperature. A flow area of the passageway through the neck region may be adjusted in vivo.

29 Claims, 31 Drawing Sheets

Related U.S. Application Data

No. 16/875,652, filed on May 15, 2020, now Pat. No. 10,898,698, application No. 17/660,384, which is a continuation-in-part of application No. 16/963,139, filed as application No. PCT/IB2019/050452 on Jan. 19, 2019, application No. 17/660,384, filed on Apr. 22, 2022, which is a continuation-in-part of application No. PCT/IB2021/053594, filed on Apr. 29, 2021, which is a continuation-in-part of application No. 17/092,081, filed on Nov. 6, 2020, which is a continuation of application No. 16/875,652, filed on May 15, 2020, now Pat. No. 10,898,698.

(60) Provisional application No. 63/019,777, filed on May 4, 2020, provisional application No. 62/619,748, filed on Jan. 20, 2018.

(52) U.S. Cl.
CPC ............ *A61F 2210/0023* (2013.01); *A61F 2230/0069* (2013.01); *A61F 2230/0078* (2013.01); *A61F 2250/001* (2013.01); *A61F 2250/0039* (2013.01); *A61M 2205/0266* (2013.01); *A61M 2210/125* (2013.01)

(58) Field of Classification Search
CPC ...... A61F 2250/001; A61F 2250/0039; A61M 27/002; A61M 2205/0266; A61M 2210/125
USPC .................................................. 623/1.15–2.1
See application file for complete search history.

(56) References Cited

U.S. PATENT DOCUMENTS

| | | |
|---|---|---|
| 3,952,334 A | 4/1976 | Bokros et al. |
| 4,484,955 A | 11/1984 | Hochstein |
| 4,601,309 A | 7/1986 | Chang |
| 4,617,932 A | 10/1986 | Kornberg |
| 4,662,355 A | 5/1987 | Pieronne et al. |
| 4,665,906 A | 5/1987 | Jervis |
| 4,705,507 A | 11/1987 | Boyles |
| 4,836,204 A | 6/1989 | Landymore et al. |
| 4,979,955 A | 12/1990 | Smith |
| 4,988,339 A | 1/1991 | Vadher |
| 4,995,857 A | 2/1991 | Arnold |
| 5,035,702 A | 7/1991 | Taheri |
| 5,035,706 A | 7/1991 | Giantureo et al. |
| 5,037,427 A | 8/1991 | Harada et al. |
| 5,089,005 A | 2/1992 | Harada |
| 5,186,431 A | 2/1993 | Tamari |
| 5,197,978 A | 3/1993 | Hess |
| 5,234,447 A | 8/1993 | Kaster et al. |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,378,239 A | 1/1995 | Termin et al. |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,545,210 A | 8/1996 | Hess et al. |
| 5,556,386 A | 9/1996 | Todd |
| 5,578,008 A | 11/1996 | Hara |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,324 A | 4/1998 | Glastra |
| 5,749,880 A | 5/1998 | Banas et al. |
| 5,779,716 A | 7/1998 | Cano et al. |
| 5,795,307 A | 8/1998 | Krueger |
| 5,810,836 A | 9/1998 | Hussein et al. |
| 5,824,062 A | 10/1998 | Patke et al. |
| 5,824,071 A | 10/1998 | Nelson et al. |
| 5,846,261 A | 12/1998 | Kotula et al. |
| 5,910,144 A | 6/1999 | Hayashi |
| 5,916,193 A | 6/1999 | Stevens et al. |
| 5,941,850 A | 8/1999 | Shah et al. |
| 5,957,949 A | 9/1999 | Leonhardt et al. |
| 5,990,379 A | 11/1999 | Gregory |
| 6,027,518 A | 2/2000 | Gaber |
| 6,039,755 A | 3/2000 | Edwin et al. |
| 6,039,759 A | 3/2000 | Carpentier et al. |
| 6,086,610 A | 7/2000 | Duerig et al. |
| 6,111,520 A | 8/2000 | Allen et al. |
| 6,117,159 A | 9/2000 | Huebsch et al. |
| 6,120,534 A | 9/2000 | Ruiz |
| 6,124,523 A | 9/2000 | Banas et al. |
| 6,126,686 A | 10/2000 | Badylak et al. |
| 6,165,188 A | 12/2000 | Saadat et al. |
| 6,210,318 B1 | 4/2001 | Lederman |
| 6,214,039 B1 | 4/2001 | Banas et al. |
| 6,217,541 B1 | 4/2001 | Yu |
| 6,221,096 B1 | 4/2001 | Aiba et al. |
| 6,231,587 B1 | 5/2001 | Makower |
| 6,242,762 B1 | 6/2001 | Brown et al. |
| 6,245,099 B1 | 6/2001 | Edwin et al. |
| 6,254,564 B1 | 7/2001 | Wilk et al. |
| 6,260,552 B1 | 7/2001 | Mortier et al. |
| 6,264,684 B1 | 7/2001 | Banas et al. |
| 6,270,515 B1 | 8/2001 | Linden et al. |
| 6,270,526 B1 | 8/2001 | Cox |
| 6,277,078 B1 | 8/2001 | Porat et al. |
| 6,278,379 B1 | 8/2001 | Allen et al. |
| 6,302,892 B1 | 10/2001 | Wilk |
| 6,306,141 B1 | 10/2001 | Jervis |
| 6,328,699 B1 | 12/2001 | Eigler et al. |
| 6,344,022 B1 | 2/2002 | Jarvik |
| 6,358,277 B1 | 3/2002 | Duran |
| 6,391,036 B1 | 5/2002 | Berg et al. |
| 6,398,803 B1 | 6/2002 | Layne et al. |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,475,136 B1 | 11/2002 | Forsell |
| 6,478,776 B1 | 11/2002 | Rosenman et al. |
| 6,485,507 B1 | 11/2002 | Walak et al. |
| 6,488,702 B1 | 12/2002 | Besselink |
| 6,491,705 B2 | 12/2002 | Gifford, III et al. |
| 6,497,722 B1 * | 12/2002 | Von Oepen ............... A61F 2/07 623/1.13 |
| 6,527,698 B1 | 3/2003 | Kung et al. |
| 6,544,208 B2 | 4/2003 | Ethier et al. |
| 6,547,814 B2 | 4/2003 | Edwin et al. |
| 6,562,066 B1 | 5/2003 | Martin |
| 6,572,652 B2 | 6/2003 | Shaknovich |
| 6,579,314 B1 | 6/2003 | Lombardi et al. |
| 6,589,198 B1 | 7/2003 | Soltanpour et al. |
| 6,616,675 B1 | 9/2003 | Evard et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,719,781 B1 * | 4/2004 | Kim ...................... A61F 2/958 623/1.13 |
| 6,740,115 B2 | 5/2004 | Lombardi et al. |
| 6,758,858 B2 | 7/2004 | McCrea et al. |
| 6,764,507 B2 | 7/2004 | Shanley et al. |
| 6,770,087 B2 | 8/2004 | Layne et al. |
| 6,797,217 B2 | 9/2004 | McCrea et al. |
| 6,890,350 B1 | 5/2005 | Walak |

(56) References Cited

U.S. PATENT DOCUMENTS

| | | |
|---|---|---|
| 6,923,829 B2 | 8/2005 | Boyle et al. |
| 6,970,742 B2 | 11/2005 | Mann et al. |
| 7,001,409 B2 | 2/2006 | Amplatz |
| 7,004,966 B2 | 2/2006 | Edwin et al. |
| 7,025,777 B2 | 4/2006 | Moore |
| 7,060,150 B2 | 6/2006 | Banas et al. |
| 7,083,640 B2 | 8/2006 | Lombardi et al. |
| 7,115,095 B2 | 10/2006 | Eigler et al. |
| 7,118,600 B2 | 10/2006 | Dua et al. |
| 7,137,953 B2 | 11/2006 | Eigler et al. |
| 7,147,604 B1 | 12/2006 | Allen et al. |
| 7,149,587 B2 | 12/2006 | Wardle et al. |
| 7,169,160 B1 | 1/2007 | Middleman et al. |
| 7,169,172 B2 | 1/2007 | Levine et al. |
| 7,195,594 B2 | 3/2007 | Eigler et al. |
| 7,208,010 B2 | 4/2007 | Shanley et al. |
| 7,226,558 B2 | 6/2007 | Nieman et al. |
| 7,245,117 B1 | 7/2007 | Joy et al. |
| 7,294,115 B1 | 11/2007 | Wilk |
| 7,306,756 B2 | 12/2007 | Edwin et al. |
| 7,402,899 B1 | 7/2008 | Whiting et al. |
| 7,439,723 B2 | 10/2008 | Allen et al. |
| 7,468,071 B2 | 12/2008 | Edwin et al. |
| 7,483,743 B2 | 1/2009 | Mann et al. |
| 7,498,799 B2 | 3/2009 | Allen et al. |
| 7,509,169 B2 | 3/2009 | Eigler et al. |
| 7,550,978 B2 | 6/2009 | Joy et al. |
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |
| 7,679,355 B2 | 3/2010 | Allen et al. |
| 7,717,854 B2 | 5/2010 | Mann et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler et al. |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Phan et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,665,086 B2 | 3/2014 | Miller et al. |
| 8,696,611 B2 | 4/2014 | Nitzan et al. |
| 8,790,241 B2 | 7/2014 | Edwin et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 9,005,155 B2 | 4/2015 | Sugimoto |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 | 6/2015 | Gallagher et al. |
| 9,205,236 B2 | 12/2015 | McNamara et al. |
| 9,220,429 B2 | 12/2015 | Nabutovsky et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 * | 9/2018 | Eigler ................ A61F 2/2487 |
| 10,105,103 B2 | 10/2018 | Goldshtein et al. |
| 10,111,741 B2 | 10/2018 | Michalak |
| 10,207,087 B2 | 2/2019 | Keren et al. |
| 10,207,807 B2 | 2/2019 | Moran et al. |
| 10,251,740 B2 * | 4/2019 | Eigler ................ A61F 2/2487 |
| 10,251,750 B2 | 4/2019 | Alexander et al. |
| 10,265,169 B2 | 4/2019 | Desrosiers et al. |
| 10,299,687 B2 | 5/2019 | Nabutovsky et al. |
| 10,357,320 B2 | 7/2019 | Beira |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,548,725 B2 | 2/2020 | Alkhatib et al. |
| 10,561,423 B2 | 2/2020 | Sharma |
| 10,639,459 B2 | 5/2020 | Nitzan et al. |
| 10,744,012 B2 * | 8/2020 | Bonsignore ............ A61F 2/915 |
| 10,828,151 B2 | 11/2020 | Nitzan et al. |
| 10,835,394 B2 * | 11/2020 | Nae ........................ A61F 2/07 |
| 10,898,698 B1 * | 1/2021 | Eigler ................ A61B 17/0057 |
| 10,912,645 B2 | 2/2021 | Rottenberg et al. |
| 10,925,706 B2 * | 2/2021 | Eigler ................ A61M 27/002 |
| 10,940,296 B2 | 3/2021 | Keren |
| 11,109,988 B2 * | 9/2021 | Rosen ..................... A61F 2/07 |
| 11,234,702 B1 * | 2/2022 | Eigler ................ A61B 5/0031 |
| 11,253,353 B2 | 2/2022 | Levi et al. |
| 11,291,807 B2 * | 4/2022 | Eigler ..................... A61F 2/01 |
| 11,304,831 B2 * | 4/2022 | Nae ......................... A61F 2/07 |
| 11,311,375 B2 * | 4/2022 | Li ........................ A61F 2/2418 |
| 2001/0021872 A1 | 9/2001 | Bailey et al. |
| 2002/0120277 A1 | 8/2002 | Hauschild et al. |
| 2002/0165479 A1 | 11/2002 | Wilk |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2002/0183628 A1 | 12/2002 | Reich et al. |
| 2003/0028213 A1 | 2/2003 | Thill et al. |
| 2003/0045902 A1 | 3/2003 | Weadock |
| 2003/0100920 A1 | 5/2003 | Akin et al. |
| 2003/0125798 A1 | 7/2003 | Martin |
| 2003/0136417 A1 | 7/2003 | Fonseca et al. |

(56) References Cited

U.S. PATENT DOCUMENTS

| | | |
|---|---|---|
| 2003/0139819 A1 | 7/2003 | Beer et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2003/0216803 A1 | 11/2003 | Ledergerber |
| 2004/0010219 A1 | 1/2004 | McCusker et al. |
| 2004/0016514 A1 | 1/2004 | Nien |
| 2004/0073242 A1 | 4/2004 | Chanduszko |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0116999 A1 | 6/2004 | Ledergerber |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0147969 A1 | 7/2004 | Mann et al. |
| 2004/0162514 A1 | 8/2004 | Alferness et al. |
| 2004/0193261 A1 | 9/2004 | Berreklouw |
| 2004/0210190 A1 | 10/2004 | Kohler et al. |
| 2004/0210307 A1 | 10/2004 | Khairkhahan |
| 2004/0225352 A1 | 11/2004 | Osborne et al. |
| 2005/0003327 A1 | 1/2005 | Elian et al. |
| 2005/0033327 A1 | 2/2005 | Gainor et al. |
| 2005/0033351 A1 | 2/2005 | Newton |
| 2005/0065589 A1 | 3/2005 | Schneider et al. |
| 2005/0125032 A1 | 6/2005 | Whisenant et al. |
| 2005/0137682 A1 | 6/2005 | Justino |
| 2005/0148925 A1 | 7/2005 | Rottenberg et al. |
| 2005/0165344 A1 | 7/2005 | Dobak, III |
| 2005/0182486 A1 | 8/2005 | Gabbay |
| 2005/0267524 A1 | 12/2005 | Chanduszko |
| 2005/0283231 A1 | 12/2005 | Haug et al. |
| 2005/0288596 A1 | 12/2005 | Eigler et al. |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0025857 A1 | 2/2006 | Bergheim et al. |
| 2006/0111660 A1 | 5/2006 | Wolf et al. |
| 2006/0116710 A1 | 6/2006 | Corcoran et al. |
| 2006/0122522 A1 | 6/2006 | Chavan et al. |
| 2006/0122647 A1 | 6/2006 | Callaghan et al. |
| 2006/0167541 A1 | 7/2006 | Lattouf |
| 2006/0184231 A1 | 8/2006 | Rucker |
| 2006/0212110 A1 | 9/2006 | Osborne et al. |
| 2006/0241745 A1 | 10/2006 | Solem |
| 2006/0256611 A1 | 11/2006 | Bednorz et al. |
| 2006/0282157 A1 | 12/2006 | Hill et al. |
| 2007/0010852 A1 | 1/2007 | Blaeser et al. |
| 2007/0021739 A1 | 1/2007 | Weber |
| 2007/0043435 A1 | 2/2007 | Seguin et al. |
| 2007/0129756 A1 | 6/2007 | Abbott et al. |
| 2007/0191863 A1 | 8/2007 | De Juan et al. |
| 2007/0213813 A1 | 9/2007 | Von Segesser et al. |
| 2007/0276413 A1 | 11/2007 | Nobles |
| 2007/0276414 A1 | 11/2007 | Nobles |
| 2007/0282157 A1 | 12/2007 | Rottenberg et al. |
| 2007/0299384 A1 | 12/2007 | Faul et al. |
| 2008/0034836 A1 | 2/2008 | Eigler et al. |
| 2008/0086205 A1 | 4/2008 | Gordy et al. |
| 2008/0125861 A1 | 5/2008 | Webler et al. |
| 2008/0177300 A1 | 7/2008 | Mas et al. |
| 2008/0262602 A1 | 10/2008 | Wilk et al. |
| 2008/0319525 A1 | 12/2008 | Tieu et al. |
| 2009/0030499 A1 | 1/2009 | Bebb et al. |
| 2009/0054976 A1 | 2/2009 | Tuval et al. |
| 2009/0125104 A1 | 5/2009 | Hoffman |
| 2009/0149947 A1 | 6/2009 | Frohwitter |
| 2009/0198315 A1 | 8/2009 | Boudjemline |
| 2009/0276040 A1 | 11/2009 | Rowe et al. |
| 2009/0319037 A1 | 12/2009 | Rowe et al. |
| 2010/0004740 A1 | 1/2010 | Seguin et al. |
| 2010/0022940 A1 | 1/2010 | Thompson |
| 2010/0057192 A1 | 3/2010 | Celermajer |
| 2010/0069836 A1 | 3/2010 | Satake |
| 2010/0070022 A1 | 3/2010 | Kuehling |
| 2010/0081867 A1 | 4/2010 | Fishler et al. |
| 2010/0100167 A1 | 4/2010 | Bortlein et al. |
| 2010/0121434 A1 | 5/2010 | Paul et al. |
| 2010/0179590 A1 | 7/2010 | Fortson et al. |
| 2010/0191326 A1 | 7/2010 | Alkhatib |
| 2010/0249909 A1 | 9/2010 | McNamara et al. |
| 2010/0249910 A1 | 9/2010 | McNamara et al. |
| 2010/0249915 A1 | 9/2010 | Zhang |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324652 A1 | 12/2010 | Aurilia et al. |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1 | 4/2011 | Fischell et al. |
| 2011/0112632 A1* | 5/2011 | Chau ............... A61F 2/2418 623/2.11 |
| 2011/0152923 A1 | 6/2011 | Fox |
| 2011/0190874 A1 | 8/2011 | Celermajer et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0257723 A1 | 10/2011 | McNamara |
| 2011/0264203 A1 | 10/2011 | Dwork et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0319806 A1 | 12/2011 | Wardle |
| 2012/0022507 A1 | 1/2012 | Najafi et al. |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | Von Oepen et al. |
| 2012/0053686 A1 | 3/2012 | McNamara et al. |
| 2012/0071918 A1 | 3/2012 | Amin et al. |
| 2012/0130301 A1 | 5/2012 | McNamara et al. |
| 2012/0165928 A1 | 6/2012 | Nitzan et al. |
| 2012/0179172 A1 | 7/2012 | Paul, Jr. et al. |
| 2012/0190991 A1 | 7/2012 | Bornzin et al. |
| 2012/0265296 A1 | 10/2012 | McNamara et al. |
| 2012/0271398 A1 | 10/2012 | Essinger et al. |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0046373 A1 | 2/2013 | Cartledge et al. |
| 2013/0138145 A1 | 5/2013 | Von Oepen |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |
| 2013/0261531 A1 | 10/2013 | Gallagher et al. |
| 2013/0281988 A1 | 10/2013 | Magnin et al. |
| 2013/0304192 A1 | 11/2013 | Chanduszko |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry, III et al. |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |

(56) References Cited

U.S. PATENT DOCUMENTS

| | | |
|---|---|---|
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2015/0005810 A1 | 1/2015 | Center et al. |
| 2015/0034217 A1 | 2/2015 | Vad |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0112383 A1 | 4/2015 | Sherman et al. |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | McNamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2015/0313599 A1 | 11/2015 | Johnson et al. |
| 2015/0359556 A1 | 12/2015 | Vardi |
| 2016/0007924 A1 | 1/2016 | Eigler et al. |
| 2016/0022423 A1 | 1/2016 | McNamara et al. |
| 2016/0022970 A1 | 1/2016 | Forcucci et al. |
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0157862 A1 | 6/2016 | Hernandez et al. |
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0035435 A1 | 2/2017 | Amin et al. |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165532 A1 | 6/2017 | Khan et al. |
| 2017/0216025 A1 | 8/2017 | Nitzan et al. |
| 2017/0224323 A1 | 8/2017 | Rowe et al. |
| 2017/0224444 A1 | 8/2017 | Viecilli et al. |
| 2017/0231766 A1 | 8/2017 | Hariton et al. |
| 2017/0273790 A1 | 9/2017 | Vettukattil et al. |
| 2017/0281339 A1 | 10/2017 | Levi et al. |
| 2017/0312486 A1 | 11/2017 | Nitzan et al. |
| 2017/0319823 A1 | 11/2017 | Yacoby et al. |
| 2017/0325956 A1 | 11/2017 | Rottenberg et al. |
| 2017/0340460 A1* | 11/2017 | Rosen ..................... A61F 2/844 |
| 2017/0348100 A1 | 12/2017 | Lane et al. |
| 2018/0099128 A9 | 4/2018 | McNamara et al. |
| 2018/0104053 A1 | 4/2018 | Alkhatib et al. |
| 2018/0125630 A1 | 5/2018 | Hynes et al. |
| 2018/0130988 A1 | 5/2018 | Nishikawa et al. |
| 2018/0243071 A1 | 8/2018 | Eigler et al. |
| 2018/0256865 A1 | 9/2018 | Finch et al. |
| 2018/0263766 A1 | 9/2018 | Nitzan et al. |
| 2018/0280667 A1 | 10/2018 | Keren |
| 2018/0344994 A1 | 12/2018 | Karavany et al. |
| 2019/0000327 A1 | 1/2019 | Doan et al. |
| 2019/0008628 A1 | 1/2019 | Eigler et al. |
| 2019/0015103 A1 | 1/2019 | Sharma |
| 2019/0015188 A1 | 1/2019 | Eigler et al. |
| 2019/0021861 A1 | 1/2019 | Finch |
| 2019/0110911 A1 | 4/2019 | Nae et al. |
| 2019/0239754 A1 | 8/2019 | Nabutovsky et al. |
| 2019/0254814 A1 | 8/2019 | Nitzan et al. |
| 2019/0262118 A1 | 8/2019 | Eigler et al. |
| 2019/0328513 A1 | 10/2019 | Levi et al. |
| 2019/0336163 A1 | 11/2019 | McNamara et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |
| 2020/0197178 A1 | 6/2020 | Vecchio |
| 2020/0261705 A1 | 8/2020 | Nitzan et al. |
| 2020/0315599 A1 | 10/2020 | Nae et al. |
| 2020/0368505 A1 | 11/2020 | Nae et al. |
| 2021/0052378 A1 | 2/2021 | Nitzan et al. |
| 2021/0393421 A1* | 12/2021 | Rosen ..................... A61F 2/844 |
| 2022/0015901 A1* | 1/2022 | Dibie ..................... A61F 2/2418 |
| 2022/0054266 A1* | 2/2022 | Kovalsky ............... A61F 2/2418 |
| 2022/0133463 A1* | 5/2022 | Korte ........................ A61F 2/07 |
| | | 623/1.13 |

FOREIGN PATENT DOCUMENTS

| | | |
|---|---|---|
| EP | 1987777 A2 | 11/2008 |
| EP | 2238933 A1 | 10/2010 |
| EP | 2305321 A1 | 4/2011 |
| EP | 1965842 B1 | 11/2011 |
| EP | 3400907 A1 | 11/2018 |
| FR | 2827153 A1 | 1/2003 |
| WO | WO-9531945 A1 | 11/1995 |
| WO | WO-9727898 A1 | 8/1997 |
| WO | WO-9960941 A1 | 12/1999 |
| WO | WO-0044311 A2 | 8/2000 |
| WO | WO-0050100 A1 | 8/2000 |
| WO | WO-0110314 A2 | 2/2001 |
| WO | WO-0226281 A1 | 4/2002 |
| WO | WO-02071974 A2 | 9/2002 |
| WO | WO-02087473 A1 | 11/2002 |
| WO | WO-03053495 A2 | 7/2003 |
| WO | WO-2005027752 A1 | 3/2005 |
| WO | WO-2005074367 A2 | 8/2005 |
| WO | WO-2006127765 A1 | 11/2006 |
| WO | WO-2007083288 A2 | 7/2007 |
| WO | WO-2008055301 A1 | 5/2008 |
| WO | WO-2009029261 A1 | 3/2009 |
| WO | WO-2010128501 A1 | 11/2010 |
| WO | WO-2010129089 A2 | 11/2010 |
| WO | WO-2010139771 A2 | 12/2010 |
| WO | WO-2011062858 A1 | 5/2011 |
| WO | WO-2013096965 A1 | 6/2013 |
| WO | WO-2016178171 A1 | 11/2016 |
| WO | WO-2017118920 A1 | 7/2017 |
| WO | WO-2018158747 A1 | 9/2018 |
| WO | WO-2019015617 A1 | 1/2019 |
| WO | WO-2019085841 A1 | 5/2019 |
| WO | WO-2019109013 A1 | 6/2019 |
| WO | WO-2019142152 A1 | 7/2019 |
| WO | WO-2019179447 A1 | 9/2019 |
| WO | WO-2019218072 A1 | 11/2019 |
| WO | WO-2020206062 A1 | 10/2020 |
| WO | WO-2020257530 A1 | 12/2020 |
| WO | WO-2021050589 A1 | 3/2021 |
| WO | WO-2021113670 A1 | 6/2021 |
| WO | WO-2021212011 A2 | 10/2021 |

(56) References Cited

FOREIGN PATENT DOCUMENTS

| | | |
|---|---|---|
| WO | WO-2022046921 A1 | 3/2022 |
| WO | WO-2022076601 A1 | 4/2022 |

OTHER PUBLICATIONS

Abraham et al., "Sustained efficacy of pulmonary artery pressure to guide adjustment of chronic heart failure therapy: complete follow-up results from the CHAMPION randomised trial," The Lancet, doi.org/10.1016/S0140-6736(15)00723-0 (2015).

Abraham et al., "Wireless pulmonary artery haemodynamic monitoring in chronic heart failure: a randomised controlled trial," The Lancet, DOI:10.1016/S0140-6736(11)60101-3 (2011).

Abreu et al., "Doppler ultrasonography of the femoropopliteal segment in patients with venous ulcer," J Vasc Bras., 11(4):277-285 (2012).

Adamson et al., "Ongoing Right Ventricular Hemodynamics in Heart Failure Clinical Value of Measurements Derived From an Implantable Monitoring System," J Am Coll Cardiol., 41(4):565-571 (2003).

Adamson et al., "Wireless Pulmonary Artery Pressure Monitoring Guides Management to Reduce Decompensation in Heart Failure With Preserved Ejection Fraction," Circ Heart Fail., 7:935-944 (2014).

Ambrosy et al. "The Global Health and Economic Burden of Hospitalizations for Heart Failure," J Am Coll Cardiol., 63:1123-1133 (2014).

Aminde et al., "Current diagnostic and treatment strategies for Lutembacher syndrome: the pivotal role of echocardiography," Cardiovasc Diagn Ther., 5(2):122-132 (2015).

Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).

Anderas et al., "Tilted c-axis Thin-Film Bulk Wave Resonant Pressure Sensors with Improved Sensitivity," IEEE Sensors J., 12(8):2653-2654 (2012).

Ando, et al., Left ventricular decompression through a patent foramen ovale in a patient with hypertrophic cardiomyopathy: A case report, Cardiovascular Ultrasound, 2: 1-7 (2004).

Article 34 Amendments dated May 28, 2013 in Int'l PCT Patent Appl. Serial No. PCT/IB2012/001859 (0810).

Article 34 Amendments dated Nov. 27, 2012 in Int'l PCT Patent Appl. Serial No. PCT/IL2011/000958 (0710).

Ataya et al., "A Review of Targeted Pulmonary Arterial Hypertension-Specific Pharmacotherapy," J. Clin. Med., 5(12):114 (2016).

"Atrium Advanta V12, Balloon Expandable Covered Stent, Improving Patient Outcomes with An Endovascular Approach," Brochure, 8 pages, Getinge (2017).

Bannan et al., "Characteristics of Adult Patients with Atrial Septal Defects Presenting with Paradoxical Embolism.," Catheterization and Cardiovascular Interventions, 74:1066-1069 (2009).

Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).

Beemath et al., "Pulmonary Embolism as a Cause of Death in Adults Who Died With Heart Failure," Am J Cardiol., 98:1073-1075 (2006).

Benza et al., "Monitoring Pulmonary Arterial Hypertension Using an Implantable Hemodynamic Sensor," CHEST, 156(6):1176-1186 (2019).

Boehm, et al., "Balloon Atrial Septostomy: History and Technique," Images Paeditr. Cardiol., 8(1):8-14(2006).

Braunwald, Heart Disease, Chapter 6, pp. 186.

Bridges, et al., "The Society of Thoracic Surgeons Practice Guideline Series: Transmyocardial Laser Revascularization," Ann Thorac Surg., 77:1494-1502 (2004).

Bristow, et al., "Improvement in cardiac myocyte function by biological effects of medical therapy: a new concept in the treatment of heart failure," European Heart Journal, 16 (Suppl.F): 20-31 (1995).

Bruch et al., "Fenestrated Occluders for Treatment of ASD in Elderly Patients with Pulmonary Hypertension and/or Right Heart Failure," J Interven Cardiol., 21(1):44-49 (2008).

Burkhoff et al., "Assessment of systolic and diastolic ventricular properties via pressure-volume analysis: a guide for clinical, translational, and basic researchers," Am J Physiol Heart Circ Physiol., 289:H501-H512 (2005).

Butler et al. "Recognizing Worsening Chronic Heart Failure as an Entity and an End Point in Clinical Trials," JAMA., 312(8):789-790 (2014).

Case, et al., "Relief of High Left-Atrial Pressure in Left-Ventricular Failure," Lancet, (pp. 841-842), Oct. 17, 1964.

Chakko et al., "Clinical, radiographic, and hemodynamic correlations in chronic congestive heart failure: conflicting results may lead to inappropriate care," Am J Medicine, 90:353-359 (1991) (Abstract Only).

Chang et al., "State-of-the-art and recent developments in micro/nanoscale pressure sensors for smart wearable devices and health monitoring systems," Nanotechnology and Precision Engineering, 3:43-52 (2020).

Chen et al., "Continuous wireless pressure monitoring and mapping with ultra-small passive sensors for health monitoring and critical care," Nature Communications, 5(1):1-10 (2014).

Chen et al., "National and Regional Trends in Heart Failure Hospitalization and Mortality Rates for Medicare Beneficiaries, 1998-2008," JAMA, 306(15):1669-1678 (2011).

Chiche et al., "Prevalence of patent foramen ovale and stroke in pulmonary embolism patients," Eur Heart J., 34:P1142 (2013) (Abstract Only).

Chin et al., "The right ventricle in pulmonary hypertension," Coron Artery Dis., 16(1):13-18 (2005) (Abstract Only).

Chun et al., "Lifetime Analysis of Hospitalizations and Survival of Patients Newly Admitted With Heart Failure," Circ Heart Fail., 5:414-421 (2012).

Ciarka et al., "Atrial Septostomy Decreases Sympathetic Overactivity in Pulmonary Arterial Hypertension," Chest, 131 (6):P1831-1837 (2007) (Abstract Only).

Cleland et al., "The EuroHeart Failure survey programme—a survey on the quality of care among patients with heart failure in Europe—Part 1: patient characteristics and diagnosis," Eur Heart J., 24:442-463 (2003).

Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).

Coats, et al., "Controlled Trial of Physical Training in Chronic Heart Failure: Exercise Performance, Hemodynamics, Ventilation, and Autonomic Function," Circulation, 85: 2119-2131 (1992).

Davies et al., "Abnormal left heart function after operation for atrial septal defect," British Heart Journal, 32:747-753 (1970).

Davies, et al., "Reduced Contraction and Altered Frequency Response of Isolated Ventricular Myocytes From Patients With Heart Failure, Circulation," 92: 2540-2549 (1995).

Del Trigo et al., "Unidirectional Left-to-Right Interatrial Shunting for Treatment of Patients with Heart Failure with Reduced Ejection Fraction: a Safety and Proof-of-Principle Cohort Study," Lancet, 387:1290-1297 (2016).

Della Lucia et al., "Design, fabrication and characterization of SAW pressure sensors for offshore oil and gas exploration," Sensors and Actuators A: Physical, 222:322-328 (2015).

Drazner et al., "Prognostic Importance of Elevated Jugular Venous Pressure and a Third Heart Sound in Patients with Heart Failure," N Engl J Med., 345(8):574-81 (2001).

Drazner et al., "Relationship between Right and Left-Sided Filling Pressures in 1000 Patients with Advanced Heart Failure," Heart Lung Transplant, 18:1126-1132 (1999).

Drexel, et al., "The Effects of Cold Work and Heat Treatment on the Properties of Nitinol Wire, Proceedings of the International Con-

(56) References Cited

OTHER PUBLICATIONS ference on Shape Memory and Superelastic Technologies, SMST 2006," Pacific Grove, California, USA (pp. 447-454) May 7-11, 2006.
Eigler et al., "Cardiac Unloading with an Implantable Interatrial Shunt in Heart Failure: Serial Observations in an Ovine Model of Ischemic Cardiomyopathy," Structural Heart, 1:40-48 (2017).
Eigler, et al., Implantation and Recovery of Temporary Metallic Stents in Canine Coronary Arteries, JACC, 22(4):1207-1213 (1993).
Ennezat, et al., An unusual case of low-flow, low gradient severe aortic stenosis: Left-to-right shunt due to atrial septal defect, Cardiology, 113(2):146-148, (2009).
Eshaghian et al., "Relation of Loop Diuretic Dose to Mortality in Advanced Heart Failure," Am J Cardiol., 97:1759-1764 (2006).
Ewert, et al., Acute Left Heart Failure After Interventional Occlusion of an Artial Septal Defect, Z Kardiol, 90(5): 362-366 (May 2001).
Ewert, et al., Masked Left Ventricular Restriction in Elderly Patients With Atrial Septal Defects: A Contraindication for Closure?, Catheterization and Cardiovascular Intervention, 52:177-180 (2001).
Extended European Search Report dated Jan. 8, 2015 in EP Patent Appl No. 10772089.8. (0530).
Extended European Search Report dated Mar. 29, 2019 in EP Patent Appl. Serial No. EP16789391 (1830).
Extended European Search Report dated Sep. 19, 2016 in EP Patent Appl. No. 16170281.6 (0731).
Feldman et al., "Transcatheter Interatrial Shunt Device for the Treatment of Heart Failure with Preserved Ejection Fraction (REDUCE LAP-HF I [Reduce Elevated Left Atrial Pressure in Patients With Heart Failure]), A Phase 2, Randomized, Sham-Controlled Trial," Circulation, 137:364-375 (2018).
Ferrari et al., "Impact of pulmonary arterial hypertension (PAH) on the lives of patients and carers: results from an international survey," Eur Respir J., 42:26312 (2013) (Abstract Only).
Fonarow et al., "Characteristics, Treatments, and Outcomes of Patients With Preserved Systolic Function Hospitalized for Heart Failure," J Am Coll Cardiol., 50(8):768-777 (2007).
Fonarow et al., "Risk Stratification for In-Hospital Mortality in Acutely Decompensated Heart Failure: Classification and Regression Tree Analysis," JAMA, 293(5):572-580 (2005).
Fonarow, G., "The Treatment Targets in Acute Decompensated Heart Failure," Rev Cardiovasc Med., 2:(2):S7-S12 (2001).
Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).
Galie et al., "Pulmonary arterial hypertension: from the kingdom of the near-dead to multiple clinical trial meta-analyses," Eur Heart J., 31:2080-2086 (2010).
Galipeau et al., "Surface acoustic wave microsensors and applications," Smart Materials and Structures, 6(6):658-667 (1997) (Abstract Only).
Geiran, et al., Changes in cardiac dynamics by opening an interventricular shunt in dogs, J. Surg. Res. 48(1):6-12 (1990).
Gelernter-Yaniv, et al., Transcatheter ClosureoOfLeft-to-Right Interatrial Shunts to Resolve Hypoxemia, Congenit. Heart Dis. 31(1): 47-53 (Jan. 2008).
Geva et al., "Atrial septal defects," Lancet, 383:1921-32 (2014).
Gewillig, et al., Creation with a stent of an unrestrictive lasting atrial communication, Cardio. Young 12(4): 404-407 (2002).
Gheorghiade et al., "Acute Heart Failure Syndromes, Current State and Framework for Future Research," Circulation, 112:3958-3968 (2005).
Gheorghiade et al., "Effects of Tolvaptan, a Vasopressin Antagonist, in Patients Hospitalized With Worsening Heart Failure A Randomized Controlled Trial," JAMA., 291:1963-1971 (2004).
Go et al. "Heart Disease and Stroke Statistics—2014 Update—A Report From the American Heart Association," Circulation, 128:1-267 (2014).
Guillevin et al., "Understanding the impact of pulmonary arterial hypertension on patients' and carers' lives," Eur Respir Rev., 22:535-542 (2013).
Guyton et al., "Effect of Elevated Left Atrial Pressure and Decreased Plasma Protein Concentration on the Development of Pulmonary Edema," Circulation Research, 7:643-657 (1959).
Hasenfub, et al., A Transcatheter Intracardiac Shunt Device for Heart Failure with Preserved Ejection Fraction (REDUCE LAP-HF): A Multicentre, Open-Label, Single-Arm, Phase 1 Trial, www.thelancet.com, 387:1298-1304 (2016).
Hoeper et al., "Definitions and Diagnosis of Pulmonary Hypertension," J Am Coll Cardiol., 62(5):D42-D50 (2013).
Hogg et al., "Heart Failure With Preserved Left Ventricular Systolic Function. Epidemiology, Clinical Characteristics, and Prognosis," J Am Coll Cardiol., 43(3):317-327 (2004).
Howell et al., "Congestive heart failure and outpatient risk of venous thromboembolism: A retrospective, case-control study," Journal of Clinical Epidemiology, 54:810-816 (2001).
Huang et al., "Remodeling of the chronic severely failing ischemic sheep heart after coronary microembolization: functional, energetic, structural, and cellular responses," Am J Physiol Heart Circ Physiol., 286:H2141-H2150 (2004).
Humbert et al., "Pulmonary Arterial Hypertension in France—Results from a National Registry," Am J Respir Crit Care Med., 173:1023-1030 (2006).
International Search Report & Written Opinion dated Nov. 7, 2016 in Int'l PCT Patent Appl. Serial No. PCT/IB2016/052561 (1810).
International Search Report & Written Opinion dated May 29, 2018 in Int'l PCT Patent Appl. Serial No. PCT/IB2018/051385 (1310).
International Search Report & Written Opinion dated Feb. 6, 2013 in Int'l PCT Patent Appl. No. PCT/IB2012/001859, 12 pages (0810).
International Search Report & Written Opinion dated Feb. 7, 2020 in Int'l PCT Patent Appl. Serial No. PCT/IB2019/060257 (1410).
International Search Report & Written Opinion dated Feb. 9, 2022 in Int'l PCT Patent Appl. Serial No. PCT/IB2021/060473 (2010).
International Search Report & Written Opinion dated May 13, 2019 in Int'l PCT Patent Appl. No. PCT/IB2019/050452 (1610).
International Search Report & Written Opinion dated May 29, 2018 in Int'l PCT Patent Appl. Serial No. PCTIB2018/051355 (1310).
International Search Report & Written Opinion dated Jul. 14, 2020 in Int'l PCT Patent Appl. Serial No. PCT/IB2020/053832 (1210).
International Search Report & Written Opinion dated Jul. 20, 2020 in Int'l PCT Patent Appl. Serial No. PCT/IB2020/054699 (1710).
International Search Report & Written Opinion dated Jul. 23, 2021 in Int'l PCT Patent Appl. Serial No. PCT/IB2021/053594 (1910).
International Search Report & Written Opinion dated Aug. 12, 2020 in Int'l PCT Patent Appl. Serial No. PCT/IB2020/053118 (1010).
International Search Report & Written Opinion dated Aug. 28, 2012 in Int'l PCT Patent Appl. No. PCT/IL2011/000958 (0710).
International Search Report & Written Opinion dated Sep. 21, 2020 in Int'l PCT Patent Appl. Serial No. PCT/IB2020/054306 (1510).
International Search Report & Written Opinion dated Oct. 11, 2017 in Int'l PCT Patent Appl. Serial No. PCT/IB2017/053188 (1110).
International Search Report & Written Opinion dated Oct. 26, 2007 in Int'l PCT Patent Appl. Serial No. PCT/IB07/50234 (0610).
International Search Report dated Apr. 7, 2008 in Int'l PCT Patent Appl. Serial No. PCT/IL05/00131 (0410).
International Search Report dated Aug. 25, 2010 in Intl PCT Patent Appl. Serial No. PCT/IL2010/000354 (0510).
ISR & Written Opinion dated Feb. 16, 2015 in Int'l PCT Patent Appl. Serial No. PCT/IB2014/001771 (0910).
Jessup et al. "2009Focused Update: ACC/AHA Guidelines for the Diagnosis and Management of Heart Failure in Adults: A Report of the American College of Cardiology Foundation/American Heart Association Task Force on Practice Guidelines: Developed in Collaboration With the International Society for Heart and Lung Transplantation," J. Am. Coll. Cardiol., 53:1343-1382 (2009).
Jiang, G., "Design challenges of implantable pressure monitoring system," Frontiers in Neuroscience, 4(29):1-4 (2010).

(56) References Cited

OTHER PUBLICATIONS

Kane et al., "Integration of clinical and hemodynamic parameters in the prediction of long-term survival in patients with pulmonary arterial hypertension," Chest, 139(6):1285-1293 (2011) (Abstract Only).
Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).
Keogh et al., "Interventional and Surgical Modalities of Treatment in Pulmonary Hypertension," J Am Coll Cardiol., 54:867-77 (2009).
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer, et al., Controlled Trial of Captopril in Chronic Heart Failure: A Rest and Exercise Hemodynamic Study, Circulation, 67(4): 807-816, 1983.
Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
Lai et al., Bidirectional Shunt Through a Residual Atrial Septal Defect After Percutaneous Transvenous Mitral Commissurotomy, Cadiology, 83(3): 205-207 (1993).
Lammers et al., "Efficacy and Long-Term Patency of Fenerstrated Amplatzer Devices in Children," Catheter Cardiovasc Interv., 70:578-584 (2007).
Lemmer, et al., Surgical Implications of Atrial Septal Defect Complicating Aortic Balloon Valvuloplasty, Ann. thorac. Surg, 48(2):295-297 (Aug. 1989).
Lindenfeld et al. "Executive Summary: HFSA 2010 Comprehensive Heart Failure Practice Guideline," J. Cardiac Failure, 16(6):475-539 (2010).
Luo, Yi, *Selective and Regulated RF Heating of Stent Toward Endohyperthermia Treatment of In-Stent Restenosis*, A Thesis Submitted in Partial Fulfillment of The Requirements For The Degree of Master of Applied Science in The Faculty of Graduate and Postdoctoral Studies (Electrical and Computer Engineering), The University of British Columbia, Vancouver, Dec. 2014.
Macdonald et al., "Emboli Enter Penetrating Arteries of Monkey Brain in Relation to Their Size," Stroke, 26:1247-1251 (1995).
Maluli et al., "Atrial Septostomy: A Contemporary Review," Clin. Cardiol., 38(6):395-400 (2015).
Maurer et al., "Rationale and Design of the Left Atrial Pressure Monitoring to Optimize Heart Failure Therapy Study (LAPTOP-HF)," Journal of Cardiac Failure., 21(6): 479-488 (2015).
McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).
McLaughlin et al., "Management of Pulmonary Arterial Hypertension," J Am Coll Cardiol., 65(18):1976-1997 (2015).
McLaughlin et al., "Survival in Primary Pulmonary Hypertension—The Impact of Epoprostenol Therapy.," Circulation, 106:1477-1482 (2002).
Merriam-Webster OnLine Dictionary, Definition of "chamber", printed Dec. 20, 2004.

Mu et al., "Dual mode acoustic wave sensor for precise pressure reading," Applied Physics Letters, 105:113507-1-113507-5 (2014).
Nagaraju et al., "A 400µW Differential FBAR Sensor Interface IC with digital readout," IEEE., pp. 218-221 (2015).
Noordegraaf et al., "The role of the right ventricle in pulmonary arterial hypertension," Eur Respir Rev., 20(122):243-253 (2011).
O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).
Oktay et al., "The Emerging Epidemic of Heart Failure with Preserved Ejection Fraction," Curr Heart Fail Rep., 10(4):1-17 (2013).
Owan et al., "Trends in Prevalence and Outcome of Heart Failure with Preserved Ejection Fraction," N Engl J Med., 355:251-259 (2006).
Paitazoglou et al., "Title: The AFR-Prelieve Trial: A prospective, non-randomized, pilot study to assess the Atrial Flow Regulator (AFR) in Heart Failure Patients with either preserved or reduced ejection fraction," EuroIntervention, 28:2539-50 (2019).
Park Blade Septostomy Catheter Instructions for Use, Cook Medical, 28 pages, Oct. 2015.
Park, et al., Blade Atrial Septostomy: Collaborative Study, Circulation, 66(2):258-266 (1982).
Partial Supplemental European Search Report dated Dec. 11, 2018 in EP Patent Appl. Serial No. 16789391.6 (1830).
Peters et al., "Self-fabricated fenestrated Amplatzer occluders for transcatheter closure of atrial septal defect in patients with left ventricular restriction: midterm results," Clin Res Cardiol., 95:88-92 (2006).
Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi:10.1093/eurheartj/ehw128 (2016).
Potkay, J. A., "Long term, implantable blood pressure monitoring systems," Biomed Microdevices, 10:379-392 (2008).
Pretorious et al., "An Implantable Left Atrial Pressure Sensor Lead Designed for Percutaneous Extraction Using Standard Techniques," PACE, 00:1-8 (2013).
Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).
Rich et al., "Atrial Septostomy as Palliative Therapy for Refractory Primary Pulmonary Hypertension," Am J Cardiol., 51:1560-1561 (1983).
Ritzema et al., "Direct Left Atrial Pressure Monitoring in Ambulatory Heart Failure Patients—Initial Experience With a New Permanent Implantable Device," Circulation, 116:2952-2959 (2007).
Ritzema et al., "Physician-Directed Patient Self-Management of Left Atrial Pressure in Advanced Chronic Heart Failure," Circulation, 121:1086-1095 (2010).
Roberts et al., "Integrated microscopy techniques for comprehensive pathology evaluation of an implantable left atrial pressure sensor," J Histotechnology, 36(1):17-24 (2013).
Rodes-Cabau et al., "Interatrial Shunting for Heart Failure Early and Late Results From the First-in-Human Experience With the V-Wave System," J Am Coll Cardiol Intv., 11:2300-2310.doi:10.1016/j.cin.2018.07.001 (2018).
Rosenquist et al., Atrial Septal Thickness and Area in Normal Heart Specimens and in Those With Ostium Secundum Atrial Septal Defects, J. Clin. Ultrasound, 7:345-348 (1979).
Ross et al., "Interatrial Communication and Left Atrial Hypertension—A Cause of Continuous Murmur," Circulation, 28:853-860 (1963).
Rossignol, et al., Left-to-Right Atrial Shunting: New Hope for Heart Failure, www.thelancet.com, 387:1253-1255 (2016).
Roven, Effect of Compromising Right Ventricular Function in Left Ventricular Failure by Means of Interatrial and Other Shunts 24:209-219 (Aug. 1969).

(56) References Cited

OTHER PUBLICATIONS

Salehian, et al., Improvements in Cardiac Form and Function After Transcatheter Closure of Secundum Atrial Septal Defects, Journal of the American College of Cardiology, 45(4):499-504 (2005).
Sandoval et al., "Effect of atrial septostomy on the survival of patients with severe pulmonary arterial hypertension," Eur Respir J., 38:1343-1348 (2011).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schiff et al., "Decompensated heart failure: symptoms, patterns of onset, and contributing factors," Am J. Med., 114(8):625-630 (2003) (Abstract Only).
Schmitto, et al., Chronic Heart Failure Induced by Multiple Sequential Coronary Microembolization in sheep, The International Journal of Artificial Organs, 31(4):348-353 (2008).
Schneider et al., "Fate of a Modified Fenestration of Atrial Septal Occluder Device after Transcatheter Closure of Atrial Septal Defects in Elderly Patients," J Interven Cardiol., 24:485-490 (2011).
Scholl et al., "Surface Acoustic Wave Devices for Sensor Applications," Phys Status Solidi Appl Res., 185(1):47-58 (2001) (Abstract Only).
Schubert, et al., Left ventricular Conditioning in the Elderly Patient to Prevent Congestive Heart Failure After Transcatheter Closure of the Atrial Septal Defect, Catheterization and Cardiovascular Interventions, 64(3): 333-337 (2005).
Setoguchi et al., "Repeated hospitalizations predict mortality in the community population with heart failure," Am Heart J., 154:260-266 (2007).
Shah et al., "Heart Failure With Preserved, Borderline, and Reduced Ejection Fraction—5-Year Outcomes," J Am Coll Cardiol., https://doi.org/10.1016/j.jacc.2017.08.074 (2017).
Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (REDUCE LAP-HF I) Trial—A Randomized Clinical Trial," JAMA Cardiol. doi:10.1001/jamacardio.2018.2936 (2018).
Sitbon et al., "Selexipag for the Treatment of Pulmonary Arterial Hypertension.," N Engl J Med., 373(26):2522-2533 (2015).
Sitbon et al., "Epoprostenol and pulmonary arterial hypertension: 20 years of clinical experience," Eur Respir Rev., 26:160055:1-14 (2017).
Steimle et al., "Sustained Hemodynamic Efficacy of Therapy Tailored to Reduce Filling Pressures in Survivors With Advanced Heart Failure," Circulation, 96:1165-1172 (1997).
Stevenson et al., "The Limited Reliability of Physical Signs for Estimating Hemodynamics in Chronic Heart Failure," JAMA, 261(6):884-888 (1989) (Abstract Only).
Stormer, et al., Comparative Study of in Vitro Flow Characteristics Between a Human Aortic Valve and a Designed Aortic Valve and Six Corresponding Types of Prosthetic Heart Valves, European Surgical Research 8(2):117-131 (1976).
Stumper, et al., Modified Technique of Stent Fenestration of the Atrial Septum, Heart, 89:1227-1230, (2003).
Su et al., "A film bulk acoustic resonator pressure sensor based on lateral field excitation," International Journal of Distributed Sensor Networks, 14(11):1-8 (2018).
Supplementary European Search Report dated Nov. 13, 2009 in EP Patent Appl. Serial No. 05703174.2 (0430).
Thenappan et al., "Evolving Epidemiology of Pulmonary Arterial Hypertension," Am J Resp Critical Care Med., 186:707-709 (2012).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Torbicki et al., "Atrial Septostomy," The Right Heart, 305-316 (2014).
Trainor, et al., Comparative Pathology of an Implantable Left Atrial Pressure Sensor, ASAIO Journal, Clinical Cardiovascular/Cardiopulmonary Bypass, 59(5):486-492 (2013).
Troost et al., "A Modified Technique of Stent Fenestration of the Interatrial Septum Improves Patients With Pulmonary Hypertension," Catheterization and Cardiovascular Interventions, 73:173179 (2009).
Troughton et al., "Direct Left Atrial Pressure Monitoring in Severe Heart Failure: Long-Term Sensor Performance," J. of Cardiovasc. Trans. Res., 4:3-13 (2011).
Vank-Noordegraaf et al., "Right Heart Adaptation to Pulmonary Arterial Hypertension—Physiology and Pathobiology," J Am Coll Cardiol., 62(25):D22-33 (2013).
Verel et al., "Comparison of left atrial pressure and wedge pulmonary capillary pressure—Pressure gradients between left atrium and left ventricle," British Heart J., 32:99-102 (1970).
Viaene et al., "Pulmonary oedema after percutaneous ASD-closure," Acta Cardiol., 65(2):257-260 (2010).
Wang et al., "A Low Temperature Drifting Acoustic Wave Pressure Sensor with an Integrated Vacuum Cavity for Absolute Pressure Sensing," Sensors, 20(1788):1-13 (2020).
Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).
Webb et al., "Atrial Septal Defects in the Adult Recent Progress and Overview," Circulation, 114:1645-1653 (2006).
Wiedemann, H.R., "Earliest description by Johann Friedrich Meckel, Senior (1750) of what is known today as Lutembacher syndrome (1916)," Am J Med Genet., 53(1):59-64 (1994) (Abstract Only).
Written Opinion of the International Searching Authority dated Apr. 7, 2008 in Int'l PCT Patent Appl. Serial No. PCT/IL05/00131 (0410).
Yantchev et al., "Thin Film Lamb Wave Resonators in Frequency Control and Sensing Applications: A Review," Journal of Micromechanics and Microengineering, 23(4):043001 (2013).
Zhang et al., "Acute left ventricular failure after transcatheter closure of a secundum atrial septal defect in a patient with hypertrophic cardiomyopathy," Chin Med J., 124(4):618-621 (2011).
Zhang et al., "Film bulk acoustic resonator-based high-performance pressure sensor integrated with temperature control system," J Micromech Microeng., 27(4):1-10 (2017).
Zhou, et al., Unidirectional Valve Patch for Repair of Cardiac Septal Defects with Pulmonary Hypertension, Annals of Thoracic Surgeons, 60:1245-1249, (1995).
Borlaug, et al., Latent Pulmonary Vascular Disease May Alter The Response to Therapeutic Atrial Shunt Device in Heart Failure, Circulation (Mar. 2022).
Flachskampf, et al., Influence of Orifice Geometry and Flow Rate on Effective Valve Area: An In Vitro Study, Journal of the American College of Cardiology, 15(5):1173-1180 (Apr. 1990).
International Search Report & Written Opinion dated May 17, 2022 in Int'l PCT Patent Appl. Serial No. PCT/IB2022/051177 (2310).
Kaye, et al., One-Year Outcomes After Transcatheter Insertion of an Interatrial Shunt Device for the Management of Heart Failure with Preserved Ejection Fraction, Circulation: Heart Failure, 9(12):e003662 (Dec. 2016).
Shah, et al., Atrial Shunt Device For Heart Failure With Preserved and Mildly Reduced Ejection Fraction (REDUCE LAP-HF II): A Randomised, Multicentre, Blinded, Sham-Controlled Trial, The Lancet, 399(10330):1130-1140 (Mar. 2022).

\* cited by examiner

DEVICES WITH DIMENSIONS THAT CAN BE REDUCED AND INCREASED IN VIVO, AND METHODS OF MAKING AND USING THE SAME

CROSS-REFERENCE TO RELATED APPLICATIONS

This application is a continuation of U.S. patent application Ser. No. 17/092,081, filed Nov. 6, 2020, which is a continuation of U.S. patent application Ser. No. 16/875,652, filed May 15, 2020, now U.S. Pat. No. 10,898,698, which claims the benefit of priority of U.S. Provisional Patent Application Ser. No. 63/019,777, filed May 4, 2020, the entire contents of each of which are incorporated by reference herein.

This application is also a continuation-in-part of U.S. patent application Ser. No. 16/963,139, filed Jul. 17, 2020, which is a national phase application under 35 U.S.C. § 371 of PCT/IB2019/050452, filed Jan. 19, 2019, which claims the benefit of priority of U.S. Provisional Patent Application Ser. No. 62/619,748, filed Jan. 20, 2018, the entire contents of each of which are incorporated by reference herein.

This application is also a continuation-in-part of International PCT Patent Application Serial No. PCT/IB2021/053594, filed Apr. 29, 2021, which is a continuation-in-part of U.S. patent application Ser. No. 17/092,081, filed Nov. 6, 2020, which is a continuation of U.S. patent application Ser. No. 16/875,652, filed May 15, 2020, now U.S. Pat. No. 10,898,698, which claims the benefit of priority of U.S. Provisional Patent Application Ser. No. 63/019,777, filed May 4, 2020, the entire contents of each of which are incorporated by reference herein.

FIELD OF THE INVENTION

This application generally relates to devices for use in the human body, such as percutaneously implanted devices and methods for adjusting the flow of fluid, such as blood, within the human body.

BACKGROUND

For a number of medical conditions, there is benefit in adjusting the flow of fluid within the human body, for example, through a passage between two body cavities. Such a passage is typically used in catheterization procedures where the catheter is delivered through a patient's vasculature. In some catheterization procedures, there is a benefit in moving from one cavity to another cavity by creating a passage. For example, such a passage may be formed between the right side of the heart and the left side of the heart, e.g., between the right atrium toward the left atrium, where clinical procedures are done on the left side of the heart using an entry from the right side of the heart. Such clinical procedures include, e.g., arrhythmia ablation procedures in the left atrium and mitral valve repair activities.

In addition, a passage may be created and maintained in a heart wall between two heart chambers for housing a shunt for redistributing blood from one heart chamber to another to address pathologies such as heart failure (HF), myocardial infarction (MI), and pulmonary arterial hypertension (PAH). HF is the physiological state in which cardiac output is insufficient to meet the needs of the body or to do so only at a higher filling pressure. There are many underlying causes of HF, including MI, coronary artery disease, valvular disease, hypertension (such as PAH), and myocarditis. Chronic heart failure is associated with neurohormonal activation and alterations in autonomic control. Although these compensatory neurohormonal mechanisms provide valuable support for the heart under normal physiological circumstances, they also play a fundamental role in the development and subsequent progression of HF.

HF is generally classified as either systolic heart failure ("SHF") or diastolic heart failure ("DHF"). In SHF, the pumping action of the heart is reduced or weakened. A common clinical measurement is the ejection fraction, which is a function of the blood ejected out of the left ventricle (stroke volume) divided by the maximum volume in the left ventricle at the end of diastole or relaxation phase. A normal ejection fraction is greater than 50%. Systolic heart failure generally causes a decreased ejection fraction of less than 40%. Such patients have heart failure with reduced ejection fraction ("HFrEF"). A patient with HFrEF may usually have a larger left ventricle because of a phenomenon called "cardiac remodeling" that occurs secondarily to the higher ventricular pressures.

In DHF, the heart generally contracts well, with a normal ejection fraction, but is stiffer, or less compliant, than a healthy heart would be when relaxing and filling with blood. Such patients are said to have heart failure with preserved ejection fraction ("HFpEF"). This stiffness may impede blood from filling the heart and produce backup into the lungs, which may result in pulmonary venous hypertension and lung edema. HFpEF is more common in patients older than 75 years, especially in women with high blood pressure.

Both variants of HF have been treated using pharmacological approaches, which typically involve the use of vasodilators for reducing the workload of the heart by reducing systemic vascular resistance, as well as diuretics, which inhibit fluid accumulation and edema formation, and reduce cardiac filling pressure. No pharmacological therapies have been shown to improve morbidity or mortality in HFpEF whereas several classes of drugs have made an important impact on the management of patients with HFrEF, including renin-angiotensin antagonists, neprilysin inhibitors, beta blockers, mineralocorticoid antagonists and sodium-glucose co-transporter-2 (SGLT2) inhibitors, Nonetheless, in general, HF remains a progressive disease and most patients have deteriorating cardiac function and symptoms over time. In the U.S., there are over 1 million hospitalizations annually for acutely worsening HF and mortality is higher than for most forms of cancer.

In more severe cases of HFrEF, mechanical circulatory support (MCS) devices such as mechanical pumps are used to reduce the load on the heart by performing all or part of the pumping function normally done by the heart. Chronic left ventricular assist devices ("LVAD"), the total artificial heart, and cardiac transplantation are used as measures of last resort. However, such assist devices typically are intended to improve the pumping capacity of the heart, to increase cardiac output to levels compatible with normal life, and to sustain the patient until a donor heart for transplantation becomes available. This usage of MCS is also known as "bridge to transplant" therapy". As the supply of donor hearts for transplantation is insufficient for the demand, more often MCS is the only therapeutic option—also known as "destination therapy." Such mechanical devices enable propulsion of significant volumes of blood (liters/min) but are limited by a need for a power supply, relatively large pumps, and pose a risk of hemolysis, thrombus formation, and infection. Temporary assist devices, intra-aortic balloons, and pacing devices have also been used.

Various devices have been developed using stents to modify blood pressure and flow within a given vessel, or between chambers of the heart. For example, U.S. Pat. No. 6,120,534 to Ruiz is directed to an endoluminal stent for regulating the flow of fluids through a body vessel or organ, for example, for regulating blood flow through the pulmonary artery to treat congenital heart defects. The stent may include an expandable mesh having balloon-expandable lobed or conical portions joined by a shape-memory constricted region, which limits flow through the stent. The constricted region may be adjusted in vivo, and in addition may be heated to recover a maximum degree of constriction. Ruiz is silent on the treatment of HF or the reduction of left atrial pressure.

U.S. Patent Publication No. 2013/0178784 to McNamara describes an adjustable pressure relief shunt that may be expanded, e.g., via an inflation balloon. A tubular body of the shunt may be plastically deformed in vivo, such that the size of the shunt may be repeatedly adjusted by a variety of mechanisms, for example, elastically wound springs or a series of pawls and one-way mechanical ramps, responsive to measurements of the patient's physiological parameters. A key drawback to the approach described in that patent is the hysteresis effect, i.e., non-reversible changes in the underlying crystalline structure that occur when the shunt is permanently deformed. Importantly, such plastic deformation may lead to stress and fatigue-related fracture of the device.

U.S. Pat. No. 6,468,303 to Amplatz et al. describes a collapsible medical device and associated method for shunting selected organs and vessels. Amplatz describes that the device may be suitable to shunt a septal defect of a patient's heart, for example, by creating a shunt in the atrial septum of a neonate with hypoplastic left heart syndrome ("HLHS"). That patent also describes that increasing mixing of pulmonary and systemic venous blood improves oxygen saturation, and that the shunt may later be closed with an occluding device. Amplatz is silent on the treatment of HF or the reduction of left atrial pressure, as well as on means for regulating the rate of blood flow through the device.

Implantable interatrial shunt devices have been successfully used in patients with severe symptomatic heart failure. By diverting or shunting blood from the left atrium ("LA") to the right atrium ("RA"), the pressure in the left atrium is lowered or prevented from elevating as high as it would otherwise (left atrial decompression). Such an accomplishment would be expected to prevent, relieve, or limit the symptoms, signs, and syndromes associated of pulmonary congestion. These include severe shortness of breath, pulmonary edema, hypoxia, the need for acute hospitalization, mechanical ventilation, and death.

Shunt flow is generally governed by the pressure gradient between the atria and the fluid mechanical properties of the shunt device. The latter are typically affected by the shunt's geometry and material composition. For example, the general flow properties of similar shunt designs have been shown to be related to the mean interatrial pressure gradient and the effective orifice diameter.

Percutaneous implantation of interatrial shunts generally requires transseptal catheterization immediately preceding shunt device insertion. The transseptal catheterization system is generally placed from an entrance site in the femoral vein, across the interatrial septum in the region of fossa ovalis ("FO"), which is the central and thinnest region of the interatrial septum. The FO in adults is typically 15-20 mm in its major axis dimension and <3 mm in thickness, but in certain circumstances may be up to 10 mm thick. LA chamber access may be achieved using a host of different techniques familiar to those skilled in the art, including but not limited to: needle puncture, stylet puncture, screw needle puncture, and radiofrequency ablation. The passageway between the two atria is dilated to facilitate passage of a shunt device having a desired orifice size. Dilation generally is accomplished by advancing a tapered sheath/dilator catheter system or inflation of an angioplasty type balloon across the FO. This is the same general location where a congenital secundum atrial septal defect ("ASD") would be located.

U.S. Patent Publication No. 2005/0165344 to Dobak, III describes apparatus for treating heart failure that includes a tubular conduit having an emboli filter or valve, the device configured to be positioned in an opening in the atrial septum of the heart to allow flow from the left atrium into the right atrium. Dobak discloses that shunting of blood may reduce left atrial pressures, thereby preventing pulmonary edema and progressive left ventricular dysfunction, and reducing LVEDP. Dobak describes that the device may include deployable retention struts, such as metallic arms that exert a slight force on the atrial septum on both sides and pinch or clamp the device to the septum.

In addition, following implantation of a shunt device within a heart wall, tissue ingrowth including an endothelial layer or neointima layer typically forms on the device, thereby inhibiting thrombogenicity of the shunt device, and narrowing the size of the passage through the device.

SUMMARY OF THE INVENTION

The present invention overcomes the drawbacks of previously-known systems and methods by providing devices with dimensions that not only may be increased, but also may be reduced in vivo, and methods of making and using the same.

In particular, the present invention overcomes the limitations of previously known devices and methods by providing an implantable device with a composite structure exhibiting both superelastic and shape-memory properties at body temperature. Dimensions that may affect blood flow or other intended interactions between the implanted device and its biological host can be repeatedly altered in either direction by mechanical deformation of one crystalline phase of the shape-memory component in one direction and reversing the direction by temperature induction of a crystalline phase change of the shape-memory component material to its original dimension, greatly simplifying catheter related manipulations.

Under one aspect, an interatrial shunt for placement at an atrial septum of a patient's heart is provided herein. The interatrial shunt includes a body that includes first and second regions coupled in fluid communication by a neck region. The body includes a shape-memory material. The body defines a passageway through the neck region for blood to flow between a first atrium and a second atrium. The first and second regions are superelastic at body temperature, and the neck region is malleable at body temperature. A flow area of the passageway through the neck region may be adjusted in vivo.

The first and second regions that are superelastic may include NITINOL having an austenitic finish temperature (Af) between 5-20° C. The neck region that is malleable may include NITINOL having an austenitic finish temperature (Af) between 45-60° C. The neck region may be mechanically expandable. The neck region may be thermally contractible.

Under another aspect, an interatrial shunt is provided for placement at an atrial septum of a patient's heart for adjustably regulating fluid flow therethrough. The interatrial shunt may include a first expandable end region configured to be placed in a first atrium of the heart, and a second expandable end region configured to be placed in a second atrium of the heart. The first and second expandable end regions may include self-expanding superelastic material. The interatrial shunt may include a neck region between the first and second expandable end regions. The neck region may be configured for placement at the atrial septum. The neck region may include malleable shape-memory material. The interatrial shunt may define a passageway through the neck region for blood to flow between the first atrium and the second atrium. The neck region may be heat treated to exhibit different shape memory properties than the first and second expandable end regions such that a cross-sectional area of the passageway is adjustable in vivo.

The malleable shape-memory material may be configured to be expanded in vivo such that the passageway expands from the cross-sectional area to a second cross-sectional area larger than the cross-sectional area. The malleable shape-memory material may be configured to be contracted in vivo such that the passageway contracts from the second cross-sectional area to a third cross-sectional area smaller than the second cross-sectional area. The cross-sectional area may be between 4.9 to 28.3 mm$^2$ and the second cross-sectional area and the third cross-sectional area may be between 15.9 to 78.6 mm$^2$. The malleable shape-memory material may include NITINOL having an austenitic finish temperature (Af) between 45-60° C. The self-expanding superelastic material may include NITINOL having an austenitic finish temperature (Af) between 5-20° C. The malleable shape-memory material may be mechanically expandable. The malleable shape-memory material may be thermally contractible. The cross-sectional area of the neck region may be smaller than respective cross-sectional areas of at least one of the first and second expandable end regions. The first and second expandable end regions may extend into the first and second atria, respectively, such that respective ends of the first and second expandable end regions may not contact the atrial septum. The first and second expandable end regions and the neck region may comprise a diabolo-shaped shunt. The neck region may include a cylindrical shunt. The cylindrical shunt may be outside of the diabolo-shaped shunt. The cylindrical shunt may be formed of the malleable shape-memory material such that the cylindrical shunt radially constrains a dimension of the diabolo-shaped shunt at the neck region, and the diabolo-shaped shunt may self-expand at the neck region responsive to the malleable shape memory material expanding to a second cross-sectional area. The cylindrical shunt may be inside of the diabolo-shaped shunt. The cylindrical shunt may not be directly coupled to the diabolo-shaped shunt and the neck region. The device may further include an encapsulant indirectly and elastically coupling the cylindrical shunt to the diabolo-shaped shunt. Contraction of the cylindrical shunt may not cause contraction of the diabolo-shaped shunt at the neck region. The diabolo-shaped shunt and the cylindrical shunt may be integrally formed from a common frame. The first and second expandable end regions and the neck region may be integrally formed from a common frame. The first and second expandable end regions and the neck region may be at least partially encapsulated with a biocompatible material.

Under another aspect, an interatrial shunt for adjustably regulating fluid flow in a heart having a first atrium, a second atrium, and an atrial septum is provided. The interatrial shunt may include a first region that includes a self-expanding superelastic material configured to be placed in the first atrium. The first region may be superelastic at body temperature. The interatrial shunt may include a second region that includes a malleable shape-memory material configured to be placed through an opening in the atrial septum so as to provide fluid flow from the first atrium to the second atrium. The second region may be malleable at body temperature. The malleable shape-memory material may have a first cross-sectional area. The malleable shape-memory material may be expandable from the first cross-sectional area to a second cross-sectional area. The malleable shape-memory material may be contractible from the second cross-sectional area to a third cross-sectional area.

The self-expanding superelastic material may include NITINOL having an austenitic finish temperature (Af) between 5-20° C., and the malleable shape-memory material may include NITINOL having an austenitic finish temperature (Af) between 45-60° C. The malleable shape-memory material may be mechanically expandable and thermally contractible. The interatrial shunt may include a third region that includes a second self-expanding superelastic material, is configured to be placed in the second atrium, and is coupled to the second region.

In accordance with another aspect, a device is provided for adjustably regulating fluid flow therethrough. The device may include a first component including a first self-expanding superelastic material, and a second component coupled to the first component and including a first malleable shape-memory material. The first malleable shape-memory material may have a first cross sectional area. The first malleable shape-memory material may be expandable to a second cross sectional area. The first malleable shape-memory material may be contractible to a third cross sectional area.

In some examples, the first self-expanding superelastic material includes NITINOL having an austenitic finish temperature (Af) of less than body temperature (normally ~37° C.). Illustratively, the Af of the NITINOL of the first self-expanding superelastic material may be between 5-20° C.

In some examples, the first malleable shape-memory material includes NITINOL having an austenitic finish temperature (Af) of greater than body temperature or 37° C. Illustratively, the Af of the NITINOL of the malleable shape-memory material may be between 45-60° C. This is higher than body temperature when febrile but not high enough to cause permanent injury such a protein denaturation from brief exposure.

In some examples, the first malleable shape-memory material is mechanically expandable. In some examples, the first malleable shape-memory material is thermally contractible. In some examples, the first malleable shape-memory material is joined to the first self-expanding superelastic material by welding. In some examples, the device includes an encapsulant covering at least a portion of at least one of the first component and the second component. Optionally, the encapsulant joins the first malleable shape-memory material to the first self-expanding superelastic material.

In some examples, the first cross sectional area is smaller than the third cross sectional area. In some examples, the first cross sectional area is larger than the third cross sectional area.

In some examples, the device further includes a third component including a second self-expanding superelastic material and coupled to the first component and the second component. Optionally, the first component includes an inlet, the second component includes a neck, and the third component includes an outlet fluidically coupled to the inlet via the neck. As a further option, the cross sectional area of the neck is smaller than respective cross sectional areas of at least one of the inlet and the outlet. As a still further option, the inlet and outlet anchor the device within an opening through a septum between two chambers within the body, and the neck provides a channel for flow between these chambers. In other options, the cross sectional area of the neck is larger than respective cross sectional areas of at least one of the inlet (ingress of blood flow) and the outlet (egress of blood flow). Optionally, the second component is configured to engage an opening in the human body. As a further option, the opening may be created through a fossa ovalis of an interatrial septum between a right atrium and a left atrium. The neck may be configured to engage the opening, the inlet may be configured to extend into the right atrium, and the outlet may be configured to extend into the left atrium.

In some examples, the first component is configured to engage a lumen in the human body. Optionally, the lumen includes a blood vessel, and the first and third components are configured to engage the blood vessel. The neck may be configured to be disposed adjacent to an ostium of the blood vessel.

In some examples, the device includes a third component including a second malleable shape-memory material and coupled to the first component and the second component. Optionally, the second malleable shape-memory material has a fourth cross sectional area permitting a fourth rate of fluid flow therethrough. The second malleable shape-memory material may be expandable to a fifth cross sectional area permitting a fifth rate of fluid flow therethrough. The second malleable shape-memory material may be contractible to a sixth cross sectional area permitting a sixth rate of fluid flow therethrough. Optionally, the second component includes an inlet and the third component includes an outlet fluidically coupled to the inlet via the first component. As a further option, the inlet is configured to engage a blood vessel in the human body, the first component is configured to engage the blood vessel, and the outlet is configured to extend into an ostium of the blood vessel.

In some examples, the device further includes a valve disposed in the second component. The first component may be configured to engage a blood vessel in the human body, and the second component may extend into the blood vessel.

In some examples, the second component is located inside of the first component.

In some examples, the first component includes a diabolo-shaped shunt having a neck, and the second component includes a cylindrical shunt. Optionally, the cylindrical shunt is outside of the diabolo-shaped shunt. As a further option, the first malleable shape-memory material may radially constrain a dimension of the neck. The first malleable shape-memory material optionally radially contacts an outer surface of the neck so as to constrain the neck from self-expanding to a larger dimension. Optionally, the neck self-expands responsive to the first malleable shape memory material expanding to the second cross sectional area. The device optionally further includes an encapsulant forming an inner lumen through the first component and an outer covering of the first component and the second component.

In other examples, the cylindrical shunt is inside of the diabolo-shaped shunt. Optionally, the cylindrical shunt is inside of, and not directly coupled to, the neck of the diabolo-shaped shunt. The device optionally further includes an encapsulant indirectly and elastically coupling the cylindrical shunt to the diabolo-shaped shunt such that the encapsulant forms a lumen through the inner cylindrical shunt. Optionally, contraction of the cylindrical shunt does not cause contraction of neck of the outer diabolo-shaped shunt. Optionally, the neck of the diabolo-shaped shunt is self-expandable to a fourth cross sectional area.

In some examples, the second component is located inside of the first component.

Optionally, the first malleable shape-memory material radially constrains a dimension of the first component. Optionally, the first malleable shape-memory material radially contacts an inner surface of the first component so as to constrain the first component from contracting to a smaller dimension. Optionally, the first component self-contracts responsive to the first malleable shape memory material contracting to the third cross sectional area. Optionally, the device further includes an encapsulant forming an outer covering of the first component and the second component.

Under another aspect, a method for reducing and increasing an internal dimension of a device in vivo is provided. The method may include inserting into a fluid path first and second components coupled to one another. The first component may include a self-expanding superelastic material, and the second component may include a malleable shape-memory material having a first cross sectional area. The method may include expanding the malleable shape-memory material to a second cross sectional area; and contracting the malleable shape-memory material to a third cross sectional area.

In some examples, contracting the malleable shape-memory material includes heating the malleable shape-memory material. In some examples, the heating includes flowing heated saline through the device via a catheter. In some examples, the heating includes applying radio frequency (RF) energy to the device. In some examples, expanding the malleable shape-memory material includes expanding a balloon within the malleable shape-memory material.

Under another aspect, a method for adjustably regulating fluid flow is provided. The method may include inserting into a fluid path first and second components coupled to one another. The first component may include a self-expanding superelastic material, and the second component may include a malleable shape-memory material having a first cross sectional area permitting a first rate of fluid flow therethrough. The method may include expanding the malleable shape-memory material to a second cross sectional area permitting a second rate of fluid flow therethrough; and contracting the malleable shape-memory material to a third cross sectional area permitting a third rate of fluid flow therethrough.

In some examples, contracting the malleable shape-memory material includes heating the malleable shape-memory material. In some examples, the heating includes flowing heated saline through the device via a catheter. In some examples, the heating includes applying radio frequency (RF) energy to the device. In some examples, expanding the malleable shape-memory material includes expanding a balloon within the malleable shape-memory material.

Under another aspect, a repositionable device for fixation within a body lumen is provided. The device may include a first component including a self-expanding superelastic material; and a second component coupled to the first component and including a malleable shape-memory material. The self-expanding superelastic material may have a predetermined fully expanded dimension. The second component may have a first dimension suitable for deployment through a catheter. The malleable shape-memory material may be expandable to a second dimension for fixation within a body lumen. The malleable shape-memory material may be thermally transitionable to a third dimension. The malleable shape-memory material may be mechanically re-expandable to a fourth dimension.

Under another aspect, a method for adjustably fixating a device within a body lumen is provided. The method may include inserting into a body lumen a device including first and second components coupled to one another. The first component may include a self-expanding superelastic material. The second component may include a malleable shape-memory material having a first dimension. The method may include expanding the malleable shape-memory material to a second dimension to fixate the device within a body lumen. The method may include thermally contracting the malleable shape-memory material. The method may include repositioning the device within the body lumen while the malleable shape-memory material is thermally contracted. The method may include mechanically re-expanding the malleable shape-memory material to a third dimension to fixate the device within the body lumen.

In some examples, thermally contracting the malleable shape-memory material includes heating the malleable shape-memory material. In some examples, the heating includes flowing heated saline through the device via a catheter. In some examples, the heating includes applying radio frequency (RF) energy to the device. In some examples, the mechanically expanding the malleable shape-memory material includes expanding a balloon within the malleable shape-memory material.

In any of the aforementioned devices and methods, the first component and the second component optionally are integrally formed from a common frame with one another.

Under another aspect, a dilator for enlarging an opening through a region of the human body is provided. The dilator may include a sheath having a proximal end and a distal end; and a dilator disposed at the distal end of the sheath and including a tip, an enlarged region, and a reduced region. The reduced region may be sized so as to securably engage with the distal end of the sheath. The enlarged region may be sized so as to provide a smooth profile between the sheath and the tip. A distal end of the tip may taper to approximately a point. At least the enlarged region and the reduced region may include a martensitic shape-memory material having an austenitic finish temperature (Af) substantially greater than 37° C. such that, upon application of heat within the body, the shape memory material returns to a smaller, heat-set outer dimension such that the dilator has a substantially smooth, reduced size profile.

In some examples, the tip also includes the martensitic shape-memory material. In some examples, the tip includes a self-expanding superelastic material. The tip, the reduced region, and the enlarged region optionally are integrally formed from a common frame with one another.

Under another aspect, a system is provided that includes such a dilator, and a device to deploy in the opening.

Under another aspect, a method for forming an enlarged opening through a region of the human body is provided. The method may include disposing a guidewire through the region of the human body to form an opening. The method may include pushing a dilator over the guidewire and through the opening to form an enlarged opening. The method may include heating the dilator to reduce the size of the dilator. The method may include, while the dilator has the reduced size, withdrawing the dilator through the enlarged opening.

In some examples, the heating includes flowing heated saline through the dilator via a catheter. In some examples, the heating includes applying radio frequency (RF) energy to the dilator. In some examples, the method includes deploying a device within the opening, and withdrawing the dilator through the device.

Under another aspect, a transatrial gate is provided. The transatrial gate may include a left atrial disc including a first self-expanding superelastic material, and a right atrial disc including a second self-expanding superelastic material. The transatrial gate also may include a martensitic shape-memory material that is heat set to completely occlude passage between the left and right atrial discs that is expandable to allow passage between the left and right atrial discs.

In some examples, the martensitic shape-memory material is provided as a mesh. In some examples, the martensitic shape-memory material is balloon expandable. In some examples, the martensitic shape-memory material is configured to be closeable by application of heat after being expanded to allow passage between the left and right atrial discs. The left atrial disc, the right atrial disc, and the martensitic shape memory material optionally are integrally formed from a common frame with one another.

Under another aspect, a method of performing a procedure is provided. The method may include implanting a transatrial gate through an opening in an atrial septum of a heart. The transatrial gate may include a left atrial disc including a first self-expanding superelastic material, and a right atrial disc including a second self-expanding superelastic material. The transatrial gate also may include a martensitic shape-memory material that is heat set to completely occlude passage between the left and right atrial discs. The method may include expanding the martensitic shape-memory material to allow passage between the left and right atrial discs.

In some examples, the material includes blood. In some examples, the material includes an instrument. In some examples, the method includes using the instrument to perform an additional procedure in a left atrium of the heart. In some examples, the additional procedure includes RF ablation, left atrial appendage closure, MitraClip implantation, mitral valve replacement, or mitral valve repair. In some examples, the martensitic shape-memory material is provided as a mesh. In some examples, the martensitic shape-memory material is expanded using a balloon. In some examples, the method further includes, after the expanding, closing the martensitic shape-memory material by application of heat. The left atrial disc, the right atrial disc, and the martensitic shape memory material optionally are integrally formed from a common frame with one another.

Under yet another aspect, an apparatus is provided. The apparatus includes a device that includes a proximal portion configured to be disposed in a first atrium of a heart, and a distal portion configured to be disposed in a second atrium of a heart and including a first self-expanding superelastic material. The device further includes an intermediate portion disposed between the proximal portion and the distal portion and configured to be disposed in an atrial septum between the first atrium and the second atrium. The intermediate portion includes a malleable shape-memory material. The apparatus further includes a catheter and at least one constricting flexible longitudinal element. The first self-expanding superelastic material may have a predetermined fully expanded dimension. The intermediate portion may have a first dimension suitable for deployment through the catheter, may be expandable to a second dimension for fixation within the septum, may be thermally transitionable to a third dimension, and may be mechanically re-expandable to a fourth dimension. The device may be removable by drawing the device into the catheter using the at least one constricting flexible longitudinal element.

In some examples, the proximal portion is flared. In some examples, the distal portion is flared. In some examples, the proximal portion includes a second self-expanding superelastic material. The proximal portion, the distal portion, and the intermediate portion optionally are integrally formed from a common frame with one another.

Under another aspect, a method is provided that includes through a catheter, deploying a device through an atrial septum of a heart. The device may include a proximal portion disposed in a first atrium of the heart, and a distal portion disposed in a second atrium of the heart and comprising a first self-expanding superelastic material. The device may include an intermediate portion disposed between the proximal portion and the distal portion and disposed in the atrial septum between the first atrium and the second atrium. The intermediate portion may include a malleable shape-memory material. The first self-expanding superelastic material may have a predetermined fully expanded dimension. The intermediate portion may have a first dimension when deployed through the catheter. The method may include expanding the intermediate portion to a second dimension for fixation within the septum. The method may include thermally transitioning the intermediate portion to a third dimension. The method may include mechanically re-expanding the intermediate portion to a fourth dimension. The method may include removing the device by drawing the device into the catheter using the at least one constricting flexible longitudinal element.

In some examples, the proximal portion is flared. In some examples, the distal portion is flared. In some examples, the proximal portion includes a second self-expanding superelastic material. The proximal portion, the distal portion, and the intermediate portion optionally are integrally formed from a common frame with one another.

DETAILED DESCRIPTION

Figure 1A:
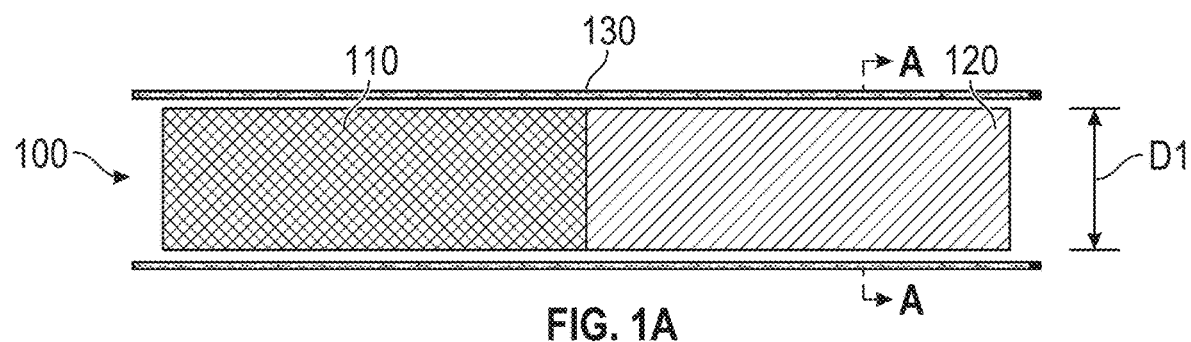
FIGS. 1A-1E schematically illustrate an example device with an internal dimension that can be reduced and increased in vivo.

The present disclosure provides devices with dimensions that can be reduced and increased in vivo, and methods of making and using the same.

For example, the present devices may be permanently or temporarily implantable in a human body and include one or more components which can be adjusted for size, larger or smaller, after implantation. The need for such adjustable devices may arise, for example, in the treatment of pulmonary artery hypertension (PAH) or heart failure (HF). In PAH, placing a shunt in the interatrial septum allows excessive blood pressure in the right atrium to be relieved by allowing some blood to flow from the right atrium to the left atrium through an orifice. In HF, placing a shunt in the interatrial septum allows excessive blood pressure in the left atrium to be relieved by allowing some blood to flow from the left atrium into the right atrium through an orifice. In both PAH and HF, interatrial shunting has been shown to effectively reduce symptoms and increase exercise tolerance. Interatrial shunting also may reduce the need for hospitalization and even improve life expectancy.

However, if the orifice of the interatrial shunt is too small, too little blood may be transferred and the shunt may be relatively ineffective and provide little or no clinical benefit. In contradistinction, shunting too much blood ("over-shunting") through too large of an orifice may lead to severe or even fatal complications over time. For example, in PAH patients, over-shunting may result in systemic oxygen desaturation and its sequalae including cyanosis, polycythemia with increased blood viscosity, end organ ischemia, and potentially death. In HF patients, over-shunting may result in pulmonary hypertension, right ventricular failure, and potentially death.

At present, there is no known way to predict the response of a given patient to a particular shunt orifice size. As is previously known, a shunt orifice may be increased in vivo, for example by dilating a suitably designed shunt by expanding an inflatable balloon catheter or other similar mechanically expansive means within the shunt, providing however, that the shunt is made from a malleable material and will remain expanded due to plastic deformation or some other physical property, whereby when the balloon or other expansive means is removed, the amount of elastic spring back or recoil will be low enough so that the desired increment in orifice size is achieved. One drawback of this approach is that the orifice size can only be increased. If the shunt starts out too large or if is made too large by balloon dilatation but the patient needs a smaller shunt, there is no way to go back to a smaller size orifice except by providing another, smaller shunt or placing a smaller shunt within the lumen of original shunt. This technique is known as "shunt-in-shunt." As such, finding a suitable shunt orifice size for a given patient has been a trial and error process in which the shunt orifice size is selected according to the patient's response, which may be observed for a period of time which may be as short as a few minutes or as long as many months, and the shunt orifice size increased (e.g., by balloon dilatation) or reduced (by providing a new, smaller shunt) depending on the patient's response. As such, opportunities to increase or reduce the size of the shunt are very limited and may not be repeatable. Furthermore, the extent to which an inflatable balloon catheter can expand a shunt orifice may be limited by the maximum size of the balloon. Thus, what is needed is a means to repeatedly and non-traumatically adjust the orifice size of shunts, and other implantable devices, in vivo, and in both directions, bigger or smaller.

Provided herein are devices with cross sectional areas that may be easily reduced in vivo, and expanded in vivo, in any order, as clinically necessary. In particular, some examples of the present devices include a self-expanding superelastic (austenitic phase) material as well as a malleable shape-memory (martensitic phase) material. When the device is implanted in the human body, e.g., by transporting the device in a compressed state within a sheath to a desired location and then removing the sheath, the self-expanding superelastic material may automatically deploy to its desired size, while the malleable shape-memory material initially may remain in a reduced size state. The cross sectional area of the malleable shape-memory material then may be expanded and reduced in vivo as desired so as to obtain a cross sectional area that is suitable for treating the patient, e.g., by providing a suitable fluid flow rate therethrough, or so as to appropriately fixate the device within the patient while allowing for repositioning to improve effectiveness of the treatment. A wide variety of devices may be prepared using components respectively including self-expanding superelastic materials and malleable shape-memory materials, such as exemplified herein.

For example, FIGS. 1A-1E schematically illustrate an example device with an internal dimension that can be reduced and increased in vivo. Device 100 illustrated in FIGS. 1A-1E includes first component 110 and second component 120 coupled, e.g., fluidically coupled, to first component 110. First component 110 may include a self-expanding superelastic material, and second component 120 may include a malleable shape-memory material. The malleable shape-memory material of second component 120 may have a first cross sectional area permitting a first rate of fluid flow through the second component, may be expandable to a second cross sectional area permitting a second rate of fluid flow through the second component, and may be contractible to a third cross sectional area permitting a third rate of fluid flow through the second component. Note that the overall rate of fluid flow through device 100 also may depend on the cross sectional area of first component 110.

Figure 1B:
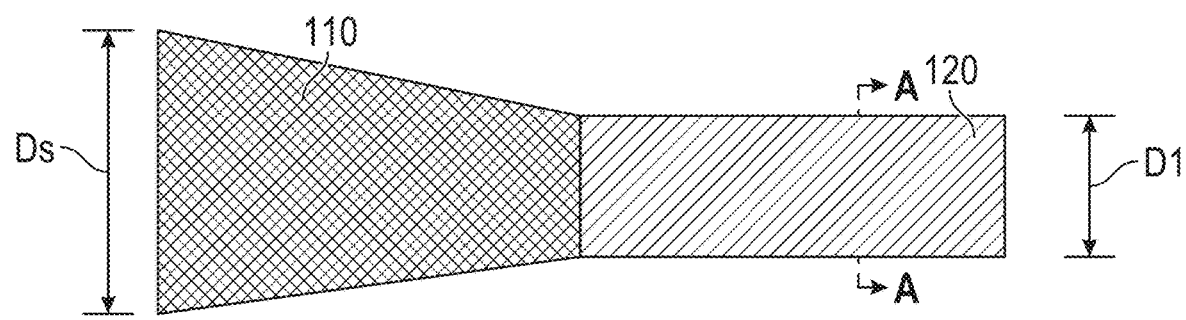
Figure 1C:
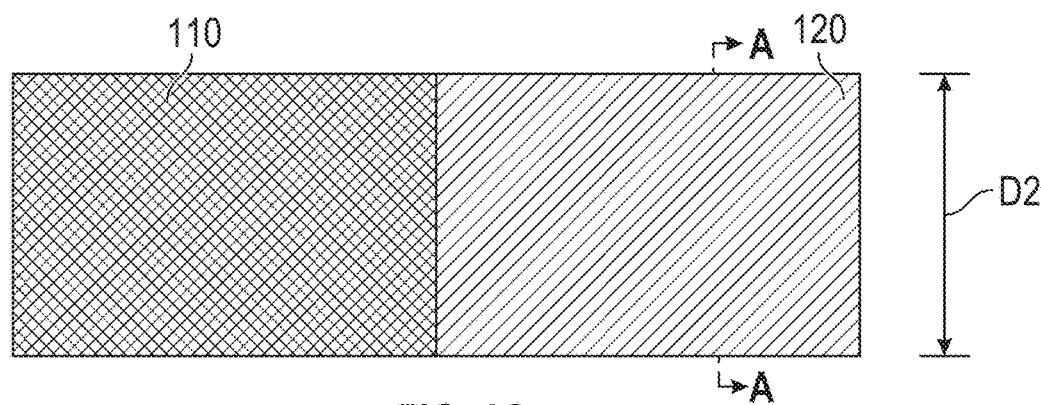
Figure 1D:
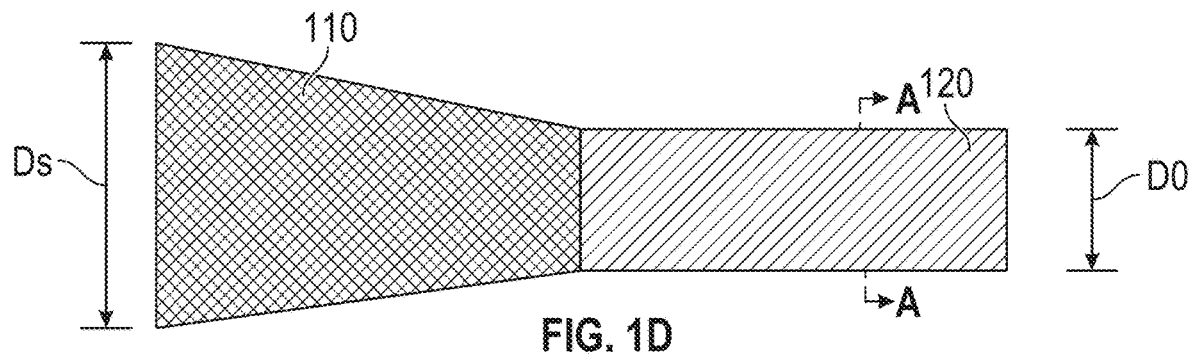
Figure 1E:
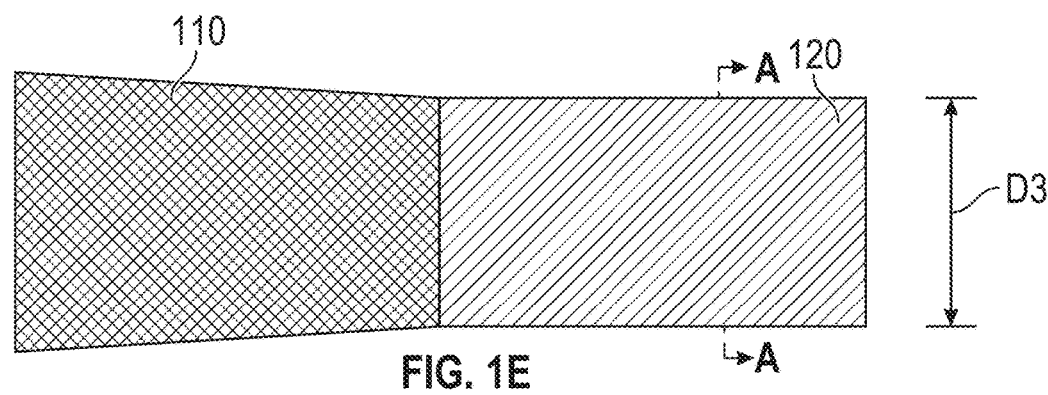

For example, FIG. 1A schematically illustrates device 100 in a compressed or crimped state and loaded into sheath 130 for percutaneous implantation within the human body. In the crimped state, both first component 110 and second component 120 may have a dimension D1 (corresponding to a first cross sectional area). Once device 100 is delivered to the desired location, sheath 130 may be retracted so as to percutaneously implant the device. As illustrated in FIG. 1B, following removal of sheath 130 the self-expanding superelastic material of first component 110 may automatically expand to its heat-set superelastic configuration, in this example with dimension Ds, while the malleable shape-memory material of second component 120 may remain in the crimped state (e.g., at the first dimension, D1, corresponding to a first cross sectional area) until it is further adjusted. Second component 120 may be expanded by any suitable amount, for example such as shown in FIG. 1C, to dimension D2 (corresponding to a second cross sectional area). Second component 120 may be reduced by any suitable amount, for example such as shown in FIGS. 1D and 1E, by first using the shape-memory property to contract component 120 to its annealed configuration dimension D0, then expanding (e.g., by balloon dilation) to dimension D3 (corresponding to a third cross sectional area). Based on the particular dimension (and cross sectional areas) to which second component 120 is adjusted by expansion or contraction, different rates of fluid flow may be permitted through that component, thus providing an adjustable orifice for controlling the flow of fluid within the location of the human body in which device 100 is deployed.

In some examples, reducing the dimension of a shape memory material-based component herein always returns that component to its heat-set (annealed) dimension, D0, determined at the time of manufacture by heat setting within a jig. Once the dimension is thus reduced it may be then expanded, for example by balloon dilation, to an intermediate dimension. Additionally, note that although in some examples D0 and D1 may be approximately the same as one another, in other examples D0 may be smaller than D1, while in still other examples D0 may be larger than D1. Although FIGS. 1A-1E illustrate only four exemplary dimensions D0, D1, D2, D3 of second component 120, it should be appreciated that any suitable dimension above a minimum set by the annealed configuration, D0, may be obtained by balloon expanding as desired. For example, D2 may be smaller than D3. Alternatively, D2 may be larger than D3, and D3 may be achieved by reducing second component 120 to its heat-set dimension, D0, as shown in FIG. 1D, and then expanding second component 120 to dimension D3 as shown in FIG. 1E. In some examples, the second component may be heated with a hot balloon and the balloon then deflated to a desired dimension, followed by cooling of the second component. As heating creates a crystalline phase change, the dimension of the second component is never plastically deformed by balloon inflation and therefore, the shunt can be repeatedly cycled from one dimension to another, bigger or smaller through any number of cycles the patient requires to optimize shunt size.

Note that as used herein, "inner dimension" refers to the transverse dimension between inner walls of a device component, e.g., along line A-A indicated in FIGS. 1A-1E. As used herein, "outer dimension" refers to the transverse dimension between outer walls of a device component, e.g., along line A-A indicated in FIGS. 1A-1E. As used herein, "cross sectional area" refers to the area of the transected plane within the walls of the device in a plane running through that dimension, e.g., in a plane parallel to line A-A indicated in FIGS. 1A-1E and crossing through second component 120. The expansion or contraction of a dimension may be with reference to the distance between walls of the device component at a particular location within that component, e.g., along line A-A indicated in FIGS. 1A-1E. The expansion or contraction of a cross sectional area may be with reference to area within the walls of the device in a plane running through the corresponding dimension of the device component at a particular location within that component, e.g., along line A-A indicated in FIGS. 1A-1E. The present devices may have any suitable cross sectional shape and may include, but are not limited to, circular, or uniform, cross sections.

In the nonlimiting examples shown in FIGS. 1B and 1D, the interface between the crimped state of second component 120 and expanded first component 110 may apply a force that inhibits first component 110 from fully expanding; it should be appreciated that such interface instead may apply a force that causes second component 120 to partially expand. As described in greater detail below, the particular manner in which first component 110 and second component 120 are joined to one another may be selected so as to control the force(s) applied to such components and thus the shapes and dimensions of such components.

In some examples, the self-expanding superelastic material of first component 110 and the malleable shape-memory material of second component 120 may include different materials than one another, or may include the same material as one another but having different phases than one another. For example, first component 110 and second component 120 independently may include one or more materials selected from the group consisting of nickel titanium (NiTi), also known as NITINOL, other shape memory alloys, self-expanding materials, superelastic materials, polymers, and the like. For example, first component 110 may include a NITINOL alloy having an austenitic finish temperature (Af) that is sufficiently below body temperature that the material is in an austenitic, superelastic phase while in the human body. In one nonlimiting example, the self-expanding superelastic material of first component 110 includes NITINOL having an Af of less than 37° C. For example, the Af of the NITINOL of the self-expanding superelastic material may be between 5-20° C. First component 110 and second component 120 optionally may be integrally formed from a common frame with one another. For example, first component 110 and second component 120 may be initially cut and processed as a single unit from the same tubing, sheet, or other suitable configuration of frame as one another. Portions of that common frame may be heat treated differently than one another so as to define first component 110 and second component 120, e.g., in a manner similar to that described with reference to FIGS. 10A-10C.

Second component 120 may include a NITINOL alloy having an austenitic phase transition temperature Af that is slightly above body temperature such that the material remains in its martensitic, shape-memory phase while in the body unless and until it is heated to or above its Af, for example by the injection of warm or hot saline (or other fluid) into the fluid within or flowing through second component 120, or by applying heat through electrical energy such as with an RF energy source. In one nonlimiting example, the malleable shape-memory material of second component 120 includes NITINOL having an austenitic finish temperature (Af) of greater than 37° C. For example, the Af of the NITINOL of the malleable shape-memory material of second component 120 may be between 45-60° C., e.g., from 50-55° C. In some examples, the warm or hot saline (or other fluid) may be injected sufficiently close to second component 120 to heat that component to or above its Af, using a side-hole catheter positioned through device 100. In other examples, a pair of RF electrodes may be brought into contact with device 100, e.g., via a catheter, and actuated at a sufficient voltage and frequency to heat component 120 to or above its Af. In still other examples, any other suitable means of locally applying heat to device 100, such as a laser, magnetic inductance, electrical resistance, or the like, may be used. Heating device 100 using electrical resistance may include contacting the device with a pair of electrodes, e.g., via a catheter, and passing a current through the device that causes heating of the device. Heating device 100 using a laser may include irradiating the device with light from a laser that may be introduced by a catheter. Heating device 100 using magnetic inductance may include passing an alternating magnetic field through the device that induces eddy currents inside the device which heat the device. Note that in blood vessels having a particularly high rate of blood flow (e.g., 2-5 L/min), such as the aorta or internal iliac artery, it may be useful to heat device 100 using direct heating methods, such as using RF energy, a laser, magnetic inductance, or electrical resistance, instead of saline which may be washed away by the high blood flow rate before sufficiently heating the device.

Alternatively, device 100 may include a single NITINOL alloy (common frame) that has been heat treated to produce a lower Af in a region corresponding to first component 110, and that has been heat treated to produce a higher Af in a region corresponding to second component 120, such that first component 110 and second component 120 are integrally formed with one another. The malleable shape-memory material of second component 120 may be expandable and contractible using any suitable technique. For example, the malleable shape-memory material of second component 120 may be mechanically expanded, e.g., using balloon dilatation such as known in the art. Additionally, or alternatively, malleable shape-memory material of second component 120 may be thermally contracted, e.g., using saline at a temperature at or above the Af of that material, or otherwise heated such as with RF energy or the use of a laser, magnetic inductance, electrical resistance, or the like in a manner such as described above.

Optionally, first component 110 may be configured to engage a lumen in the body, for example in a manner such as described with reference to FIGS. 14A-14C, 15A-15D, or 16A-16B. Illustratively, the lumen may include a blood vessel, and the first component may be configured to engage the blood vessel.

It will be appreciated that the present devices may include any suitable number of components including a self-expanding superelastic material, and any suitable number of components including a malleable shape-memory material. For example, FIGS. 2A-2E schematically illustrate another example device with an internal dimension that can be reduced and increased in vivo. Device 200 illustrated in FIGS. 2A-2E includes first component 210, second component 220, and third component 211 which is coupled, e.g., fluidically coupled, to first component 210 and second component 220. First component 210 may include a first self-expanding superelastic material, second component 220 may include a malleable shape-memory material, and third component 211 may include a second self-expanding superelastic material. The malleable shape-memory material of second component 220 may have a first cross sectional area permitting a first rate of fluid flow through the second component, may be expandable to a second cross sectional area permitting a second rate of fluid flow through the second component, and may be contractible to a third cross sectional area permitting a third rate of fluid flow through the second component.

Figure 2A:
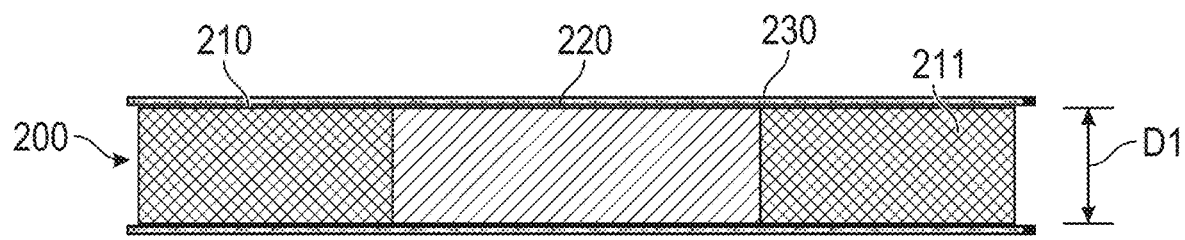
FIGS. 2A-2E schematically illustrate another example device with an internal dimension that can be reduced and increased in vivo.
Figure 2B:
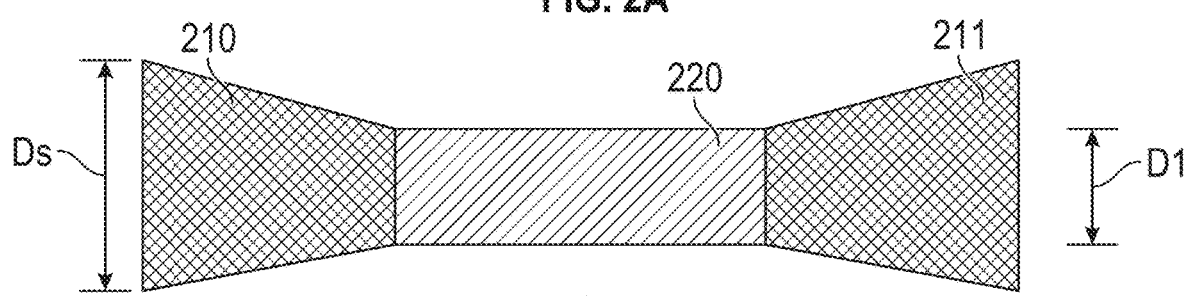
Figure 2C:
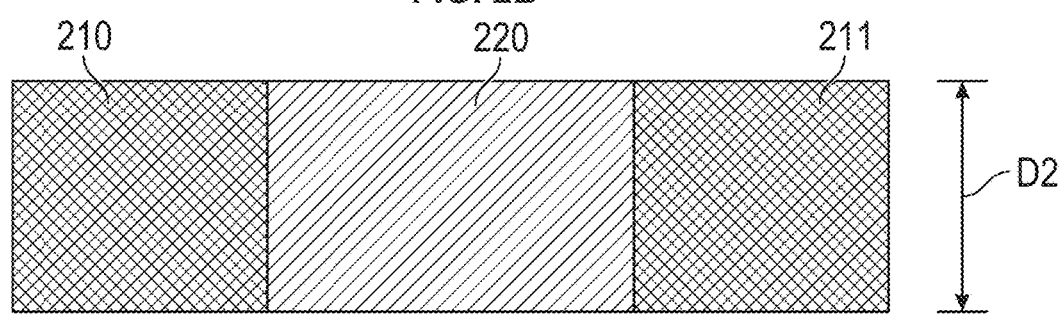
Figure 2D:
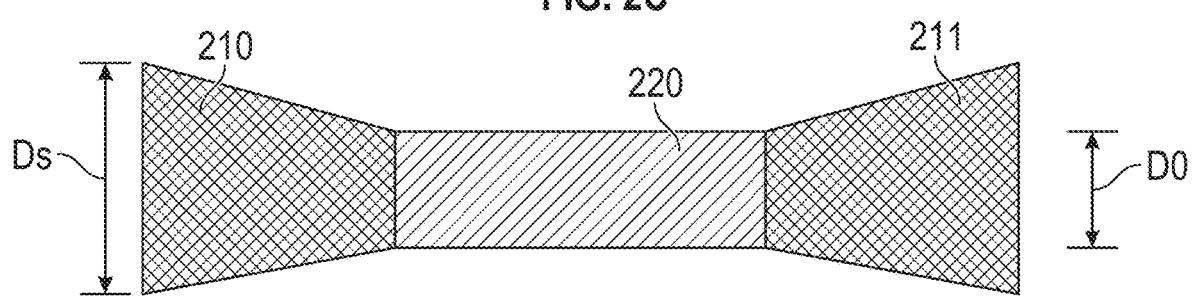
Figure 2E:
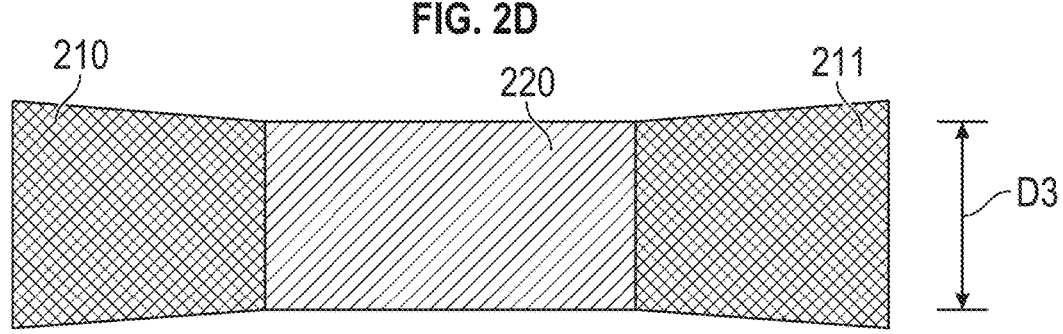

For example, FIG. 2A schematically illustrates device 200 in a crimped state and loaded into sheath 230 for percutaneous implantation within the human body. In the crimped state, first component 210, second component 220, and third component 211 may have a dimension D1 (corresponding to a first cross sectional area). Once device 200 is delivered to the desired location, sheath 230 may be retracted so as to percutaneously implant the device. As illustrated in FIG. 2B, following removal of sheath 230 the respective self-expanding superelastic materials of first component 210 and third component 211 may automatically expand to a heat-set dimension Ds, while the malleable shape-memory material of second component 220 may remain in the crimped state (e.g., at the first cross sectional area) until it is further adjusted. Second component 220 may be expanded by any suitable amount, for example such as shown in FIG. 2C, to dimension D2 (corresponding to a second cross sectional area). Second component 220 may be reduced by any suitable amount in the same manner as described above in relation to FIG. 1, for example such as shown in FIG. 2E, to dimension D3 (corresponding to a third cross sectional area), by first heating the shape-memory component 220 above its Af temperature, returning it so its annealed configuration, D0, as shown in FIG. 2D, then expanding it (e.g. by balloon dilation) to a third dimension D3 (corresponding to a third cross sectional area). Based on the particular dimension (and cross sectional areas) to which second component 220 is adjusted by expansion or contraction, different rates of fluid flow may be permitted through that component, thus providing an adjustable orifice for controlling the flow of fluid within the location of the human body in which device 200 is deployed. Note that the overall rate of fluid flow through device 200 also may depend on the cross sectional areas of first component 210 and second component 211.

Although FIGS. 2A-2E illustrate only three exemplary dimensions D1, D2, D3 of second component 220, it should be appreciated that any suitable dimension may be obtained by expanding or contracting the second component as desired. Note that although in some examples D0 and D1 may be approximately the same as one another, in other examples D0 may be smaller than D1, while in still other examples D0 may be larger than D1. Furthermore, it should be appreciated that a shape-memory component may be formed and heat set into other geometries besides the circular cylindrical shape illustrated here, and that its shape may be modified in other ways besides the radial expansion illustrated here, and that the shape-memory component may be returned to its original, heat-set, geometry by heating it above its Af temperature. Additionally, with regards to each of the examples described herein, it should be appreciated that the components need not necessarily have circular cross sections, but may have any suitable shape of cross section.

In the nonlimiting examples shown in FIGS. 2B and 2D, the respective interfaces between the crimped state of second component 220 and expanded first component 210 and expanded third component 211 may apply a force that inhibits first component 210 and third component 211 from fully expanding; it should be appreciated that such interface(s) instead may apply a force that causes second component 220 to partially expand. As described in greater detail below, the particular manner in which first component 210, second component 220, and third component 211 respectively are joined to one another may be selected so as to control the force(s) applied to such components and thus the shapes and dimensions of such components. First component 210 and third component 211 may be, but need not necessarily be, the same dimension, shape, and size as one another.

In some examples, the first self-expanding superelastic material of first component 210, the malleable shape-memory material of second component 220, and the second self-expanding superelastic material of third component 211 may include different materials than one another, or may include the same material as one another but having different phases than one another. For example, first component 210, second component 220, and third component 211 independently may include one or more materials selected from the group consisting of nickel titanium (NiTi), also known as NITINOL, other shape memory alloys, self-expanding materials, superelastic materials, polymers, and the like. In one nonlimiting example, first component 210 and third component 211 each may include a NITINOL alloy having an Af that is sufficiently below body temperature that the material is in an austenitic, superelastic phase while in the human body in a manner such as described with reference to FIGS. 1A-1E. Second component 220 may include a NITINOL alloy having an austenitic phase transition temperature Af that is slightly above body temperature such that the material remains in its martensitic, shape-memory phase while in the body unless and until it is heated to its Af, for example by the injection of warm or hot saline into the fluid within or flowing through second component 220 or the application of RF energy, or the use of a laser, magnetic inductance, electrical resistance, or the like in a manner such as described with reference to FIGS. 1A-1E. Alternatively, device 200 may include a single NITINOL alloy that has been heat treated to produce a lower Af in regions respectively corresponding to first component 210 and third component 211, and that has been heat treated to produce a higher Af in a region corresponding to second component 220. The malleable shape-memory material of second component 220 may be expandable and contractible using any suitable technique, e.g., such as described with reference to FIGS. 1A-1E. First component 210, second component 220, and third component 211 optionally may be integrally formed from a common frame with one another in a manner such as described with reference to FIGS. 1A-1E.

In a manner such as described in greater detail with reference to FIGS. 7-12B and 15A-15D, first component 210 may provide an inlet, second component 220 may provide a neck, and third component 211 may provide an outlet coupled, e.g., fluidically coupled, to the inlet via the neck. As used herein, "inlet" means component with ingress of blood flow, and "outlet" means component with outgress (egress) of blood flow. The particular components that respectively may be used to provide ingress and outgress (egress) of blood flow may be selected based on the condition being treated. For example, in HF, the inlet may be on the left atrial (LA) side, where blood flow from LA to right atrium (RA), and LA decompression, are desirable. In contradistinction, in PAH, the interatrial pressure gradient is reversed causing R to L flow and RA decompression, and the inlet is on the RA side. The cross sectional area of the neck may be smaller than the cross sectional areas of at least one of the inlet and the outlet, for example as described in greater detail with reference to FIGS. 7-12B. Or, for example, the cross sectional area of the neck may be larger than respective cross sectional areas of at least one of the inlet and the outlet, for example as described in greater detail with reference to FIGS. 15A-15B. Third component 211 may be configured to engage an opening in the human body, for example in a manner such as described with reference to FIGS. 7-12B. Additionally, or alternatively, first component 210 may be configured to engage a lumen in the body, for example in a manner such as described with reference to FIGS. 15A-15D. Optionally, third component 211 may be configured to engage a lumen in the body, for example in a manner such as described with reference to FIGS. 15A-15D. Illustratively, the lumen may include a blood vessel, and the first and third components may be configured to engage the blood vessel. The neck, if present, optionally may be configured to be disposed adjacent to an ostium of the blood vessel, e.g., in a manner such as described with reference to FIGS. 15A-15D.

FIGS. 3A-3D schematically illustrate an example device with multiple internal dimensions that can be reduced and increased in vivo. Device 300 illustrated in FIGS. 3A-3D includes first component 310, second component 320, and third component 321 which is coupled, e.g., fluidically coupled, to first component 310 and second component 320. First component 310 may include a self-expanding superelastic material, second component 320 may include a first malleable shape-memory material, and third component 321 may include a second malleable shape-memory material. The respective malleable shape-memory materials of second component 320 and third component 321 may have a first cross sectional area permitting a first rate of fluid flow through the second component, may be expandable to a second cross sectional area permitting a second rate of fluid flow through the second component, and may be contractible to a third cross sectional area permitting a third rate of fluid flow through the second component. Note that the cross sectional areas, sizes, and shapes of second component 320 and third component 321 may be, but need not necessarily be, the same as one another. Note that the overall rate of fluid flow through device 200 also may depend on the cross sectional areas of first component 210 and second component 211. Illustratively, in examples where the cross sectional area of second component 320 is smaller than that of third component 321, or where the cross sectional area of second component 320 is larger than that of third component 321, the smaller of the cross sectional areas may define the rate of fluid flow through device 300.

Figure 14A:
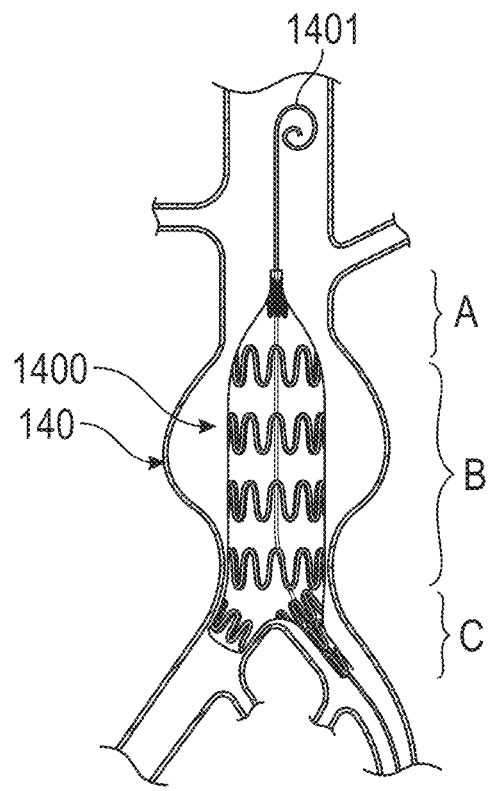
FIGS. 14A-14C schematically illustrate another example device with multiple internal dimensions that can be reduced and increased in vivo, and an example of its use in the human body.
Figure 14B:
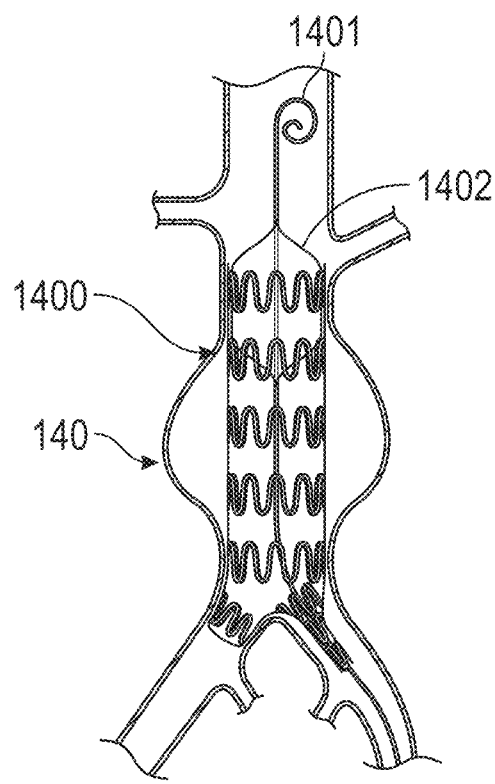
Figure 14C:
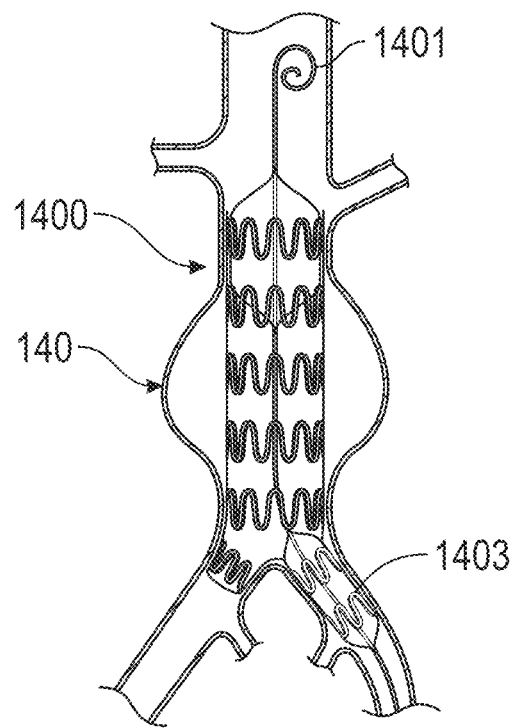

In addition to defining the rate of fluid flow through device 300, examples such as described with reference to FIGS. 3A-3D may allow for controllably adjusting apposition for anchoring or fixating the device to the wall of a body space by balloon expansion of apposing components 320, 321, e.g., in a manner such as described with reference to FIGS. 14A-14C, while allowing these apposing components to be contracted so that the device may be repositioned after deployment. Additionally, or alternatively, examples such as described with reference to FIGS. 3A-3D may provide for a relatively safe method of implantation as compared, for example, to expanding the first, second, and third components 310, 320, 321 all together with one another. For example, in an implementation such as described with reference to FIGS. 14A-14C, expanding the first, second, and third components 310, 320, 321 all together with one another may cause blockage of the branch arteries. Allowing for selective expansion of specific segments in a more gradual manner can be safer.

Figure 3A:
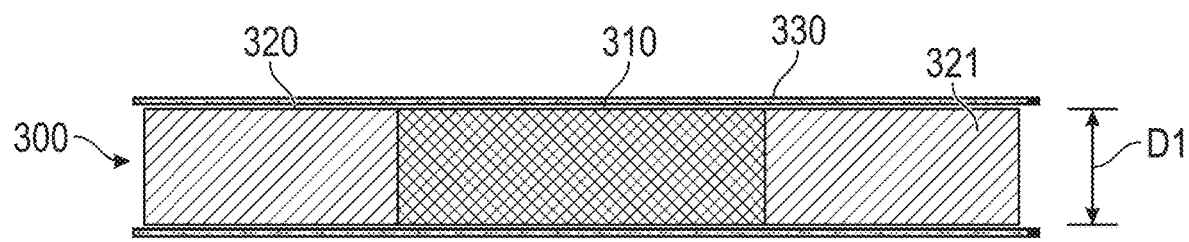
FIGS. 3A-3D schematically illustrate an example device with multiple internal dimensions that can be reduced and increased in vivo.
Figure 3B:
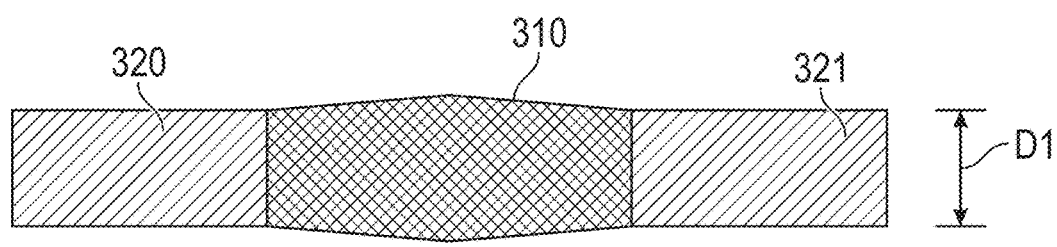
Figure 3C:
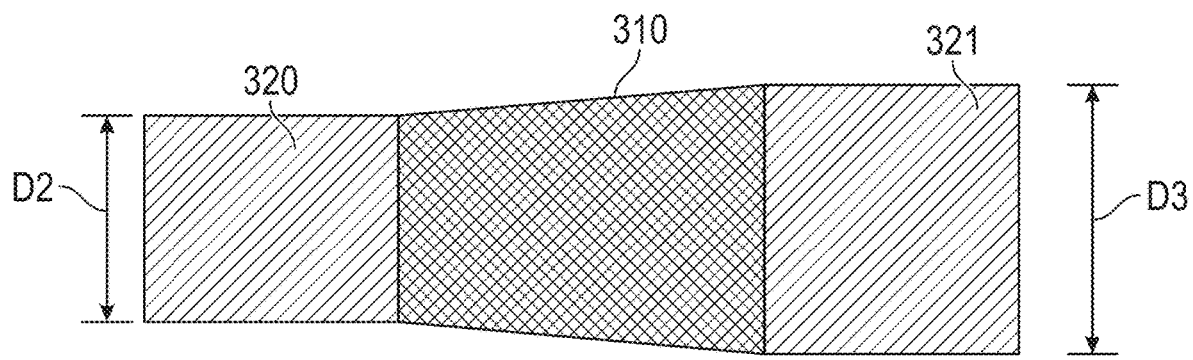

FIG. 3A schematically illustrates device 300 in a crimped state and loaded into sheath 330 for percutaneous implantation within the human body. In the crimped state, first component 310, second component 320, and third component 321 may have a dimension D1 (corresponding to a first cross sectional area). Once device 300 is delivered to the desired location, sheath 330 may be retracted so as to percutaneously implant the device. As illustrated in FIG. 3B, following removal of sheath 330 the self-expanding superelastic material of first component 310 may automatically expand, while the first malleable shape-memory material of second component 320 and the second malleable shape-memory material of third component 321 may remain in the crimped state (e.g., at the first cross sectional area) until they are further adjusted. Second component 320 and third component 321 independently may be expanded by any suitable amount, for example such as shown in FIG. 3C, to respective dimensions D2 (corresponding to a second cross sectional area) and D3. Second component 320 and third component 321 independently may be reduced to their respective heat-set dimensions and then expanded by any suitable amount, for example such as shown in FIG. 3D, to respective dimensions D4 (corresponding to a third cross sectional area) and D5.

Based on the particular dimensions (and cross sectional areas) to which second component 320 and third component 321 independently are adjusted by expansion or contraction, different rates of fluid flow may be permitted through such components, thus providing an adjustable orifice for controlling the flow of fluid within the location of the human body in which device 300 is deployed. Although FIGS. 3A-3D illustrate exemplary dimensions D1, D2, D3, D4, and D5 to which second component 320 and third component 321 independently may be set, it should be appreciated that any suitable dimension(s) may be obtained by independently expanding or contracting the second component and third components as desired. For example, second component 320 and third component 321 may have respective heat-set dimensions D0 that may be the same as, or different than, one another, and may be crimped to dimension D1 which is smaller than D0. Second component 320 and third component 321 respectively may be expanded to any suitable dimension(s), reset to D0, and subsequently re-expanded to any suitable dimension(s) any suitable number of times.

Figure 3D:
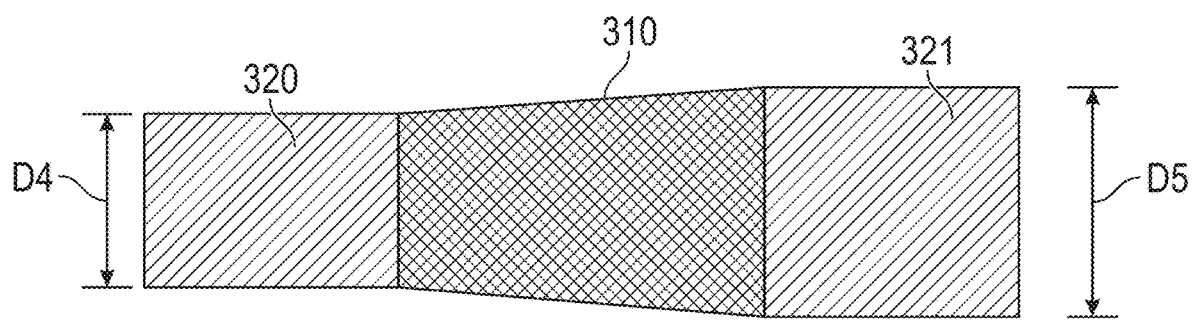

In the nonlimiting examples shown in FIGS. 3B and 3D, the respective interfaces between the crimped state of second component 320 and third component 321 and expanded first component 310 may apply forces that inhibit first component 310 from fully expanding; it should be appreciated that such interfaces instead may apply respective forces that cause second component 320 or third component 321 to partially expand. As described in greater detail below, the particular manner in which first component 310, second component 320, and third component 321 respectively are joined to one another may be selected so as to control the force(s) applied to such components and thus the shapes and dimensions of such components.

In some examples, the self-expanding superelastic material of first component 310, the first malleable shape-memory material of second component 320, and the second malleable shape-memory material of third component 321 may include different materials than one another, or may include the same material as one another but having different phases than one another. For example, first component 310, second component 320, and third component 321 independently may include one or more materials selected from the group consisting of nickel titanium (NiTi), also known as NITINOL, other shape memory alloys, self-expanding materials, superelastic materials, polymers, and the like. In one nonlimiting example, first component 310 may include a NITINOL alloy having an Af that is sufficiently below body temperature that the material is in an austenitic, superelastic phase while in the human body in a manner such as described with reference to FIGS. 1A-1E. Second component 320 and third component 321 each may include a NITINOL alloy having an austenitic phase transition temperature Af that is slightly above body temperature such that the material remains in its martensitic, shape-memory phase while in the body unless and until it is heated to its Af, for example by the respective injection of warm or hot saline into the fluid within or flowing through second component 320 or third component 321 or the application of RF energy, or the use of a laser, magnetic inductance, electrical resistance, or the like in a manner such as described with reference to FIGS. 1A-1E. Alternatively, device 300 may include a single NITINOL alloy that has been heat treated to produce a lower Af in a region corresponding to first component 310, and that has been heat treated to produce a higher Af in regions respectively corresponding to second component 320 and third component 321. Second component 320 and third component 321 may, but need not necessarily, have the same material or the same Af as one another. The respective malleable shape-memory materials of second component 320 and third component 321 may be independently expandable relative to one another using any suitable technique, e.g., such as described with reference to FIGS. 1A-1E, may be reset to their respective heat-set dimensions, and then independently re-expanded to respective dimensions. First component 310, second component 320, and third component 321 optionally may be integrally formed from a common frame with one another in a manner such as described with reference to FIGS. 1A-1E.

In a manner such as described in greater detail with reference to FIGS. 14A-14C, the cross sectional areas of second component 320 and third component 321 may be expanded independently from one another so as to fixate the device within the lumen while allowing for repositioning. In examples such as described in greater detail with reference to FIGS. 14A-14C, second component 320 may be configured as an inlet, and third component 321 may be configured as an outlet fluidically coupled to the inlet via first component 310. The inlet 320 may be configured to engage a blood vessel in the human body, and the outlet 321 may be configured to extend into ostium of the blood vessel in a manner such as described with reference to FIGS. 14A-14C.

A fourth component may be fluidically coupled to first component 310 and configured to extend into another ostium of the blood vessel, for example in a manner such as described with reference to FIGS. 14A-14C. In some example, first component 310 may be configured to provide a fluidic pathway for blood flow, for example, to channel blood flow past the weak segment of an aneurism, such as an aortic aneurism. In order to effectively protect the aneurism from the stress of aortic pressure, the inlet 320, outlet 321, and fourth component may be expanded so as to form sufficiently tight seals with their respective blood vessel(s).

In the present devices, such as exemplified by devices 100, 200, 300 respectively described with reference to FIGS. 1A-1E, 2A-2E, and 3A-3D, the first, second, and (if present) third components may be coupled, e.g., fluidically coupled, to one another using any suitable manner(s) of joining. For example, any malleable shape-memory material (such as in component 120, 220, 320, or 321) optionally and independently may be joined to any self-expanding superelastic material (such as in component 110, 210, 211, or 310) by welding. Additionally, or alternatively, any malleable shape-memory material (such as in component 120, 220, 320, or 321) optionally and independently may be joined to any self-expanding superelastic material (such as in component 110, 210, 211, or 310) using an encapsulant which may cover at least a portion of at least one of the components, and which may join such components to one another. Additionally, or alternatively, any shape-memory material and any self-expanding superelastic material may be integrally formed from a common frame with one another.

Figure 4A:
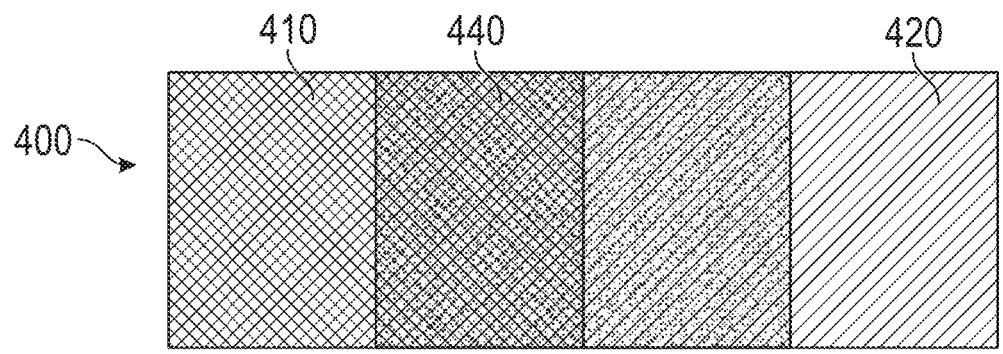
FIGS. 4A-4B schematically illustrate example encapsulants that may be provided in a device with an internal dimension that can be reduced and increased in vivo.
Figure 4B:
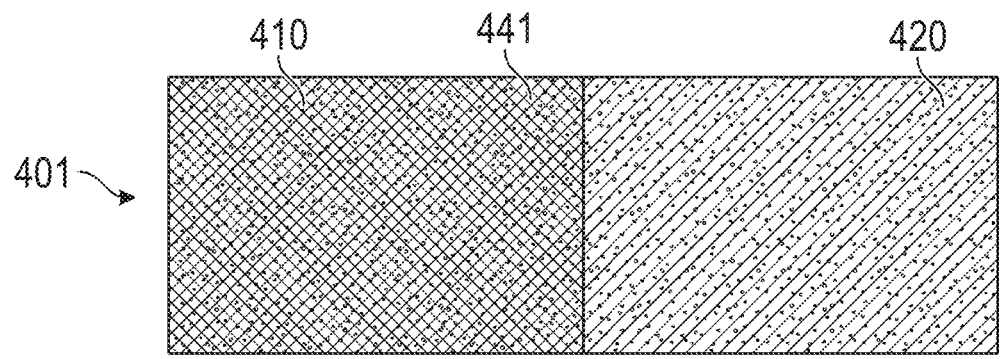

For example, FIGS. 4A-4B schematically illustrate example encapsulants that may be provided in a device with an internal dimension that can be reduced and increased in vivo. In example device 400 illustrated in FIG. 4A, which may include any suitable number of components (only two components illustrated for simplicity), encapsulant 440 covers a portion of each of first component 410 and second component 420, which components may be configured similarly as described with reference to FIGS. 1A-1E, 2A-2E, or 3A-3D. Encapsulant 440 may fluidically join the malleable shape-memory material (e.g., of component 420) to the self-expanding superelastic material (e.g., of component 410). Optionally, encapsulant 440 indirectly and elastically joins the malleable shape-memory material to the self-expanding superelastic material. In example device 401 illustrated in FIG. 4B, which may include any suitable number of components (only two components illustrated for simplicity), encapsulant 441 covers the entirety of each of first component 410 and second component 420, which components may be configured similarly as described with reference to FIGS. 1A-1E, 2A-2E, or 3A-3D. Encapsulants 440 or 441 may fluidically join the malleable shape-memory material (e.g., of component 420) to the self-expanding superelastic material (e.g., of component 410). It will be appreciated that in other examples (not specifically illustrated), an encapsulant may entirely cover one or more components, and may only partially cover one or more other components. The encapsulant may indirectly couple one or more components to one another. A combination of encapsulation and mechanically engaging, e.g., welding or mechanical interference, may be used to both directly and indirectly couple the present components to one another.

Encapsulants 440, 441 may include any suitable biocompatible material, such as a polymer or a natural material. Examples of polymers suitable for use as an encapsulant include expanded polytetrafluoroethylene (ePTFE), silicone, polycarbonate urethane, DACRON (polyethylene terephthalate), Ultra High Molecular Weight Polyethylene (UHMWPE), and polyurethane. Examples of natural materials suitable for use as an encapsulant include pericardial tissue, e.g., from an equine, bovine, or porcine source, or human tissue such as human placenta or other human tissues. The biocompatible material is preferably smooth so as to inhibit thrombus formation, and optionally may be impregnated with carbon so as to promote tissue ingrowth. Alternatively, to promote tissue ingrowth and endothelization, the biocompatible material may form a mesh-like structure. The present devices may be encapsulated with a biocompatible material in a manner similar to that described in U.S. Patent Publication No. 2019/0110911 to Nae et al., entitled "Systems and Methods for Making Encapsulated Hourglass Shaped Stents," the entire contents of which are incorporated by reference herein. For example, an inner surface of one of the present devices may be covered with a first graft layer, and an outer surface of the device may be covered with a second graft layer. The graft layers may be securely bonded together to form a monolithic layer of biocompatible material, e.g., may be sintered together to form a strong, smooth, substantially continuous coating that covers the inner and outer surfaces of the device. Portions of the coating then may be removed as desired from selected portions of the device using laser-cutting or mechanical cutting, for example.

In one example, the device is encapsulated with ePTFE. It will be understood by those skilled in the art that ePTFE materials have a characteristic microstructure consisting of nodes and fibrils, with the fibrils orientation being substantially parallel to the axis of longitudinal expansion. Expanded polytetrafluoroethylene materials may be made by ram extruding a compressed billet of particulate polytetrafluoroethylene and extrusion lubricant through an extrusion die to form sheet or tubular extrudates. The extrudate is then longitudinally expanded to form the node-fibril microstructure and heated to a temperature at or above the crystalline melt point of polytetrafluoroethylene, i.e., 327° C., for a period of time sufficient to sinter the ePTFE material. Heating may take place in a vacuum chamber to prevent or inhibit oxidation of the device. Alternatively, heating may take place in a nitrogen rich environment. A furnace may be used to heat the encapsulated device. Alternatively, or additionally, a mandrel upon which the encapsulated device rests may be used to heat the encapsulated device.

Figure 5A:
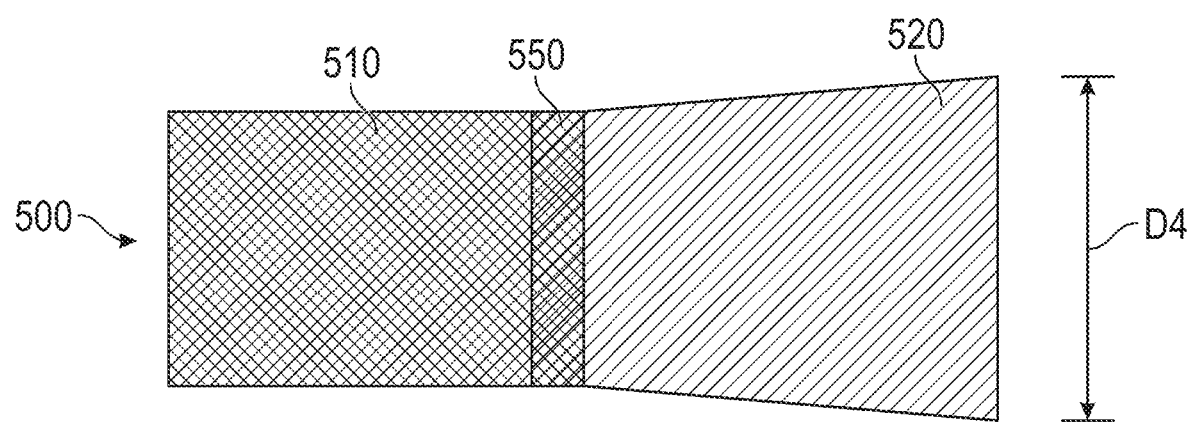
FIGS. 5A-5B schematically illustrate example arrangements of components in a device with an internal dimension that can be reduced and increased in vivo.
Figure 5B:
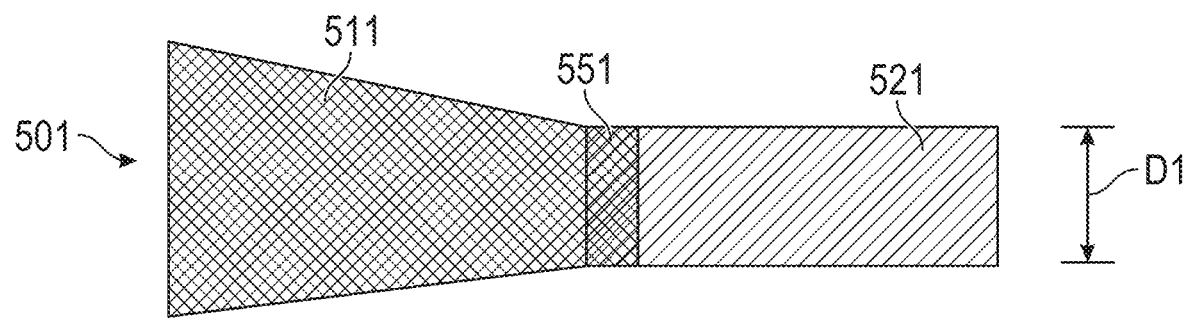

In addition to, or as an alternative to, any other method of joining components of the present device to one another, one or more of the components may be fully or partially inserted into another one or more of the components. For example, FIGS. 5A-5B schematically illustrate example arrangements of components in a device with an internal dimension that can be reduced and increased in vivo. In example device 500 illustrated in FIG. 5A, which may include any suitable number of components (only two components illustrated for simplicity), second component 520 is at least partially located inside of first component 510, which components may be configured similarly as described with reference to FIGS. 1A-1E, 2A-2E, or 3A-3D. Overlap region 550 between first component 510 and second component 520, which region optionally may extend for the entire length of one or both of first component 510 and second component 520, may join the malleable shape-memory material (e.g., of component 520) to the self-expanding superelastic material (e.g., of component 510). For example, the outer surface of second component 520 may engage with (e.g., mechanically interfere with) the inner surface of first component 510 in such a manner as to inhibit lateral motion of the two components relative to one another. Additionally, the dimension of first component 510 may constrain expansion of second component 520 beyond that dimension within overlap region 550, e.g., may apply a force that inhibits second component 520 from fully expanding. As such, even if second component 520 is expanded (e.g., mechanically), the dimension of first component 510 may inhibit the second component from entirely expanding to a larger dimension.

In example device 501 illustrated in FIG. 5B, which may include any suitable number of components (only two components illustrated for simplicity), first component 511 is at least partially located inside of second component 521, which components may be configured similarly as described with reference to FIGS. 1A-1E, 2A-2E, or 3A-3D. Overlap region 551 between first component 511 and second component 521, which region optionally may extend for the entire length of one or both of first component 511 and second component 521, may join the malleable shape-memory material (e.g., of component 521) to the self-expanding superelastic material (e.g., of component 511). For example, the inner surface of second component 521 may engage with (e.g., mechanically interfere with) the outer surface of first component 511 in such a manner as to inhibit lateral motion of the two components relative to one another. Additionally, the dimension of second component 521 may constrain expansion of first component 511 beyond that dimension within overlap region 551, e.g., may apply a force that inhibits first component 511 from fully expanding. As such, even if first component 511 is expanded (e.g., self-expands), the dimension of second component 521 may inhibit the first component from entirely expanding to a larger dimension.

Mechanical interference between components, e.g., such as described with reference to FIGS. 5A-5B, may inhibit recoil of the shape memory component. For example, a known problem with martensitic NITINOL stents is recoil, in which about 10-15% diameter shrinkage may make apposition to a vascular wall challenging. Mechanical interference between device components, e.g., concentric coupling such as illustrated in FIGS. 5A-5B, may reduce or inhibit such recoil. For example, in the configuration described with reference to FIG. 5B, first component 511 may physically inhibit second component 521 from recoiling. In some configurations, the respective hoop strengths of the first and second components may be approximately balanced with one another, optionally with the shape-memory martensitic component being slightly stronger, so as to reduce or minimize recoil.

Figure 6:
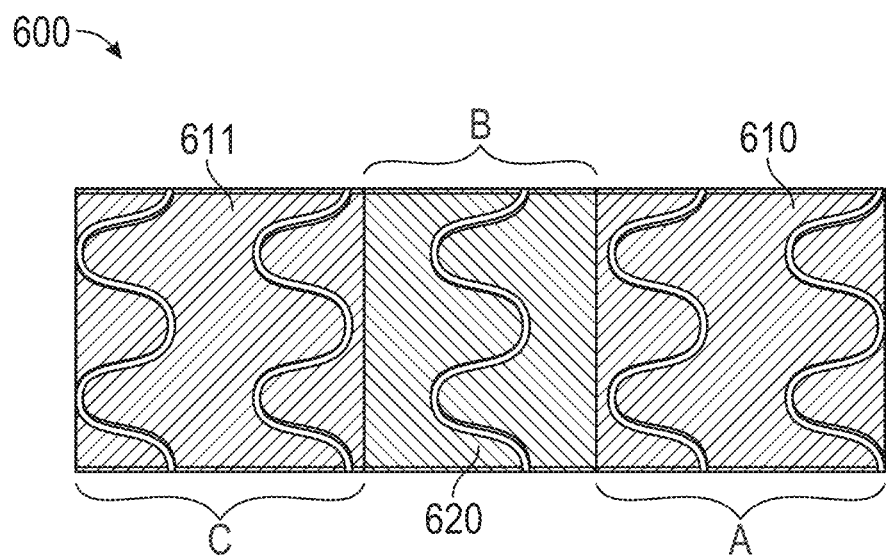
FIG. 6 schematically illustrates another example device with an internal dimension that can be reduced and increased in vivo.

It will be appreciated that devices such as described with reference to FIGS. 1A-1E, 2A-2E, 3A-3D, and options thereof such as described with reference to FIGS. 4A-4B and 5A-5B, may have any suitable configuration. For example, FIG. 6 schematically illustrates another example device 600 with an internal dimension that can be reduced and increased in vivo. Device 600 includes first component 610 (also designated "A"), second component 620 (also designated "B"), and third component 611 (also designated "C"). Device 600 optionally may include a tube of material that is laser-cut to define a plurality of struts and connecting members, e.g., a plurality of sinusoidal rings connected by longitudinally extending struts (struts not specifically illustrated). The sinusoidal rings illustrated in FIG. 6 may be laser cut to form an integral piece of unitary construction, and different regions of the piece may be heat treated differently than one another to produce components having different Afs than one another in a manner such as described elsewhere herein. Alternatively, the sinusoidal rings of first component 610, second component 620, and third component 611 may be separately defined to form different pieces of material with suitable Afs that are subsequently coupled together to form device 600. Device 600 may also be electropolished to reduce thrombogenicity.

Optionally, the Af of first component 610 and the Af of third component 611 each may be greater than the Af of second component 620. For example, first component 610 may correspond to first component 210 described with reference to FIGS. 2A-2E and may include a first self-expanding superelastic material, second component 620 may correspond to second component 220 and may include a malleable shape-memory material, and third component 611 may correspond to third component 211 and may include a second self-expanding superelastic material. As another option, the Af of first component 610 and the Af of third component 611 may be less than the Af of second component 620. For example, first component 610 may correspond to first component 310 described with reference to FIGS. 3A-3D and may include a self-expanding superelastic material, second component 620 may correspond to second component 320 and may include a first malleable shape-memory material, and third component 611 may correspond to third component 321 and may include a second malleable shape-memory material. Optionally, the Af of first component 610 and the Af of third component 611 may be the same as one another.

It will be appreciated that the present devices may be percutaneously implanted within any suitable portion of the human body, such as a body lumen (e.g., a blood vessel) or the heart. Similarly, it will be appreciated that the present devices suitably may be adjusted in vivo, after implantation, in such a manner as to adjust the flow of fluid in such a manner as to treat or ameliorate any suitable condition such as HF, PAH, aneurism, aortic valve stenosis, mitral valve stenosis, or to improve outcomes following cardiac valve repair (e.g., mitral valve repair) or following cardiac ablation (e.g., for treating atrial fibrillation). Some nonlimiting examples of devices for implantation at selected locations are described with reference to FIGS. 7-16B.

In some examples, the present devices may be or include hourglass or "diabolo" shaped shunts, which optionally are encapsulated with biocompatible material, and which may be used for treating subjects suffering from disorders for which regulating fluid flow may be useful, such as CHF or PAH. In some examples, the hourglass shaped shunts may be specifically configured to be lodged securely in the atrial septum, for example in an opening through the fossa ovalis, to allow blood flow from the left atrium to the right when blood pressure in the left atrium exceeds that of the right atrium, or blood flow from the right atrium to the left when blood pressure in the right atrium exceeds that of the left atrium. As provided herein and described in greater detail with reference to FIGS. 7-10C, the internal dimension of the hourglass shaped shunt suitably may be adjusted in vivo, for example, so as to adjust the flow of fluid therethrough, e.g., so as to adjust the flow of fluid between the left atrium and the right atrium through the atrial septum.

Figure 7:
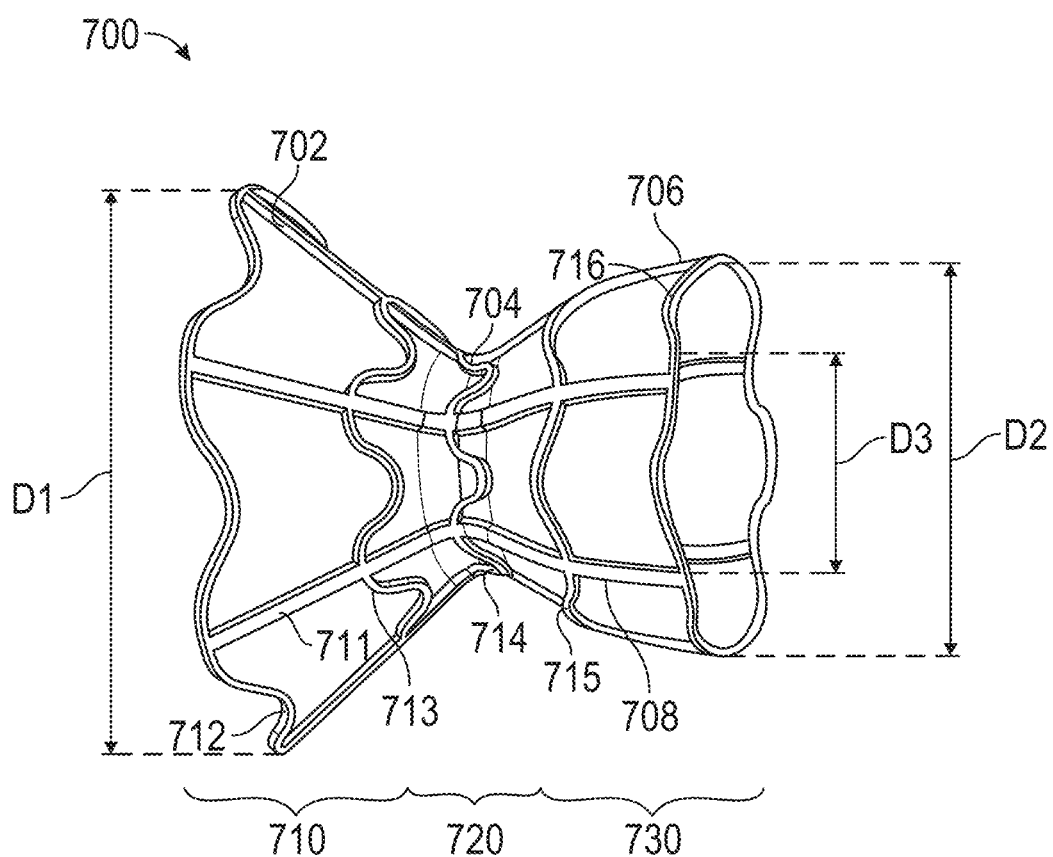
FIG. 7 schematically illustrates another example device with an internal dimension that can be reduced and increased in vivo.

Referring now to FIG. 7, shunt 700 is illustrated that has an internal dimension that can be reduced and increased in vivo. Shunt 700 is hourglass or "diabolo" shaped and may include first component 710, second component 720, and third component 730 which are fluidically coupled to one another. First component 710 may include a first self-expanding superelastic material, second component 720 may include a malleable shape-memory material, and third component 730 may include a second self-expanding superelastic material, in a manner similar to that described with reference to FIGS. 2A-2E. First component 710 may include any suitable number of rings, e.g., rings 712, 713, which are formed of or include the first self-expanding material, and which optionally may be sinusoidal. Second component 720 may include any suitable number of rings, e.g., ring 714, which is formed of or includes the malleable shape-memory material, and which optionally may be sinusoidal. Third component 730 may include any suitable number of rings, e.g., rings 715, 716, which are formed of or include the third self-expanding material, and which optionally may be sinusoidal. Struts 711, 708 may join the rings of first component 710, second component 720, and third component 730 to one another.

First component 710 may provide a first flared end region 702, third component 730 may provide a second end flared region 706, and second component 720 may provide a neck region 704 disposed between the first and second flared end regions. In the nonlimiting example shown in FIG. 7, first flared end region 702 has first end region dimension D1, second flared end region 706 has second end region dimension D2, and neck region 704 has neck dimension D3 which may be increased or reduced in a manner such as described with reference to second component 220 illustrated in FIGS. 2A-2E. As shown in FIG. 7, neck region 704 of shunt 700 may be significantly narrower than flared end regions 702 and 706, e.g., may have a smaller cross sectional area and a smaller dimension than do flared end regions 702 and 706. Also shown in FIG. 7, shunt 700 may be asymmetric. For example, shunt 700 may be asymmetric to take advantage of the natural features of the atrial septum of the heart as well as the left and right atrium cavities. Alternatively, hourglass shaped shunt 700 may be symmetric with the first end region dimension D1 being equal to the second end region dimension D2. First flared end region 702 and second flared end region 706 also may have either straight or curved profiles or both. For example, strut 711 has a straight profile and strut 708 has a curved profile. Additionally, first flared end region 702 and second flared end region 706 may assume any angular position consistent with the hour-glass configuration.

Shunt 700 suitably may be formed in a manner such as described elsewhere herein. For example, in some configurations, shunt 700 is laser-cut from a single tube of NITINOL in a manner such as described with reference to device 600 illustrated in FIG. 6, and different regions of the NITINOL are heat treated differently than one another so as respectively to define self-expanding superelastic material(s) and malleable shape-memory materials. As such, the first, second, and third components 710, 720, 730 of device 700 optionally may be unitary with one another. The first and third self-expanding materials optionally may be the same material as one another. In other configurations, the first, second, and third components 710, 720, 730 of device 700 may be formed independently of one another and assembled together, e.g., in a manner such as described with reference to FIGS. 5A-5B and as further exemplified with reference to FIGS. 11A-12B, described below. Additional optional modifications of shunt 700 are described with reference to FIGS. 13A-13B, described below.

Figure 8A:
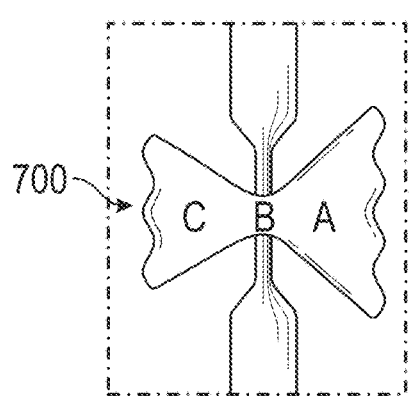
FIGS. 8A-8D schematically illustrate example steps for using the device of FIG. 7 in the human body.

FIGS. 8A-8D schematically illustrate example steps for using the device of FIG. 7 in the human body. Shunt 700 may be crimped to a cylindrical shape, for example by pushing it through a conical loading device. In one nonlimiting example, shunt 700 may be crimped to an outer dimension of about 4.6 mm, the inside dimension of a 14F Cook sheath. The sheath may be percutaneously placed through a blood vessel to a desired location in the human body, and the crimped shunt may be placed in the sheath in a manner similar to that illustrated in FIG. 2A. As the crimped shunt is pushed out of the sheath, the self-expanding superelastic flared end regions spring open to their set configuration, while the malleable shape-memory central neck region remains constrained at or near its crimped dimension, e.g., in a manner such as illustrated in FIG. 8A in which the neck region (designated "B" and corresponding to second component 220) engages an opening in the human body. Depending on the desired direction of blood flow through device 700, one of the flared ends (designated "A" or "C" and corresponding to first component 210 or third component 211) provides an inlet and the other of the flared ends (designated "C" or "A" and corresponding to third component 211 or first component 210) provides an outlet. For example, the neck region may engage an opening created through a fossa ovalis of an interatrial septum between a right atrium and a left atrium, one of the flared ends extends into the right atrium, and the other flared end extends into the left atrium. In some configurations, the flared end in the right atrium is an inlet and the flared end in the left atrium is an outlet, whereas in other configurations, the flared end in the left atrium is an inlet and the flared end in the right atrium is an outlet.

Figure 8B:
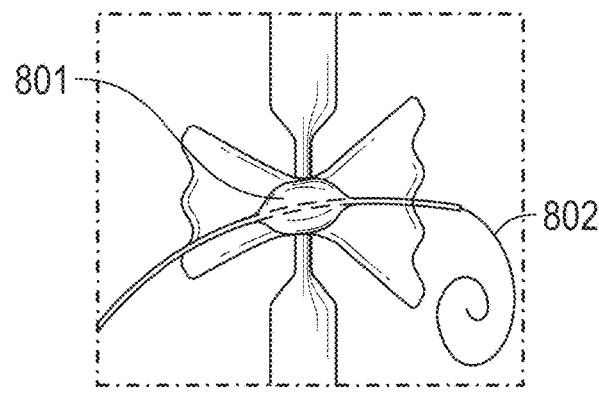
Figure 8C:
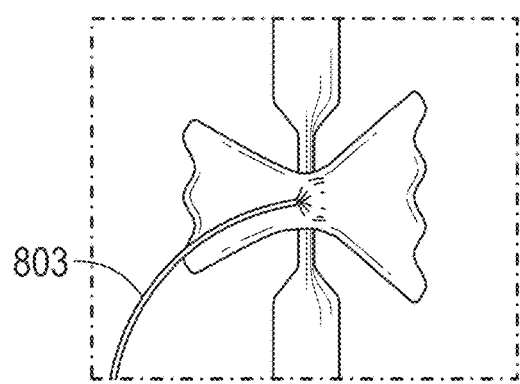
Figure 8D:
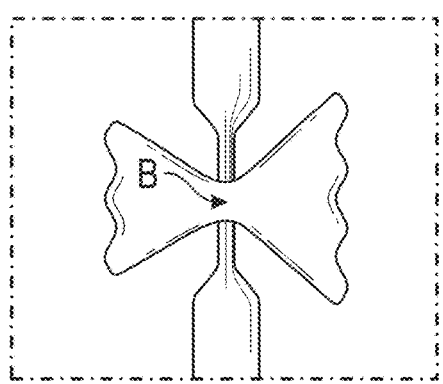

The cross sectional area (and dimension) of the orifice provided by the malleable shape-memory central neck region may be increased or reduced so as to adjust the flow of fluid through shunt 700. For example, in a manner such as illustrated in FIG. 8B, the neck region may be expanded by balloon dilatation using a balloon 801, which may be fed through the orifice using a wire 802. Additionally, in a manner such as illustrated in FIG. 8C, the neck region may be contracted by injecting, via catheter 803, a bolus of hot saline having a temperature above the Af of the malleable shape-memory material (e.g., at 45-60° C.), which may cause the neck region to return to its heat-set dimension, which may be different from its crimped dimension, in a manner such as illustrated in FIG. 8D.

For example, heat from the saline may cause the malleable shape-memory material to transition to an austenitic phase, compressing the neck region back to its crimped (or otherwise heat set) dimension, following which the neck region cools to body temperature and transitions back to its martensitic phase. The saline may be delivered in any suitable manner, for example by a flexible catheter having one or more apertures (e.g., one side hole or multiple side-holes) through which hot saline may flow and that may be placed within the neck region, for example, over a guidewire through the neck region. In one nonlimiting example, the neck region may have its crimped inner dimension, typically 1-2 mm, at a first time, such as when initially deployed in a manner such as illustrated in FIG. 8A. The neck region then may be expanded using balloon dilatation to any desired larger dimension between the crimped dimension and 7 mm at a second time. The neck region then may be contracted using hot saline to its heat-set dimension, D0, at a third time. Dimension D0 is determined by the size of the jig used in a heat-setting step during manufacture. D0 may be greater than the dimension of the catheter used to deliver hot saline, and greater than the deflated dimension of the dilation balloon, but smaller than or equal to the smallest anticipated desired final shunt dimension, for example 4 mm. The neck region then again may be expanded using balloon dilatation to any desired larger dimension between 4 mm and 7 mm at a second time. Any suitable number of expansions and contractions may be applied to the neck region, at any desired time or at separate times than one another, so as to provide a suitable, and customized, flow of fluid through the device for each given patient. It will be appreciated that what constitutes a suitable flow of fluid for a given patient also may change over time, and that the present devices suitably may be adjusted—so as to provide that flow of fluid as appropriate, or so as to suitably fixate the devices within a lumen. It will also be appreciated that the self-expanding superelastic components are not affected by the injection of hot saline, and so will retain their initial full expanded dimension while the shape-memory component (in this example the neck region) is being adjusted. Furthermore, any suitable method for heating the shape memory materials may be used besides or in addition to hot saline, e.g., RF heating or the use of a laser, magnetic inductance, electrical resistance, or the like in a manner such as described with reference to FIGS. 1A-1E.

Figure 9A:
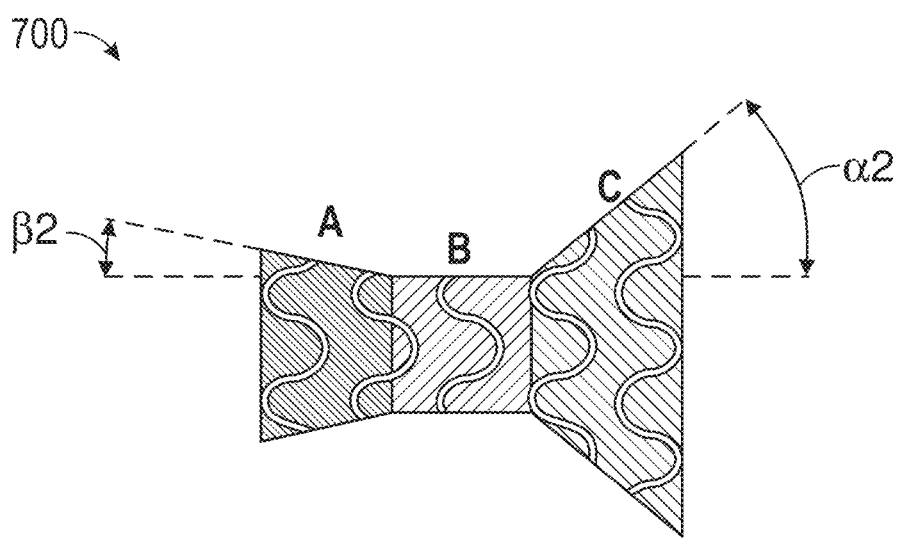
FIGS. 9A-9B schematically illustrate example configurations of the device of FIG. 7.
Figure 9B:
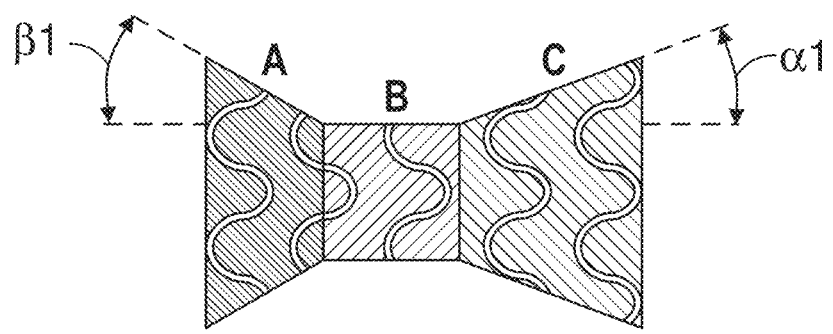

The particular configuration of shunt 700 may be selected so as to provide desired flow dynamics therethrough. For example, FIGS. 9A-9B schematically illustrate example configurations of the device of FIG. 7. In FIGS. 9A-9B, the geometry of the inlet and outlet inner dimensions (e.g., the inlet and outlet angles $\alpha$ and $\beta$) may be selected so as to adjust the flow dynamics through shunt 700. Apart from adjusting the flow dynamics so as to treat a specific clinical condition, the capability to narrow the inlet or outlet, or both, may reduce the risk of passage of thrombus into or through the device lumen.

Figure 10A:
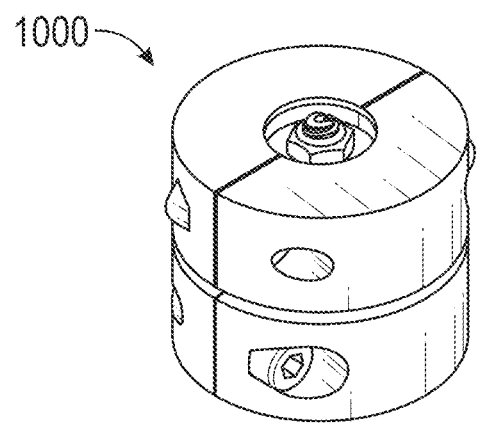
FIGS. 10A-10C schematically illustrate example uses of tooling for preparing the device of FIG. 7.
Figure 10B:
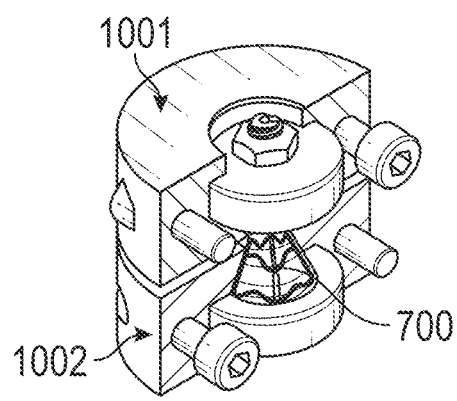
Figure 10C:
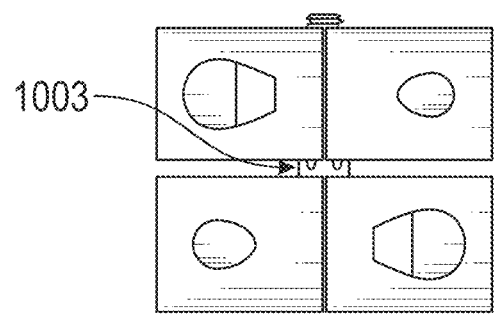

Shunt 700 (or any other device provided herein) may be made using any suitable combination of techniques. FIGS. 10A-10C schematically illustrate example uses of tooling for preparing the device of FIG. 7. As shown in FIGS. 10A-10C, the shunt 700 (or any other device provided herein) may be heat treated within tooling 1000 which allows for the component(s) which are to be substantially self-expanding superelastic material to be maintained at a cooler temperature (e.g., individually insulated or heat-sinked by dies 1001, 1002 within the tooling) than the component(s) which are to be substantially malleable shape-memory material, e.g., which may be exposed such as at region 1003 illustrated in FIG. 10C. As such, the exposed component(s) may receive a greater heat flux during the heat treatment which may result in a predetermined higher Af temperature as compared to component(s) that are insulated or kept cooler by contact with a heat sink. The temperature gradient between the heated and cooled regions may result in a transition zone between a region that is substantially martensitic at body temperature (37° C.) and a region that is substantially austenitic at body temperature. The heat treatment may be implemented by a furnace, induction heating, an electrical current, or any other suitable and controllable energy source. The difference in heat flux (which may result in a higher Af for the component(s) which are to be substantially malleable shape-memory material) also may be achieved by providing that component with a different (lower) wall thickness, e.g., as may be achieved by material removal from a NITINOL tube prior to laser cutting or using an additive manufacturing process to manufacture the device.

Additionally, or alternatively, shunt 700 (or any other device provided herein) may be made using a multi-material additive manufacturing process. For example, the higher Af component(s) which are to be malleable shape-memory material may be provided by using selective laser melting or an electron beam melting powder bed machine which has two or more powder-bins between which the machine could switch during the print process. The Af of a given component may be manipulated by the powder's chemical composition, e.g., different fractions of nickel titanium or of any other element(s) that may be present. For example, the higher the nickel percentage, the higher the Af. The Af of a given component also or alternatively may be manipulated by the powder's physical composition, e.g., particle sizes. For example, the smaller the powder dimension, the lower the Af. For further details of manipulating the Af of materials during a multi-material additive manufacturing process, see Horvay and Schade, "Development of nitinol alloys for additive manufacturing," the entire contents of which are incorporated by reference herein. As another option, the multi-material may be achieved by liquid dispersion methodology (material jetting). For example, a 3-D printer may include two or more cartridges with different powder-liquid compositions in each, in a manner similar to that described for the powder-based example.

Figure 11A:
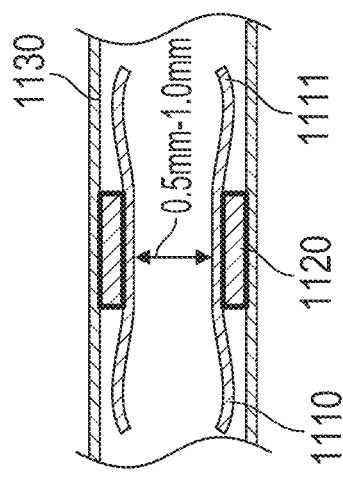
FIGS. 11A-11B schematically illustrate an example modification of the device of FIG. 7.
Figure 11B:
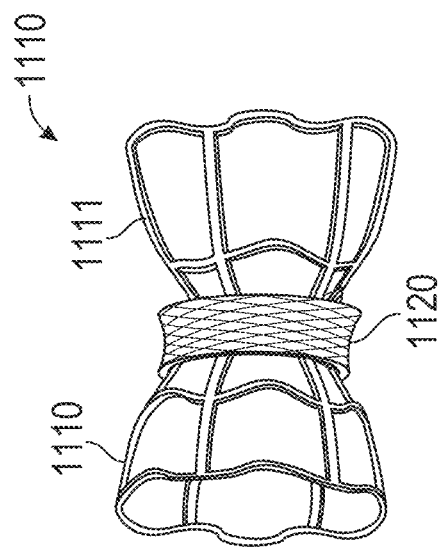

FIGS. 11A-11B schematically illustrate another example modification of the device of FIG. 7. In one specific, nonlimiting example, modified shunt 1100 includes an austenite phase (self-expanding superelastic) NITINOL inner frame and a martensite phase (malleable shape-memory) NITINOL outer frame. The inner frame may include first component 1110 (corresponding to first flared end region 702) and third component 1111 (corresponding to second flared end region 706). The outer frame may include second component 1120 (corresponding to neck region 704). The Af of the martensite outer frame may be in the range of 45–60° C., e.g., about 50-55° C. The outer frame may be localized to the shunt neck region (which may be, for example, approximately 5 mm in length) and may not extend to the atrial cones 1110, 1111. The inner and outer frames may be designed so that when placed together their respective geometries mechanically interfere so that they remain co-registered. The martensite outer frame may be heat set for a smaller inner dimension (e.g., 4 mm), while the austenite inner frame may be heat set for a larger orifice dimension (e.g., 7 mm). The inner and outer frames may be constructed such that the force required to expand the outer martensite frame is greater than that produced by the superelasticity of the inner frame, so that at any expanded dimension the martensitic outer frame is strong enough to contain the austenitic inner frame dimension, in a manner similar to that described with reference to FIG. 5B. At room temperature and at body temperature, the martensitic outer frame may be malleable and may be plastically deformed, e.g., by incremental balloon dilatation which may expand its inner dimension by any desired amount, illustratively in the range of 4-7 mm, depending on the balloon dimension and the expanding pressure, e.g., up to 12 atm. The martensitic outer frame may radially contact an outer surface of the neck of the austenitic inner frame so as to constrain the neck from self-expanding to a larger dimension. Responsive to the martensitic outer frame expanding to the larger dimension, the neck self-expands. The two co-registered frames may be encapsulated with ePTFE or other suitable biocompatible material so as to create a smooth path for blood flow and to block proliferating tissue ingress during healing after implantation. For example, the martensite outer frame, which may or may not be encapsulated, may be applied over an encapsulated inner frame, or the martensite outer frame may be applied to a bare inner frame and the two frames together then encapsulated. The encapsulant may form an inner lumen through a portion of the inner frame (e.g., through component 1110) and an outer covering of the device (e.g., of components 1110 and component 1120).

In an alternative configuration (not specifically illustrated), the martensitic frame including second component 1120 (corresponding to neck region 704) may be placed inside of the outer austenitic frame including first component 1110 (corresponding to first flared end region 702) and third component 1111 (corresponding to second flared end region 706). With proper mechanical interference, such as by laser spot welding interlocking shapes, the shorter martensitic frame may pull the center of the outer austenitic frame inward when heated above Af. For example, the martensitic inner frame may radially contact an inner surface of the neck so as to constrain the neck from contracting to a smaller dimension. The neck may self-contract responsive to the martensitic inner frame contracting to a smaller cross sectional area. An encapsulant may form an outer covering of first component 1110 and second component 1120.

Figure 12A:
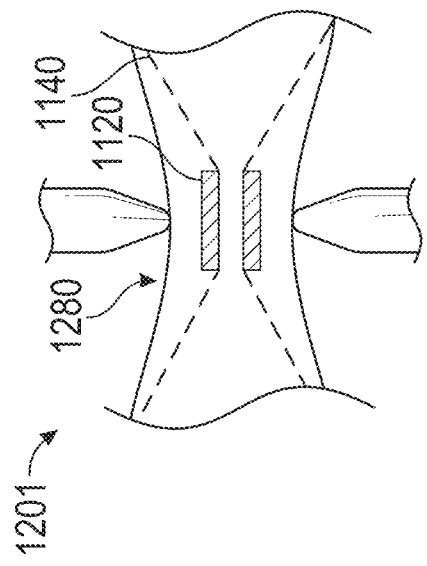
FIGS. 12A-12B schematically illustrate another example modification of the device of FIG. 7.
Figure 12B:
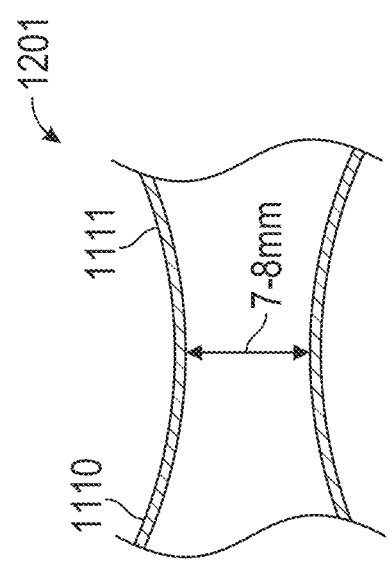

However, the martensitic frame need not necessarily be welded or otherwise directly coupled to the austenitic frame. For example, FIGS. 12A-12B schematically illustrate another example modification 1210 of the device of FIG. 7 in which the shorter martensitic frame 1120 (corresponding to neck region 704) is placed inside of the outer austenitic frame including first component 1110 (corresponding to first flared end region 702) and third component 1111 (corresponding to second flared end region 706) but is not directly coupled thereto. Instead, encapsulant 1140 encapsulates both inner martensitic frame 1120 and outer austenitic frame 1110, 1111 and indirectly and elastically couples the martensitic and austenitic frames to one another. In this example, the heat treatment for the neck of the superelastic outer frame may be heat set to the maximum dimension contemplated for treatment, e.g., 7 mm, rather than to the smallest such dimension as in the above two examples, e.g., 4 mm. Because there is no direct mechanical coupling between the superelastic outer austenitic frame and the shape-memory inner martensitic frame, when implanted in the body the outer frame may expand to the maximum dimension, e.g., 7 mm, or to a smaller dimension if constrained by the body (e.g., by opening 1280 through which the device is lodged). The hoop strength of the outer austenitic frame may be engineered so as to be slightly less than the constrictive force of the body opening 1280, such that the outer frame may maintain contact with opening 1280 without causing enough force to dilate the opening. The hoop strength of the outer austenitic frame may be adjusted, for example, by choosing a suitable frame tubing thickness and laser-cut frame pattern. The inner malleable shape-memory frame may be stronger than the outer frame and stronger than the compressive force of body opening 1280, so even if the inner frame is expanded to a dimension larger than the opening 1280 dimension of the outer frame as described above (e.g., to a dimension of 4-7 mm), it will maintain that dimension after the dilating balloon is deflated and removed.

Furthermore, because there is no direct attachment between the inner and outer frames in device 1210, the inner martensitic frame 1120 may returned to its original predilated dimension by application of heat in a manner such as described above, while leaving the outer frame constrained only by contact with opening 1280, as shown in FIG. 12B. Such a configuration may inhibit or prevent loss of contact of the device with opening 1280 (such as an opening through the septal wall), which otherwise may result in a peri-shunt leak that may allow a greater flow of blood from one atrium to another than desired. Additionally, because the inner dimension of the device may be changed independently of the outer dimension (for example, reducing the dimension of the inner martensitic frame device does not change the dimension of the outer austenitic frame), leaving the outer dimension in contact with the opening, there may be reduced, minimal, no disruption or injury to the healing or healed puncture site, and reduced, minimal, or no risk of dislodgment of any thrombus, vegetation, or other tissue that may have grown around the outside of the device during the healing process following formation of opening 1280, e.g., following septal wall puncture and device implantation.

Figure 13A:
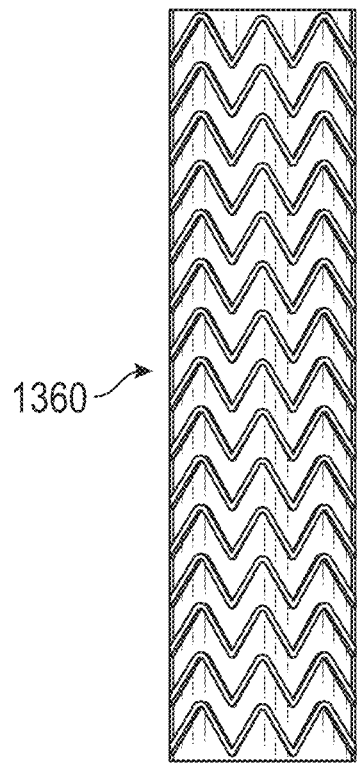
FIGS. 13A-13B schematically illustrate another example modification of the device of FIG. 7.
Figure 13B:
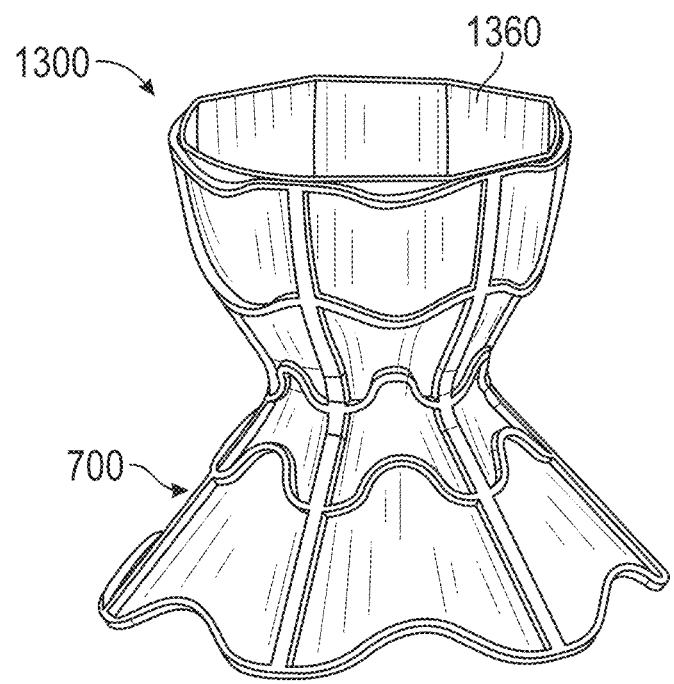

Another way to provide a device for which the inner dimension may be reduced in-vivo is to place a shunt inside of another shunt. This "shunt-in-shunt" approach may be useful, for example, in the circumstance where it would be desired to change the inner shunt anytime after implanting the outer shunt. For example, FIGS. 13A-13B schematically illustrate another example modification of the device of FIG. 7 including a "shunt-in-shunt" arrangement. FIG. 13A illustrates an example cylindrical shunt 1360 that may be used as an inner shunt, e.g., an Advanta V12 balloon expandable covered stent, which is encapsulated in PTFE and commercially available from Getinge AB (Gothenburg, Sweden). In a manner such as illustrated in FIG. 13B, device 1300 may include shunt 1360 placed within shunt 700 described with reference to FIG. 7. In some examples, inner shunt 1360 and outer shunt 700 may be encapsulated independently from one another, may be separable from one another, and optionally may be implanted independently from one another. Inner shunt 1360 may include a malleable shape-memory material, and outer shunt 700 may include a self-expanding superelastic material.

Illustratively, outer shunt 700 may be implanted in a patient at a first time, and may have a neck dimension that is initially expected to be suitable for the patient. If, at a later time, it may be determined that a different neck dimension would be more suitable for the patient, inner shunt 1360 may be implanted within outer shunt 700 so as to provide that neck dimension, which may be smaller or larger than the neck dimension of outer shunt 700. Inner shunt 1360 may be expanded and optionally contracted in a manner such as to define the rate of fluid flow through device 1300. For example, if it is desired to increase the rate of fluid flow through device 1300, inner shunt 1360 may be selected so as to have a larger dimension than device 700 and a hoop strength sufficient to suitably expand the dimension of device 700 and of any opening through which device 700 may be lodged. In such an example, inner shunt 1360 need not necessarily include a malleable shape-memory material, but instead may include a self-expanding superelastic material that may be heat-set so as to have a maximum neck dimension of suitable size and flared ends that respectively contact the flared ends for outer shunt 700 so as to inhibit the flow of blood between the two shunts. In another example, inner shunt 1360 may include a neck with a malleable shape-memory material with a heat-set minimum neck dimension of suitable size, and self-expanding superelastic flared ends that respectively contact the flared ends for outer shunt 700 so as to inhibit the flow of blood between the two shunts. The size of the neck of inner shunt 1360 may be increased and reduced in a manner such as described elsewhere herein. Optionally, inner shunt 1360 may be implanted at the same time as outer shunt 700, e.g., may be disposed within outer shunt 700, the two shunts crimped together and delivered through a sheath, and both deployed simultaneously with one another through the sheath.

It will be appreciated that the present devices may be used in any suitable part(s) of the human body, and are not limited to transatrial shunts. For example, FIGS. 14A-14C schematically illustrate another example device with multiple internal dimensions that can be reduced and increased in vivo, and an example of its use in the human body. Device 1400 illustrated in FIGS. 14A-14C may be used, for example, for treating an abdominal aortic aneurism 140 (AAA). Device 1400 includes a component including a self-expanding superelastic material (designated "B") which may be positioned within AAA 140, and one or more components respectively including malleable shape-memory materials (designated "A" and "C"). Components A and C may have smaller dimensions than component B when initially implanted. Device 1400 may be percutaneously delivered by crimping the device to a cylindrical shape using a crimper, placed within a sheath, and delivered over guidewire 1401 through the external iliac artery to the desired location (abdominal aortic—pararenal). The crimped device 1400 may be implanted such that the distal end (component A) is below the renal ostium and component B is within AAA 140, as illustrated in FIG. 14A. Following implantation, component A may be expanded (e.g., using balloon 1402 dilatation) in a manner such as illustrated in FIG. 14B so as to inhibit the leakage of blood between the device and the blood vessel, and to fixate the device in the desired position.

In some cases, following implantation the inner dimension of the blood vessel may increase which may result in an endoleak. To seal such endoleak, or for any other desired purpose, component C may be expanded (e.g., using balloon 1403 dilatation). As such, fluid flow through AAA 140 may be shunted through device 1400 in such a manner as to reduce the risk of rupture of the AAA. If it is desired to move device 1400, then the dimensions of components A and C may be reduced by applying heat in a manner such as described elsewhere herein. Device 1400 then may be removed, or may be moved to a new location as desired and the dimensions of one or both of components A and C again may be expanded so as to fixate the device in the blood vessel. It should be appreciated that the shape-memory material of component C (corresponding to third component 321) may have a first cross sectional area, which may be expanded, contracted (e.g., to a heat-set dimension), and then re-expanded. The cross sectional areas of component A (corresponding to second component 320) and C may be, but need not necessarily be, the same as one another. Component A (corresponding to second component 320) may be configured as an inlet, and component C (corresponding to third component 321) may be configured as an outlet fluidically coupled to the inlet via component B (corresponding to first component 310). Component A may be configured to engage a blood vessel in the human body, and component C may be configured to extend into an ostium of the blood vessel in a manner such illustrated in FIGS. 14A-14C. A fourth component C may extend into a different ostium of the blood vessel in a manner such as illustrated in FIGS. 14A-14C. In one example, when device 1400 is first positioned in the blood vessel, component B is fully expanded, and components A and C are compressed (crimped); after orientation confirmation of component B and ensuring that the side-branch arteries are not occluded, components A and C may be opened in a controlled manner.

Figure 15A:
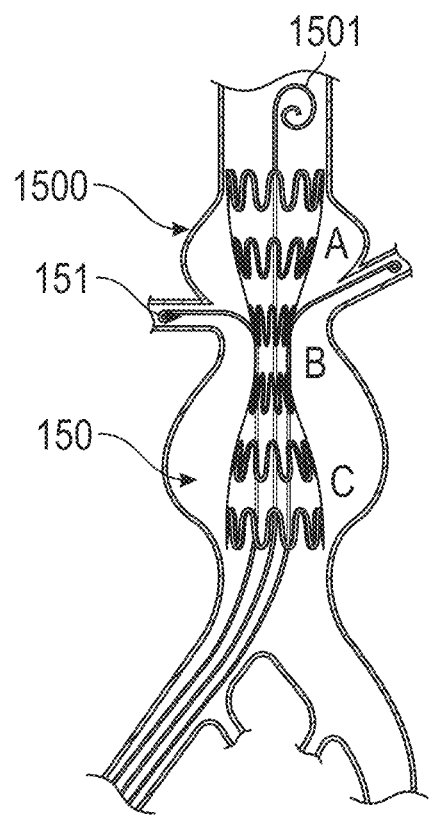
FIGS. 15A-15D schematically illustrate another example device with an internal dimension that can be reduced and increased in vivo, and an example of its use in the human body.
Figure 15B:
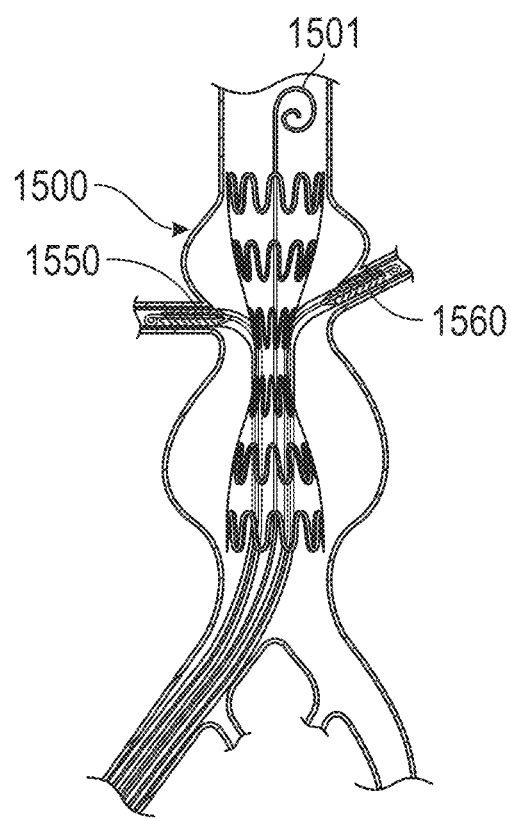
Figure 15C:
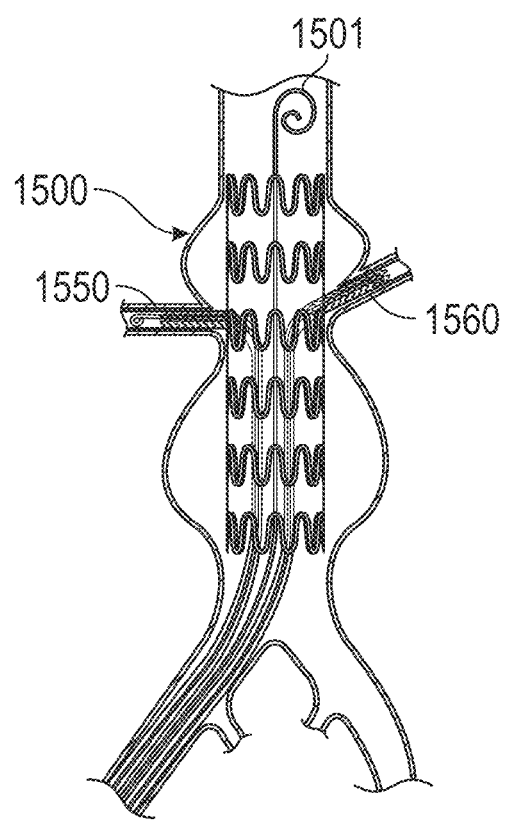
Figure 15D:
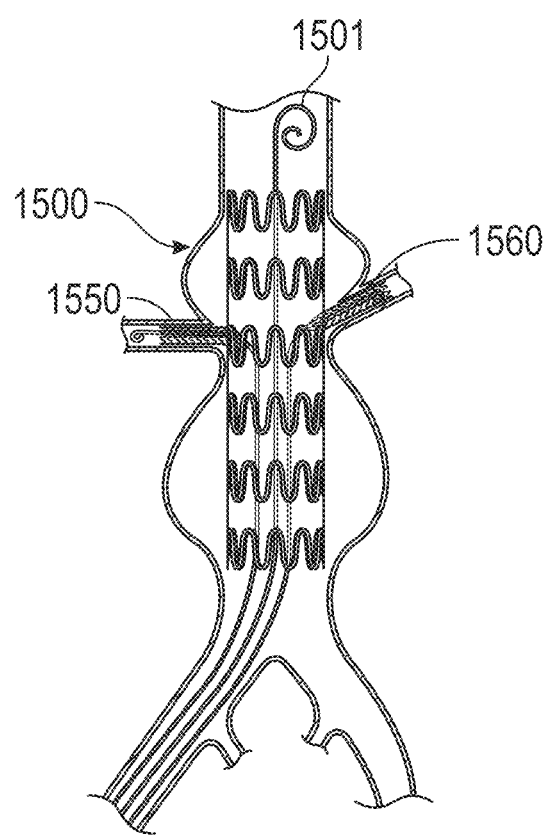

FIGS. 15A-15D schematically illustrate another example device with an internal dimension that can be reduced and increased in vivo, and an example of its use in the human body. Device 1500 illustrated in FIGS. 15A-15C may be used, for example, for treating a fenestrated AAA 150. Device 1500 includes one or more components respectively including self-expanding superelastic materials (designated "A" and "C"), one of which may be positioned within AAA 150, and a component including a malleable shape-memory material (designated "B"). Components A and C may have larger dimensions than component B when initially implanted. Device 1500 may be percutaneously delivered by crimping the device to a cylindrical shape using a crimper, placed within a sheath, and delivered over guidewire 1501 through the external iliac artery to the desired location (abdominal aortic—suprarenal). The crimped device 1500 may be implanted such that the distal end (component A) is above the renal ostium 150, component B is adjacent the renal ostium, and component C is within AAA 150, as illustrated in FIG. 15A. The smaller initial outer dimension of component B may facilitate the positioning of a guidewire into the renal artery. Following the positioning of the guidewire, renal stents 1550, 1560 respectively may be inserted into the renal arteries via introducers, as illustrated in FIG. 15B. While the sheaths are in place, component B may be balloon expanded, as illustrated in FIG. 15C. If at this stage the position of the guidewire is lost, the dimension of component B may be reduced by application of heat. Following dilatation of component B, covered stents may be deployed in the renal arteries. Stents 1550, 1560, together with device 1500 following removal of the sheaths, may provide a fenestrated endovascular graft to repair AAA 150, such as illustrated in FIG. 15D. As such, fluid flow through AAA 150 may be shunted through device 1500, which is supported by stents 1550, 1560, in such a manner as to reduce the risk of rupture of the AAA. Additionally, as compared to previously known devices, device 1500 may provide an expandable middle section B which beneficially may reduce blood flow velocity and turbulent flow.

Figure 16A:
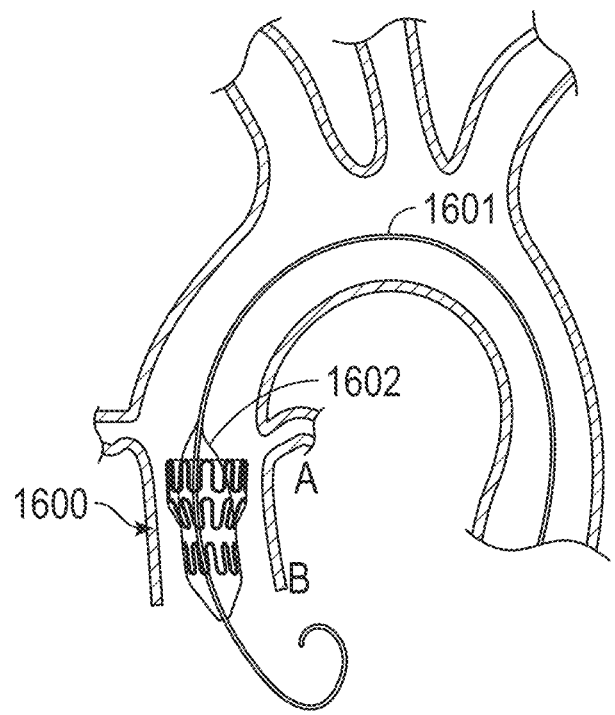
FIGS. 16A-16B schematically illustrate another example device with an internal dimension that can be reduced and increased in vivo, and an example of its use in the human body.
Figure 16B:
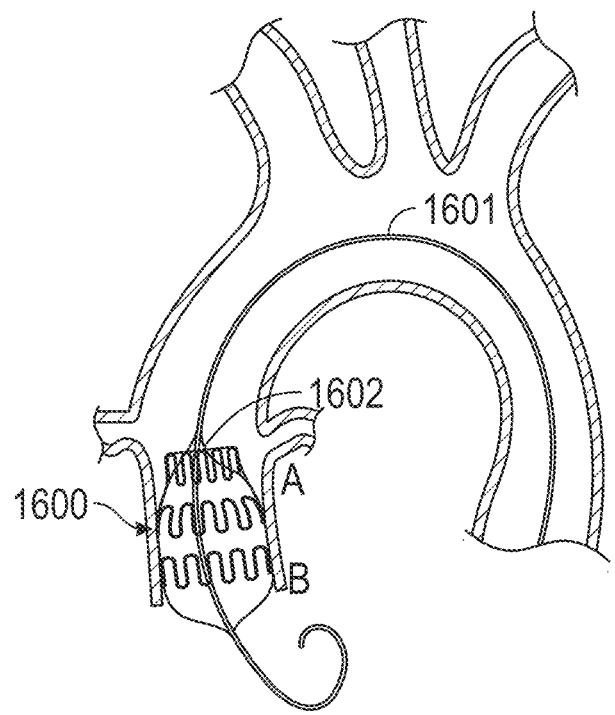

FIGS. 16A-16B schematically illustrate another example device with an internal dimension that can be reduced and increased in vivo, and an example of its use in the human body. Device 1600 illustrated in FIGS. 16A-16B may be used, for example, for providing aortic or mitral valve replacement devices or for closing the left atrial appendage (LAA). Device 1600 includes a component including a self-expanding superelastic material (designated "A") which may be positioned within a desired portion of a blood vessel, such as the aortic artery, and a component including a malleable shape-memory material (designated "B"). Component B may have a smaller dimension than component A when initially implanted. Device 1600 may be percutaneously delivered by crimping the device to a cylindrical shape using a crimper, placed within a sheath, and delivered over guidewire 1601 through blood vessels to the desired location, as illustrated in FIG. 16A. Following implantation, component B may be expanded (e.g., using balloon 1602 dilatation) in a manner such as illustrated in FIG. 16B so as to inhibit the leakage of blood between the device and the blood vessel, and to fixate the device in the desired position. As such, fluid flow through the blood vessel may be shunted through device 1600 in such a manner as to treat the patient, e.g., so as to replace the aortic or mitral valve, or so as to close the LAA. If it is desired to move device 1600, then the dimensions of component B may be reduced by applying heat in a manner such as described elsewhere herein. Device 1600 then may be removed, or may be moved to a new location as desired and the dimension of component B again may be expanded so as to fixate the device in the blood vessel. In configurations in which it is desired to replace a valve, such as the aortic or mitral valve, device 1600 may include a valve disposed either in component A or in component B. For example, component A may be configured to engage a blood vessel in a manner such as illustrated in FIGS. 16A-16B, and component B may extend into the blood vessel and may include a valve disposed therein.

Figure 17:
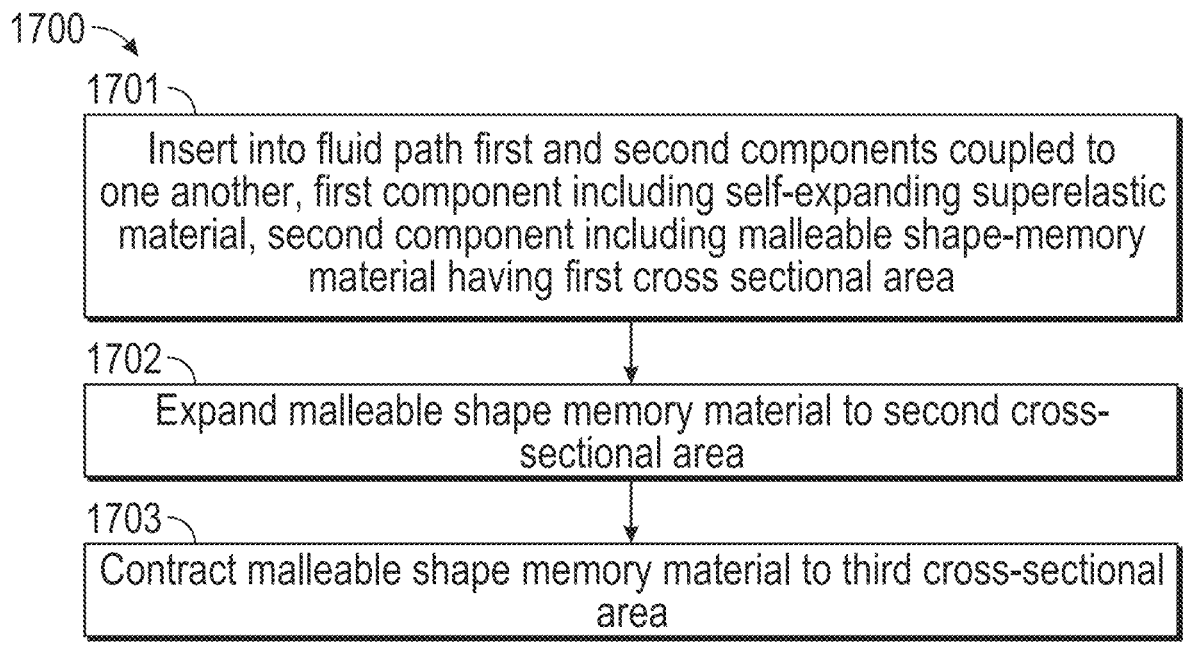
FIG. 17 illustrates a flow of operations in an example method for reducing and increasing an internal dimension of a device in vivo.

It will be appreciated that any of the devices provided herein, not necessarily limited to the particularly illustrated examples, may be used in a method for adjustably regulating fluid flow. For example, FIG. 17 illustrates a flow of operations in an example method 1700 for reducing and increasing dimension of a device in vivo. Method 1700 may include inserting into a fluid path first and second components coupled to one another (1701). The first component may include a self-expanding superelastic material, and the second component may include a malleable shape-memory material having a first cross sectional area. Nonlimiting examples of such first components and second components, and optional configurations thereof, are described with reference to FIGS. 1A-1E, 2A-2E, 3A-3D, 4A-4B, 5A-5B, 6, 7, 8A-8D, 9A-9B, 11A-11B, 12A-12B, 13A-13B, 14A-14C, 15A-15D, and 16A-16B.

Method 1700 illustrated in FIG. 17 also may include expanding the malleable shape-memory material to a second cross sectional area (operation 1702). For example, as described elsewhere herein, the malleable shape-memory material may be expanded using balloon dilatation.

Method 1700 illustrated in FIG. 17 contracting the malleable shape-memory material to a third cross sectional area (operation 1703). For example, as described elsewhere herein, the malleable shape-memory material may be contracted using heat, for example as applied using saline heated to above Af of the shape-memory material, or using another suitable energy source such as radio frequency electrical current (RF).

Accordingly, in examples provided herein, a fluid flow path through an implantable device may be both increased and reduced following implantation, allowing for repositioning of the device or a customized fluid flow that is appropriate to the particular patient's needs. In comparison, for previously known devices repositioning may not be possible, and the size of the fluid flow path either is selected prior to implantation or may be increased using balloon dilatation, providing limited options for achieving a desired hemodynamic result in a patient. In examples such as provided herein, the component(s) including self-expanding superelastic material(s) may assume their shape immediately upon implantation within the body, which may inhibit device migration and ensure accurate positioning. The component(s) including malleable shape-memory material(s) may be plastically deformable (e.g., expandable) at body temperature and may be returned to a heat-set dimension upon application of heat. The heat-set dimension of a malleable shape-memory component optionally may be larger than a crimped dimension of the component. Accordingly, in some examples a malleable shape-memory component may be expanded by suitably applying heat, e.g., as an alternative to an initial balloon dilatation after delivery of the crimped device. The malleable shape-memory component(s) repeatedly may be expanded and contracted, which may allow for adjustment of fluid flow through the device, or for the device to be repositioned, or a combination of such features.

For example, certain of the devices provided herein may be repositionable for fixation within a body lumen. As described above, the devices may include a first component including a self-expanding superelastic material, and a second component coupled to the first component and comprising a malleable shape-memory material, in a manner such as described with reference to FIGS. 1A-1E, 2A-2E, 3A-3D, 4A-4B, 5A-5B, 6, 7, 8A-8D, 9A-9B, 11A-11B, 12A-12B, 13A-13B, 14A-14C, 15A-15D, and 16A-16B. The self-expanding superelastic material may have a predetermined fully expanded dimension (e.g., that may be heat set during manufacture). The second component may have a first dimension suitable for deployment through a catheter (e.g., may be crimped to that dimension). The malleable shape-memory material may be expandable to a second dimension for fixation within a body lumen (e.g., via balloon dilatation), and may be thermally transitionable to a third dimension (e.g., via application of heat within the body as described elsewhere herein). The malleable shape-memory material may be mechanically re-expandable to a fourth dimension (e.g., via balloon dilatation).

Figure 18:
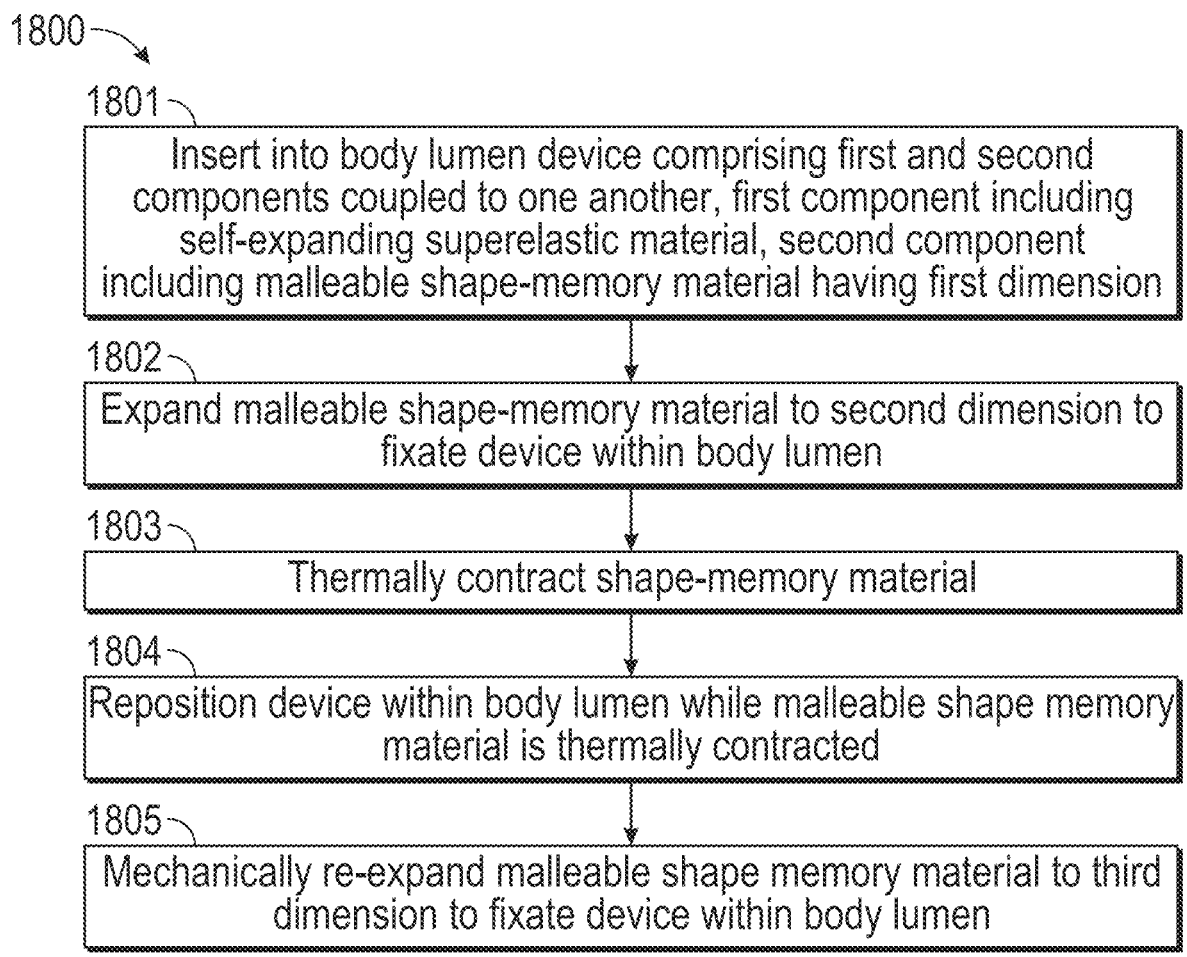
FIG. 18 illustrates a flow of operations in an example method for fixating a device in a body lumen.

Accordingly, it will be appreciated that certain of the devices provided herein, not necessarily limited to the particularly illustrated examples, may be used in a method for adjustably fixating a device within a body lumen. For example, FIG. 18 illustrates a flow of operations in an example method 1800 for repositioning a device. Method 1800 includes inserting into a body lumen a device comprising first and second components coupled to one another (operation 1801). The first component may include a self-expanding superelastic material, and the second component may include a malleable shape-memory material having a first dimension, in a manner such as described with reference to FIGS. 1A-1E, 2A-2E, 3A-3D, 4A-4B, 5A-5B, 6, 7, 8A-8D, 9A-9B, 11A-11B, 12A-12B, 13A-13B, 14A-14C, 15A-15D, and 16A-16B.

Method 1800 also includes expanding the malleable shape-memory material to a second dimension to fixate the device within a body lumen (operation 1802), for example via balloon dilatation. Method 1800 also includes thermally contracting the malleable shape-memory material (operation 1803), for example via application of heat. Method 1800 also includes repositioning the device within the body lumen while the malleable shape-memory material is thermally contracted (operation 1804), for example by moving the device along a guidewire. Method 1800 also includes mechanically re-expanding the malleable shape-memory material to a third dimension to fixate the device within the body lumen (operation 1805), for example via balloon dilatation.

Although certain examples provided herein relate to permanently implantable devices for use in the human body, it should be appreciated that other examples relate to devices that are used only temporarily in the human body. Additionally, although certain examples herein primarily relate to changing the internal dimension of a device, it should be appreciated that other examples primarily relate to changing the external dimension of a device. For example, FIGS. 19A-19D schematically illustrate an example dilator device 1900 with an external dimension that can be reduced and increased in vivo. Device 1900 may be used, for example, in a "sheathless" method for delivering a permanently implantable device to a suitable location in the human body using an over-the-wire (OTW) approach, e.g., in a manner such as described with reference to FIGS. 20A-20I.

Figure 19A:
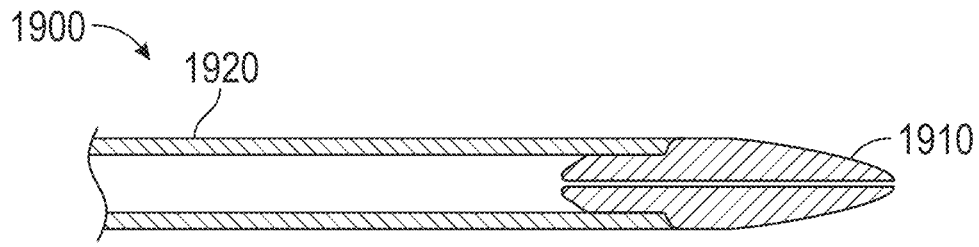
FIGS. 19A-19D schematically illustrate an example dilator device with an external dimension that can be reduced and increased in vivo.
Figure 19B:
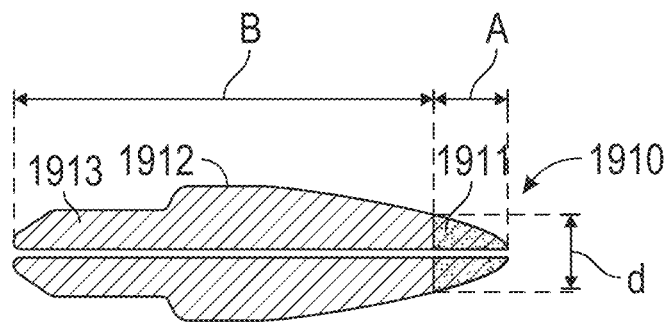

In the example shown in FIG. 19A, device 1900 may include dilator 1910 disposed at the distal end of sheath 1920. As shown in greater detail in FIG. 19B, dilator 1910 may include tip 1911, enlarged region 1912, and reduced region 1913. Reduced region 1913 may be sized so as to securably engage with the distal end of sheath 1920, and enlarged region 1912 may be sized so as to provide device 1900 with a smooth profile between sheath 1920 and tip 1911. Tip 1910 may have an outer dimension d where tip 1911 meets enlarged region 1912, and its distal end may taper to approximately a point. In the example configuration shown in FIG. 19B, dilator 1910 includes a martensitic shape-memory material defining enlarged region 1912 and reduced region 1913 (together, denoted region B), and a self-expanding superelastic material defining tip 1911 (denoted region A). The austenitic finish temperature (Af) of the self-expanding superelastic material may be less than body temperature (which is about 37° C.), e.g., may be in the range of 5–15° C. The Af of the martensitic shape memory material may be substantially greater than 37° C., e.g., may be about 45-60° C., e.g., may be about 50° C. Tip 1910, reduced region 1913, and enlarged region 1912 optionally are integrally formed from a common frame with one another.

Figure 19C:
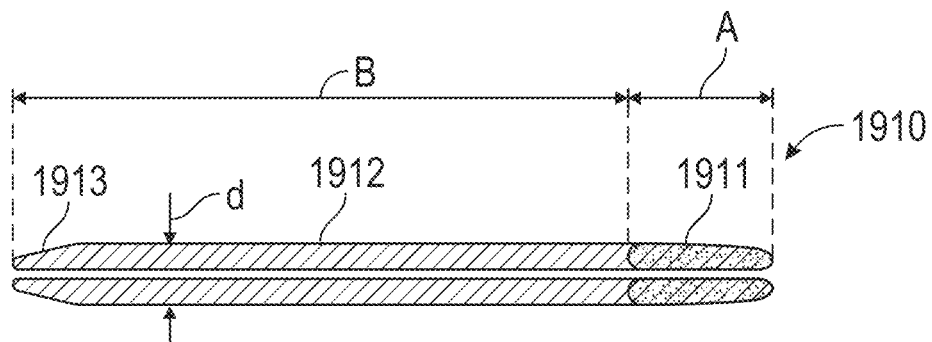
Figure 19D:
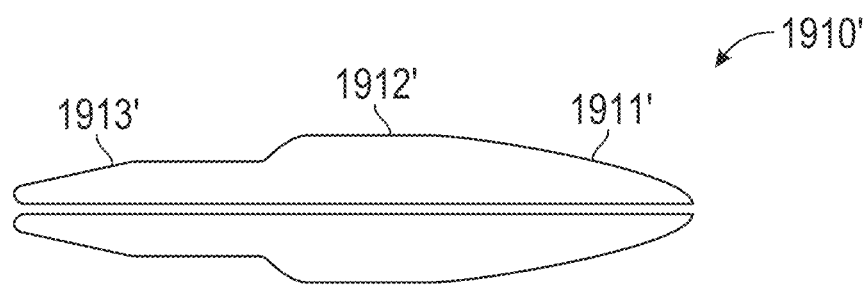

As shown in FIG. 19C, upon application of heat (e.g., using hot saline or RF energy or the use of a laser, magnetic inductance, electrical resistance, or the like) the shape memory material of region B (corresponding to enlarged region 1912 and reduced region 1913) may return to a smaller, heat-set outer dimension that optionally may be approximately equal to d so that the dilator 1910 has a substantially smooth, reduced size profile. In the alternative configuration shown in FIG. 19D, dilator 1910' includes a martensitic shape-memory material defining tip 1911, enlarged region 1912, and reduced region 1913, which may be configured to return to a smaller, heat-set dimension that optionally may be approximately equal to d so that the dilator 1910 has a substantially smooth, reduced size profile.

Figure 20A:
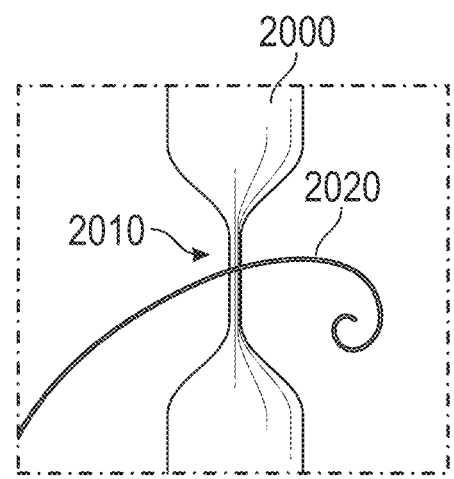
FIGS. 20A-20I schematically illustrate use of the delivery device of FIGS. 19A-19D in the human body.
Figure 20B:
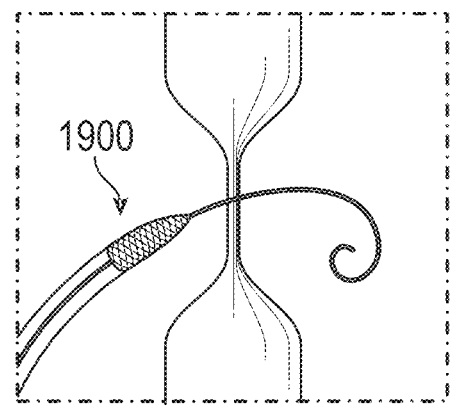
Figure 20C:
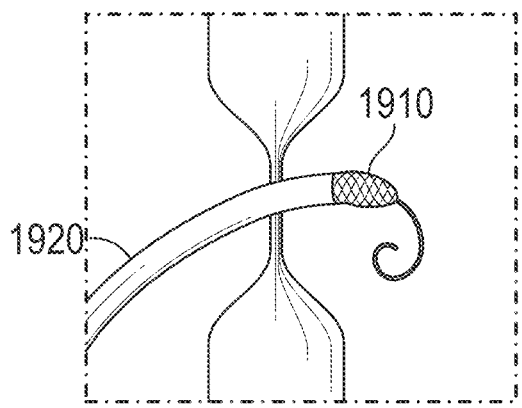
Figure 20D:
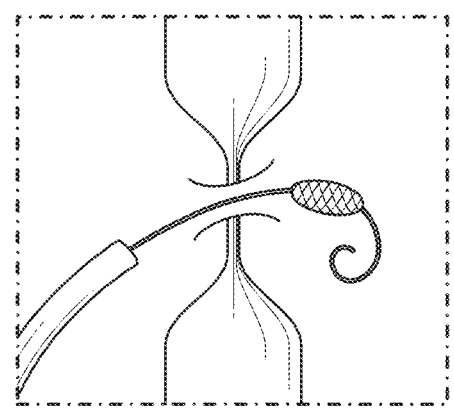
Figure 20E:
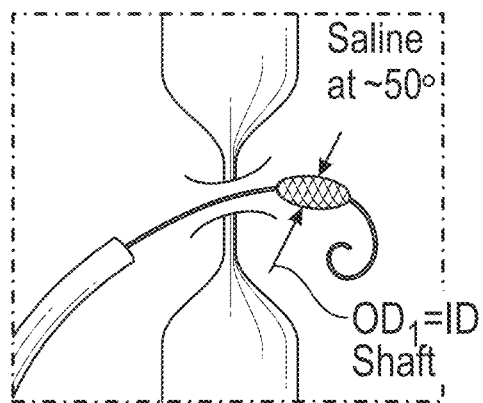
Figure 20F:
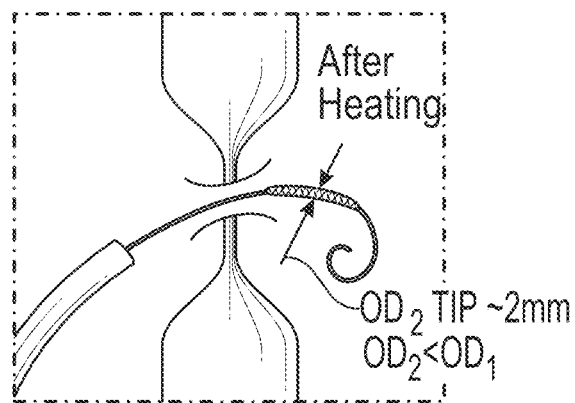
Figure 20G:
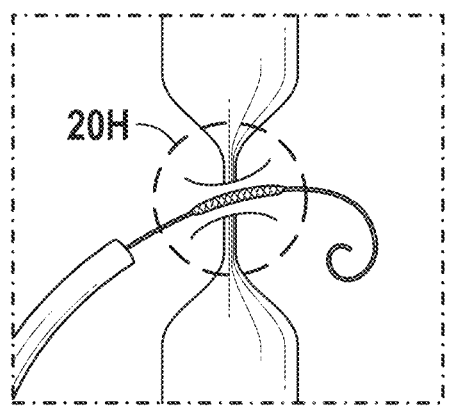
Figure 20H:
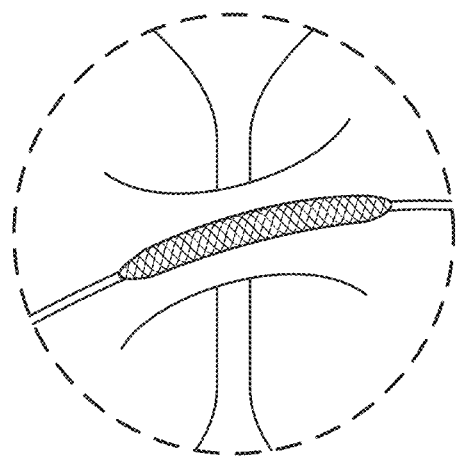
Figure 20I:
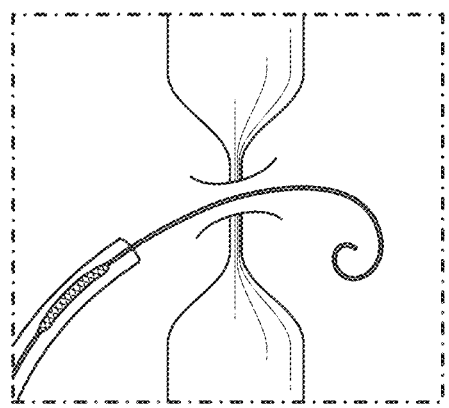

FIGS. 20A-20I schematically illustrate use of the delivery device 1900 of FIGS. 19A-19D in the human body. In the nonlimiting example shown in FIG. 20A, guidewire 2020 is percutaneously placed across a region of the body to be dilated, for example, fossa ovalis 2010 of interatrial septum 2000, creating a small opening having approximately the dimension of guidewire 2020. Device 1900 then is advanced over guidewire 2020 to a position adjacent to fossa ovalis 2010 in a manner such as illustrated in FIG. 20B. As shown in FIG. 20C, pushing on the proximal end of sheath 1920 forces dilator 1910 through fossa ovalis 2010, enlarging the opening to approximately the outer dimension of enlarged region 1912. As shown in FIG. 20D, sheath 1920 may be retracted relative to dilator 1910, leaving dilator 1910 in place on the distal side of fossa ovalis 2010. So as to inhibit harming the tissue of interatrial septum 2000 when retracting dilator 1910, e.g., by catching tissue with enlarged region 1912 when retracting dilator 1910, and so as to inhibit dilator 1910 from catching or becoming entangled with an expandable device that may be delivered across the septum in a manner such as described below, heat may be applied to dilator 1910 on the distal side of fossa ovalis 2010 as shown in FIG. 20E, for example by applying hot saline or RF energy or the use of a laser, magnetic inductance, electrical resistance, or the like at a temperature above the Af of the shape memory material of the dilator. Such heat causes the outer dimension of the enlarged region 1912 to return to its heat-set size. As shown in FIG. 20G and its inset 20H, the reduced-size dilator 1910 may be safely withdrawn through the enlarged opening, and then may be stowed inside of sheath 1920 in a manner such as illustrated in FIG. 20I and subsequently withdrawn from the body. Note that any suitable one of the adjustable devices described elsewhere herein, such as device 700, 1100, 1300, or 2100 may be delivered using delivery device 1900. For example, the adjustable device may be disposed within sheath 1920 and advanced to partially cross the atrial septum together with delivery device 1900 in a manner such as shown in FIG. 20C. Retracting sheath 1920 in a manner such as shown in FIG. 20D deploys the distal shunt flange of the adjustable device in the left atrium, followed by pulling the sheath back to the septal wall, releasing the retention hooks, and pulling the sheath further back such that the septum drags the remainder of the shunt out of the sheath, allowing the proximal flange of the shunt to self-expand in the right atrium. The dimension of dilator 1910 then may be adjusted in vivo and withdrawn through the adjustable device, thus providing a "sheathless" implantation procedure with a relatively low crossing profile and a relatively short procedure time.

Figure 21A:
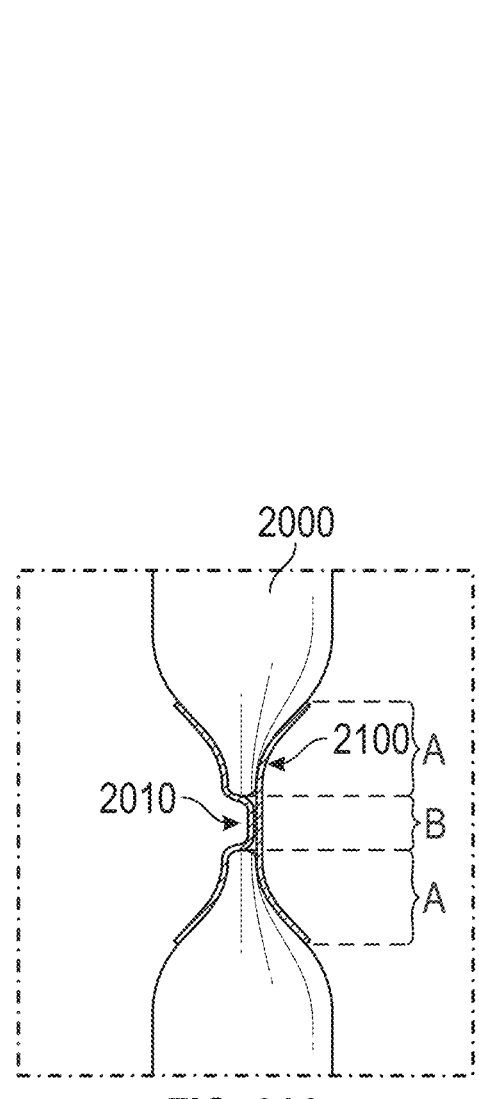
FIGS. 21A-21D schematically illustrate an example transatrial gate with an internal dimension that can be reduced and increased in vivo.
Figure 21B:
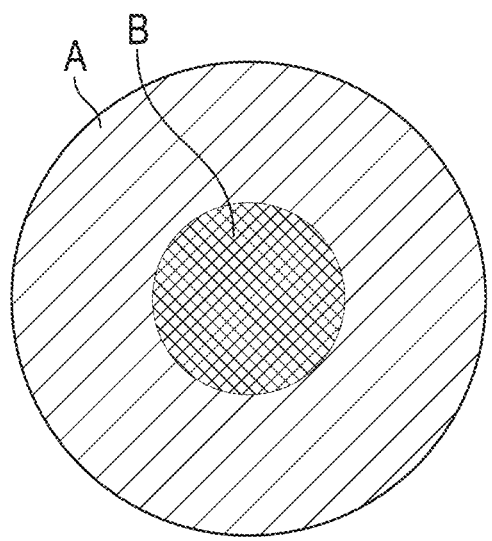
Figure 21C:
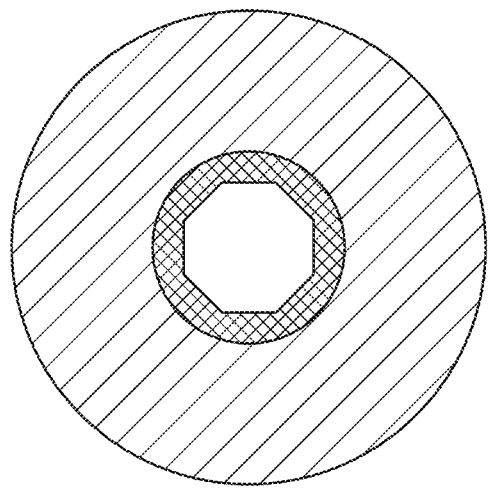
Figure 21D:
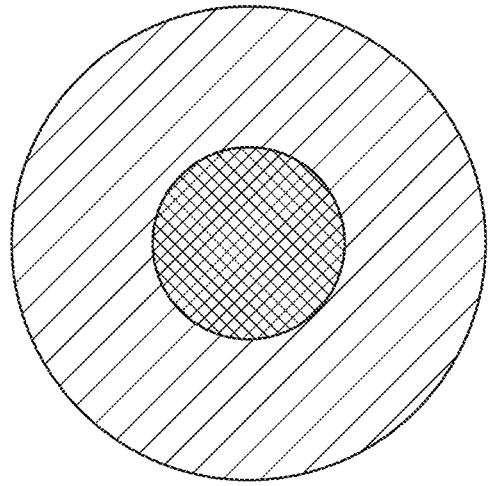

FIGS. 21A-21D schematically illustrate an example transatrial gate 2100 with an internal dimension that can be reduced and increased in vivo. As illustrated in cross sectional area in FIG. 21A, transatrial gate 2100 may be disposed across an opening through interatrial septum 2000, e.g., through fossa ovalis 2010. Transatrial gate 2100 includes left and right atrial discs (denoted "A" in FIGS. 21A-21D) each including a self-expanding superelastic material, and a martensitic shape-memory material (denoted "B" in FIGS. 21A-21D) which has an Af that is substantially higher than body temperature, e.g., 45-60° C., e.g., from 50-55° C. Left atrial disc A, right atrial disc A, and martensitic shape-memory material optionally are integrally formed from a common frame with one another. In one example, the martensitic shape-memory material B may be provided as a mesh that forms an internal dimension that may be reduced and expanded in vivo. For example, as shown in FIG. 21B, the martensitic shape-memory material B may be heat set to completely occlude passage between the left and right atrial discs A, corresponding to an internal dimension of approximately zero. As shown in FIG. 21C, the martensitic shape-memory material B may be mechanically expanded to provide any suitable expanded internal dimension allowing passage between the left and right atrial discs A. As shown in FIG. 21D, upon heating above Af, the martensitic shape-memory material may return to its heat set configuration.

Figure 22A:
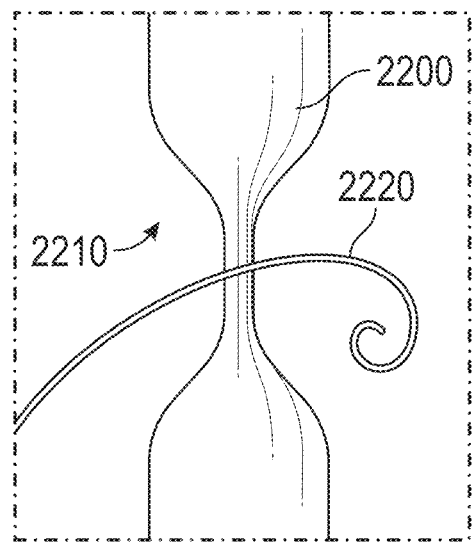
FIGS. 22A-22H schematically illustrate use of the transatrial gate of FIGS. 21A-21D in the human body.
Figure 22B:
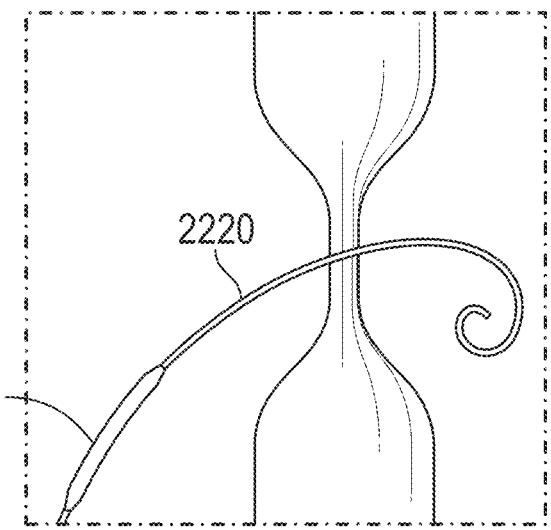
Figure 22C:
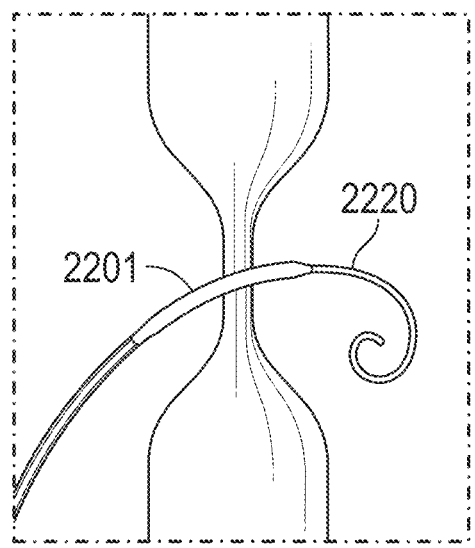
Figure 22D:
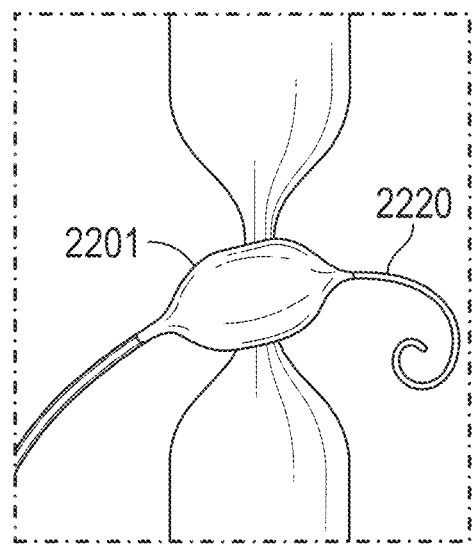
Figure 22E:
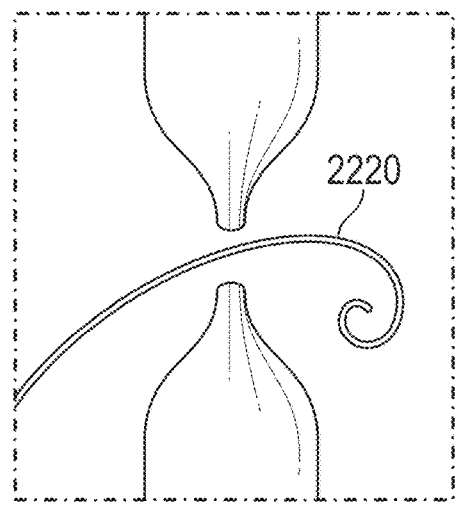
Figure 22F:
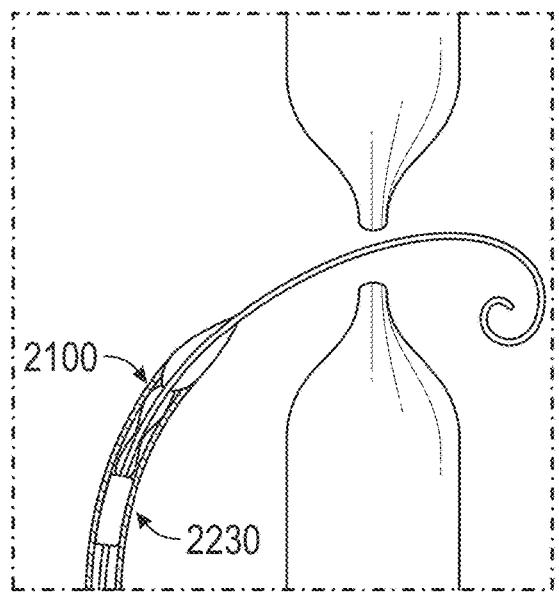
Figure 22G:
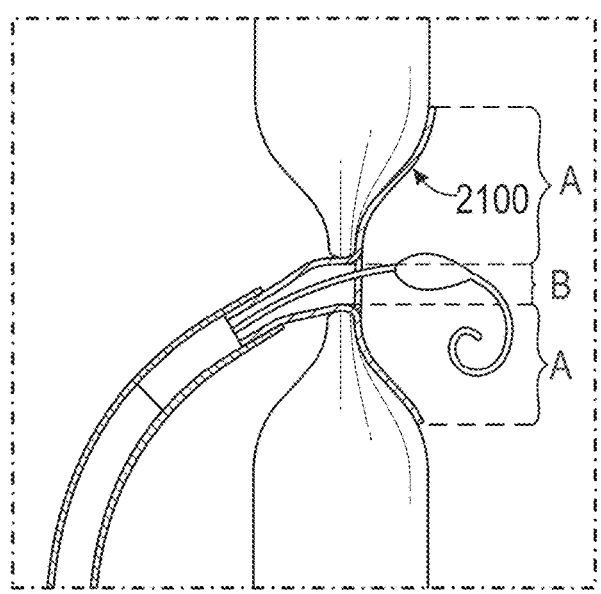
Figure 22H:
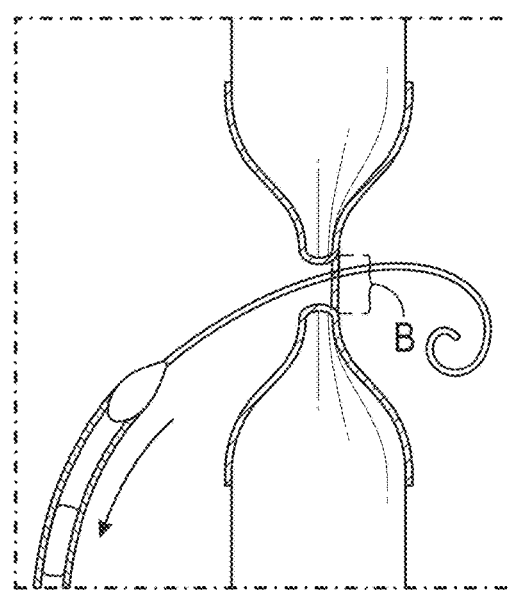

FIGS. 22A-22H schematically illustrate use of the transatrial gate of FIGS. 21A-21D in the human body. In an example use of transatrial gate 2100 as a standalone adjustable transatrial shunt, a guidewire 2220 is used to perform a transseptal puncture in a manner such as shown in FIG. 22A, optionally through fossa ovalis 2210. The opening through atrial septum 2200 optionally may be expanded using an introducer sheath and dilator (not illustrated), or by advancing a noncompliant balloon 2201 over guidewire 2220 and then expanding the balloon in a manner such as illustrated in FIGS. 22B-22D. In one nonlimiting example, the balloon has a maximum outer dimension of 15 mm, although any suitable dimension may be used. The balloon or dilator then is removed, keeping guidewire 2220 in place as shown in FIG. 22E. Adjustable transatrial gate 2100 is implanted, for example by advancing gate 2100 crimped into sheath 2230 over the guidewire in a manner such as shown in FIG. 22F and partially through the atrial septum, and then retracting sheath 2230 allowing the distal end (left side in the illustrated configuration) of gate 2100 to deploy via self-expansion of left atrial disk A in a manner such as shown in FIG. 22G. The sheath is then further retracted, allowing the proximal end (right side in the illustrated configuration) of gate 2100 to deploy via self-expansion of right atrial disk A in a manner such as shown in FIG. 22H. Guidewire 2220 may be left through gate 2100. The gate then is crossed with a dilator having a suitable outer dimension, e.g., of 5 mm, which mechanically expands the inner dimension of martensitic shape-memory material B to the outer dimension of the dilator, e.g., to 5 mm. The inner dimension of martensitic shape-memory material B then may be further increased as appropriate, e.g., using similar mechanical expansion using a larger dilator. If it is determined that the inner dimension of the martensitic shape-memory material B is too large, then it may be heated above its Af to reset that material to its heat set configuration. The inner dimension of the material then may be expanded to another suitable size.

In an example use of transatrial gate 2100 as transatrial channel that may be opened and closed, a guidewire is used to perform a transseptal puncture. The opening through atrial septum, which optionally is through the fossa ovalis, may be expanded using an introducer sheath and dilator. The dilator then is removed, keeping the sheath in place. A procedure then may be performed in the left atrium via the expanded opening, such as RF ablation, left atrial appendage (LAA) closure, MitraClip implantation, mitral valve replacement, mitral valve repair, or the like. The adjustable transatrial gate is implanted in a manner such as described with reference to FIGS. 21A-21H, e.g., with martensitic shape-memory material in its heat-set state with minimal or zero inner aperture. Optionally, a guidewire is left through the gate and the gate then is crossed with a dilator having a suitable outer dimension, e.g., of 5 mm, which mechanically expands the inner dimension of martensitic shape-memory material B to the outer dimension of the dilator, e.g., to 5 mm. The inner dimension of martensitic shape-memory material B then may be further increased as appropriate, e.g., using similar mechanical expansion using a larger dilator. If it is determined that the inner dimension of the martensitic shape-memory material B is too large, then it may be heated above its Af to reset that material to its heat set configuration. The inner dimension of the material then may be expanded to another suitable size. The gate may be left open and used to provide a transatrial shunt in a manner such as described above, or may be left closed but reopened as needed so as to perform a separate procedure later on in the left atrium.

Figure 23A:
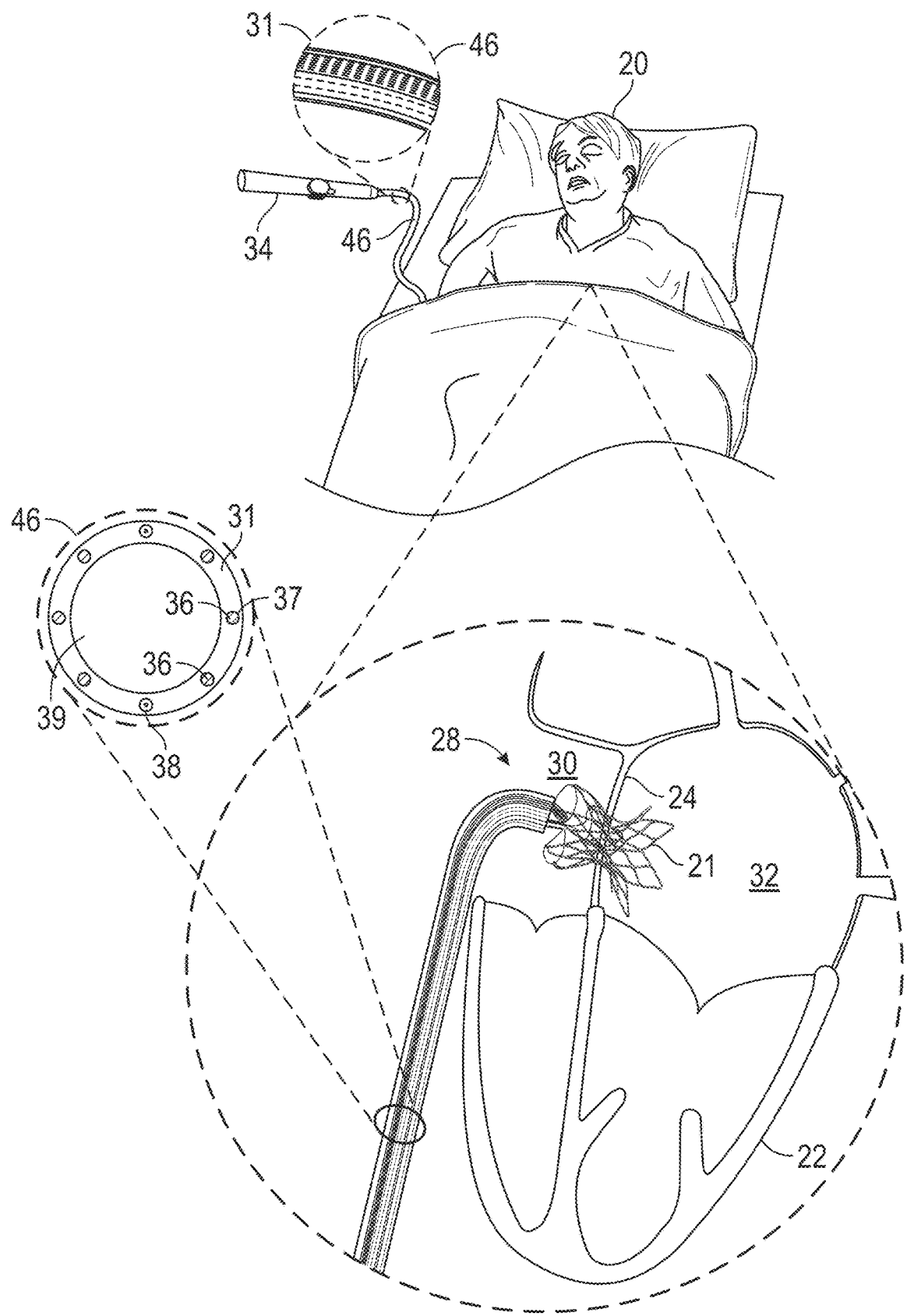
FIGS. 23A-23E schematically illustrate another example device with an internal dimension that can be reduced and increased in vivo, and an example of its temporary use in the human body.
Figure 23B:
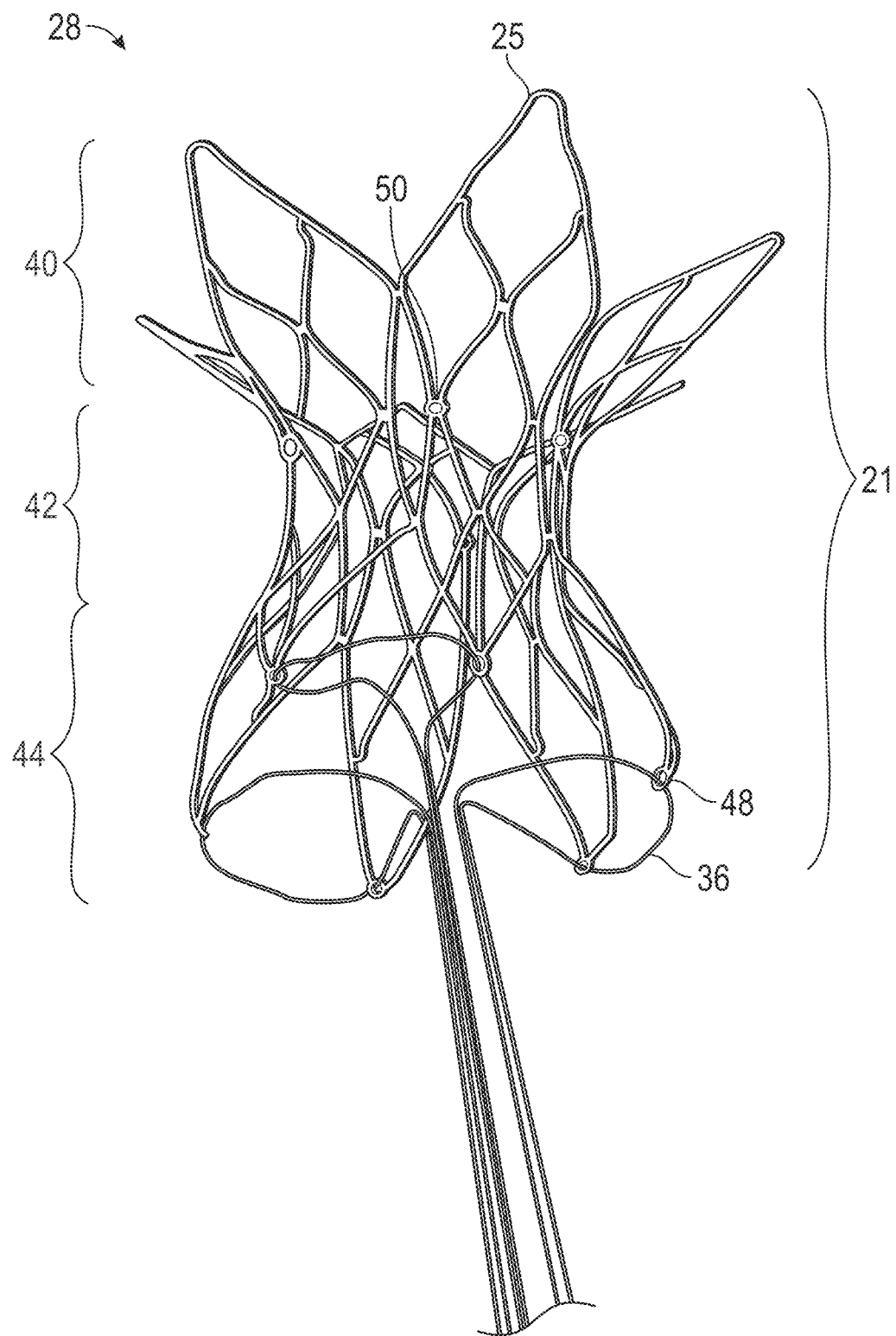

As noted above, the present devices may be permanently or temporarily implanted in the body. In a temporary implantation, the device may be configured for easy removal and may have a dimension that is adjustable in a manner such as described elsewhere herein, or may be permanently connected to the end of a catheter. For example, FIGS. 23A-23E schematically illustrate an example device with an internal dimension that can be reduced and increased in vivo, and an example of its temporary use in the human body. More specifically, FIG. 23A is a schematic illustration of a temporary apparatus 28 inside a subject 20, FIG. 23B is a schematic illustration of temporary apparatus 28, in accordance with some examples provided herein, and FIGS. 23C-23E collectively show a technique for removing temporary apparatus 28 from a subject, in accordance with some examples provided herein.

Apparatus 28 includes device 21, which may be configured similarly as device 200 described with reference to FIGS. 2A-2B or device 700 described with reference to FIG. 7, and which may be placed between two chambers of the heart 22 of subject 20, such as within the interatrial septum 24 of heart 22, between the right atrium 30 and the left atrium 32. Alternatively, the device 21 may be placed between the two ventricles of the heart, or between any other two body cavities. In the example illustrated in FIG. 23B, device 21 includes a flared distal portion 40, a flared proximal portion 44, and an intermediate portion 42, which is disposed between distal portion 40 and proximal portion 44. Distal portion 40 and proximal portion 44 anchor the device 21 to septum 24 (i.e., prevent migration of the device from within the septum), while intermediate portion 42 provides a passageway across the septum, through which blood may flow. In a manner similar to that described with reference to FIGS. 2A-2B and FIG. 7, flared distal portion 40 (first component) may include a first self-expanding material, intermediate portion 42 (second component) may include a malleable shape-memory material, and proximal portion 44 (third component) may include a second self-expanding material. Proximal portion 44, distal portion 40, and intermediate 42 portion optionally are integrally formed from a common frame with one another. The flared distal and proximal portions 40, 44 (first and third components) of device 21 expand to their natural shapes (the shapes shown in FIGS. 23A-23B) upon being released from a delivery sheath 46, while the intermediate portion 42 (second component) provides a cross sectional area that may be increased and reduced in vivo in a manner such as further described below. It is noted that, for clarity, apparatus 28 is drawn disproportionately large, relative to heart 22, in FIG. 23A. The proximal and distal portions 40, 44 of device 21 may be "flared," in that these portions extend radially outward at an acute angle from the axis of the intermediate portion of the stent. In some examples, as shown, each of the proximal and distal portions of the device 40, 44 includes a plurality of leaves 25, such as, for example, six leaves 25, as shown. In other examples, the proximal portion and/or the distal portion does not include a plurality of leaves, but rather, is shaped to define a flared ring, or has some other suitable form.

To facilitate removal of device 21 from the subject in a manner such as described further below with reference to FIGS. 23C-23E, some examples include one or more device-collapsing flexible longitudinal elements 36, which extend from proximal portion 44 to the exterior of the subject. For example, as shown in FIGS. 23A-23B, the device-collapsing flexible longitudinal elements may include control wires 36. In some examples, while inside the subject, wires 36 are contained within control wire lumens 37 of a delivery catheter 31 passing between proximal portion 44 and the exterior of the subject. For example, delivery catheter 31 may exit the subject via a femoral vein of the subject. As shown in FIG. 23A, the proximal ends of control wires 36 may be coupled to control handle 34, via which wires 36 may be pulled (or alternatively, released, such as to allow the proximal portion of the device to expand). Wires 36 may remain coupled to the device 21 throughout the time that the device is in place inside the subject. Due to wires 36 remaining coupled to device 21, the device may be easily removed at any desired time (e.g., immediately) upon receiving indication that further shunting is no longer required through the device, e.g., in a manner such as described with reference to FIGS. 23C-23E. FIG. 23B shows a particular example in which proximal portion 44 is shaped to define a plurality of orifices 48, and each of control wires 36 passes through at least two of orifices 48. For example, as shown, the end of each leaf 25 may be shaped to define an orifice 48, and each wire may pass through the respective orifices of two adjacent leaves, such that the wire forms a loop that passes through the orifices. (Thus, in the illustrated example, device having six proximal leaves is coupled to three wires 36, each wire separately controlling the collapse of a respective pair of adjacent leaves.) To collapse the proximal portion of device 21, the two proximal ends of each of the wires may be pulled.

Alternatively to the example shown, a single wire 36 may form a loop that passes through all of the orifices 48, this single wire controlling the collapse of the entire proximal portion 44. In other words, by pulling on the two ends of this single wire, the entire proximal portion may be collapsed. In yet other examples, wires 36 do not form loops; rather, a separate wire is coupled to each leaf. For example, each leaf may be coupled to the distal end of a respective wire. Thus, for example, a device having six proximal leaves is coupled to six wires, one wire per leaf. Similarly, wires 36 may be formed as extensions of the leaves, such that each leaf has a wire extension that extends to the exterior of the subject. In such examples, the proximal portion of the device may be collapsed by pulling on the single proximal end of each of the wires.

In some cases, it may be beneficial to increase or reduce the cross sectional area of intermediate portion 42 while device 21 is inside the subject, e.g., in a manner such as described elsewhere herein. To allow the cross sectional area of intermediate portion 42 to be increased, delivery catheter 31 may include an enlarged central multipurpose lumen 39 through which an angioplasty balloon or other suitable balloon may be passed over a guidewire and inflated in a manner such as described elsewhere herein. To reduce the cross sectional area of intermediate portion 42, a catheter with one or more holes may be used to inject hot saline within device 21, in a manner such as described elsewhere herein, to heat intermediate portion 42. In some examples, the catheter with one or more holes is passed over a guidewire within delivery catheter 31. In other examples, the catheter with one or more holes is not passed over the guidewire but is introduced to device 21 separately from the guidewire through multipurpose lumen 39 of delivery catheter 31. It will be appreciated that to increase and reduce the cross sectional area of intermediate portion 42, e.g., to provide an appropriate flow rate through device 21 or to reposition device 21, processes of balloon expansion and heating may be repeated any suitable number of times.

In some examples, the adjustment of the cross sectional area of intermediate portion 42 of device 21 is based on pressure monitoring. For example, pressure sensors disposed on the device 21 may be used to acquire intra-atrial pressure measurements. A signal indicative of such pressure measurements may be transmitted outside the body via conductors 38 (also referred to as signal wires), shown schematically in FIG. 23A. The cross sectional area of intermediate portion 42 may be adjusted in response to such measurements.

Alternatively or additionally, the cross sectional area of intermediate portion 42 may be adjusted in response to hemodynamic monitoring, such as by the application of flow imaging techniques such as pulsed wave (PW) or continuous wave (CW) Doppler echocardiography.

In some examples, to place the device 21 within the septum, the device is first collapsed and placed inside a delivery sheath 46 that has been inserted percutaneously into the vasculature of the subject, such as via a femoral vein of the subject, and is then passed through the vasculature into right atrium 30, e.g., via the inferior vena cava. (Alternatively, sheath 46 may be passed into the right atrium via the jugular vein and superior vena cava.) Subsequently, the distal end of the sheath is passed through the septum and into left atrium 32. Prior to passing the distal end of the sheath through the septum, a puncturing element may be used to create an opening in the septum, and, optionally, a dilator may be used to enlarge the opening, such that the distal end of the sheath may easily pass through the septum; in some examples, the dilator is configured and used in a manner such as described with reference to FIGS. 19A-20I. Once the sheath is across the septum, the dilator is removed and the device 21, connected to catheter 31, is collapsed and placed into the proximal end of the delivery sheath 46, and the catheter 31 is used to push the device 21 through the delivery sheath until the distal flared portion 40 of the device is pushed from the distal end of the sheath and allowed to expand to its deployed shape. Sheath 46 is then slowly withdrawn from the septum until the distal flared portion of device 21 engages the left atrial side of the septum. Continued withdrawal of the sheath causes the device 21 to be dragged out of the sheath by the septum, until the proximal flared portion 44 is released, allowing it to expand to its deployed shape on the right atrial side of the septum, as shown in FIG. 23A. The expanded distal and proximal flared portions, 40 and 44, thereby securely anchor the device 21 across the interatrial septum. Intermediate portion 42 (second component) initially may remain in its crimped or compressed configuration having a first cross sectional area, and may be suitably expanded to a second cross sectional area using a balloon which is passed over a guidewire through lumen 39 of catheter 31. The cross sectional area of intermediate portion 42 subsequently may be increased and reduced in vivo in a manner such as described elsewhere herein.

Following the deployment of device 21, sheath 46 and catheter 31 may remain within the subject while device 21 is in place. For example, sheath 46 and catheter 31 may remain within the subject such that the distal end of the catheter is near the proximal portion of the device. The catheter may thus be used to deliver medication to the device site, pressure sensors in the catheter may be used to monitor the intra-atrial pressure, balloons may be introduced within device 21 to increase the cross sectional area of intermediate portion 42, or catheters with one or more holes may be introduced within device 21 to reduce the cross sectional area of intermediate portion 42. By way of example, FIG. 23A shows catheter 31 coupled to a control handle 34, such that control handle 34 may be used to advance and withdraw the catheter through sheath 46.

Device 21 helps relieve excess intra-atrial pressure, by allowing blood to flow from the higher-pressure atrium to the lower-pressure atrium, with a flow rate that may be increased or reduced based on the needs of the particular patient. Device 21 may thus be used as a temporary acute treatment of any relevant condition (e.g., pulmonary hypertension or congestive heart failure) for which the relief of excess pressure is beneficial, or, for example, to help prevent left ventricular dilation and remodeling following an acute myocardial insult. When device 21 is used as an acute treatment, the subject remains hospitalized until the subject's physician decides that sufficient treatment has been provided, at which point device 21 is removed from the subject in a manner such as described with reference to FIGS. 23C-23E, and the subject is released from hospital as appropriate. In some examples, device apparatus 28 includes one or more pressure sensors, disposed, for example, on device 21, on any of the longitudinal elements, or in catheter 31. Such pressure sensors may be used to measure (e.g., continuously) the pressure in the subject's right atrium and/or left atrium, in order to monitor progression of the treatment, to determine whether and by how much the cross sectional area of intermediate portion 42 should be adjusted, and ascertain the point in time at which the device may be removed from the subject. For example, one pressure sensor may be disposed on the proximal portion 40 of device 21, and another pressure sensor on the distal portion 44 of the device, such that the pressure in both the left atrium and the right atrium is measured.

In another embodiment, device 21 is used as temporary measurement device to determine the optimal size for a permanently implanted shunt to be subsequently implanted. In this embodiment, the cross sectional area of intermediate portion 42 of device 21 is adjusted while monitoring pressures and/or other physiological parameters as described for the acute treatment embodiment described above. Once the optimum cross sectional area has been determined, device 21 is removed from the subject in a manner such as described with reference to FIGS. 23C-23E, and a permanent shunt of the indicated size is implanted.

Figure 23C:
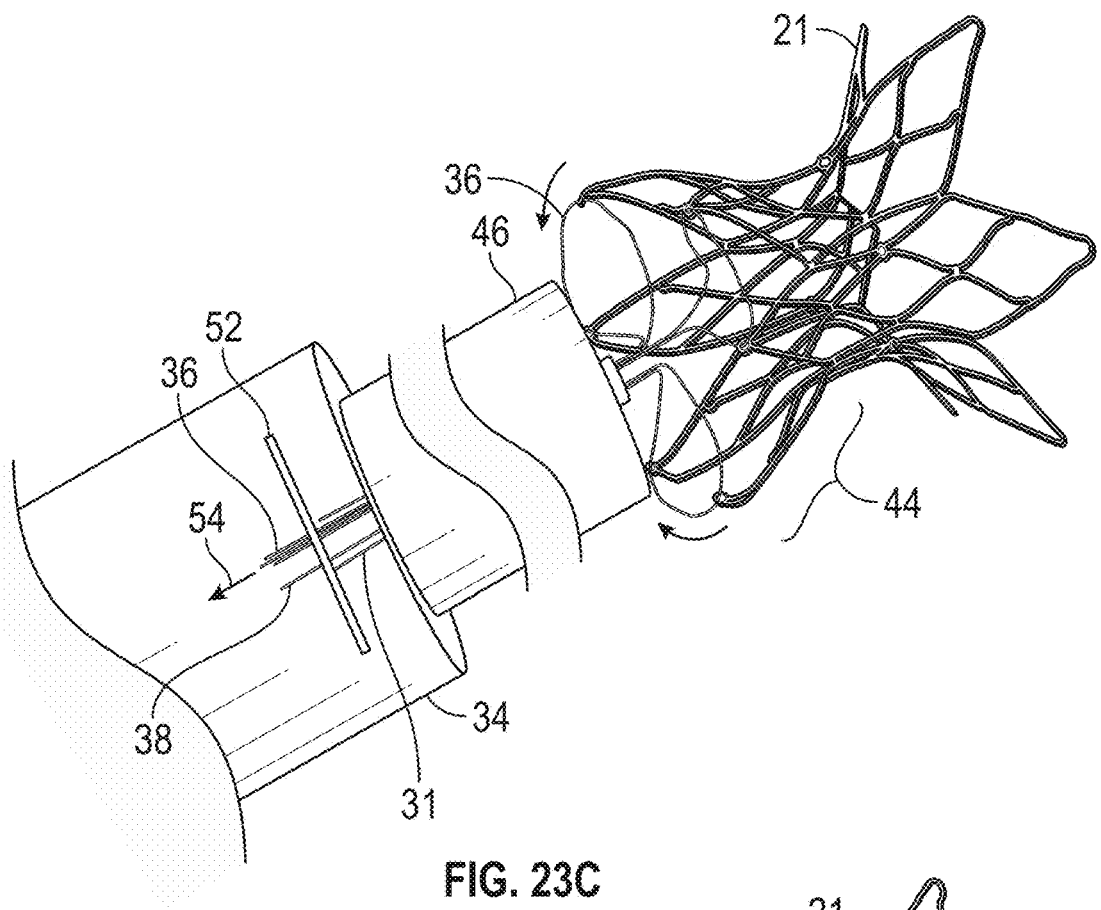
Figure 23D:
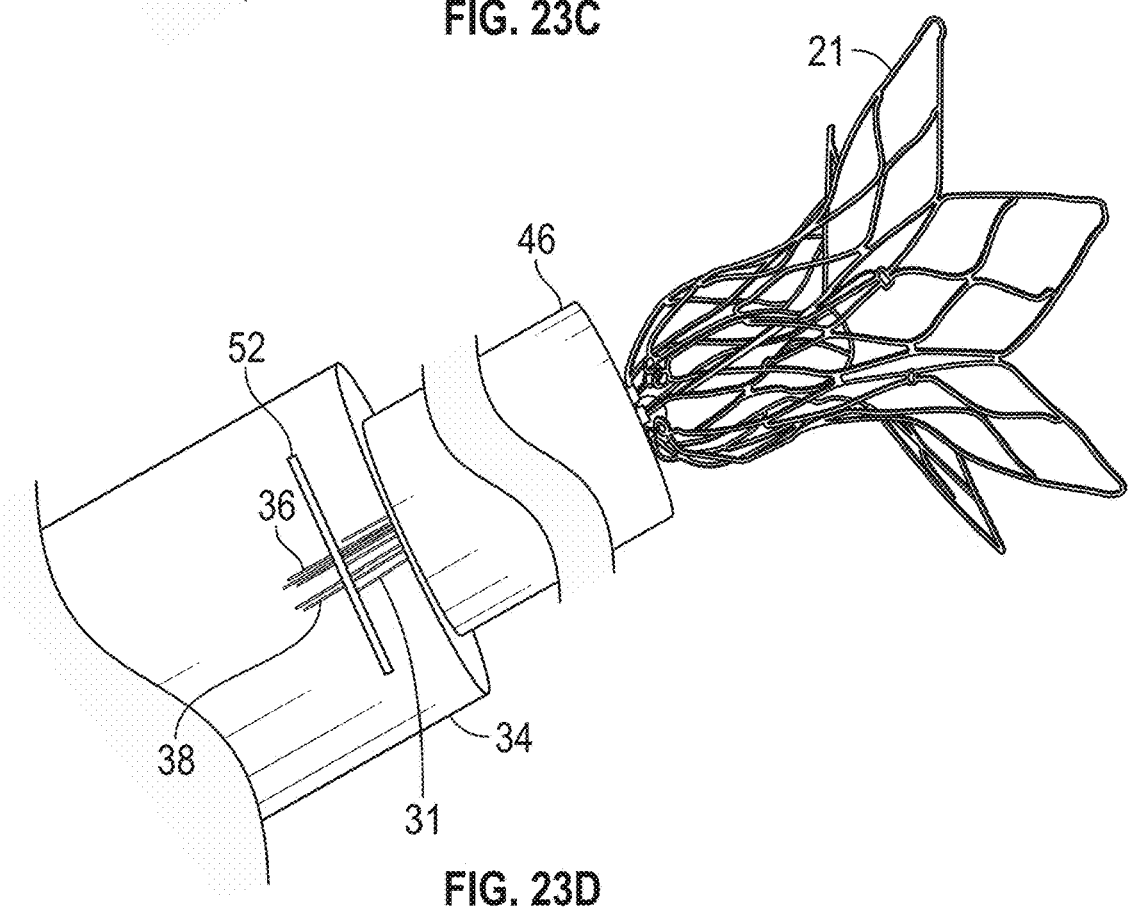
Figure 23E:
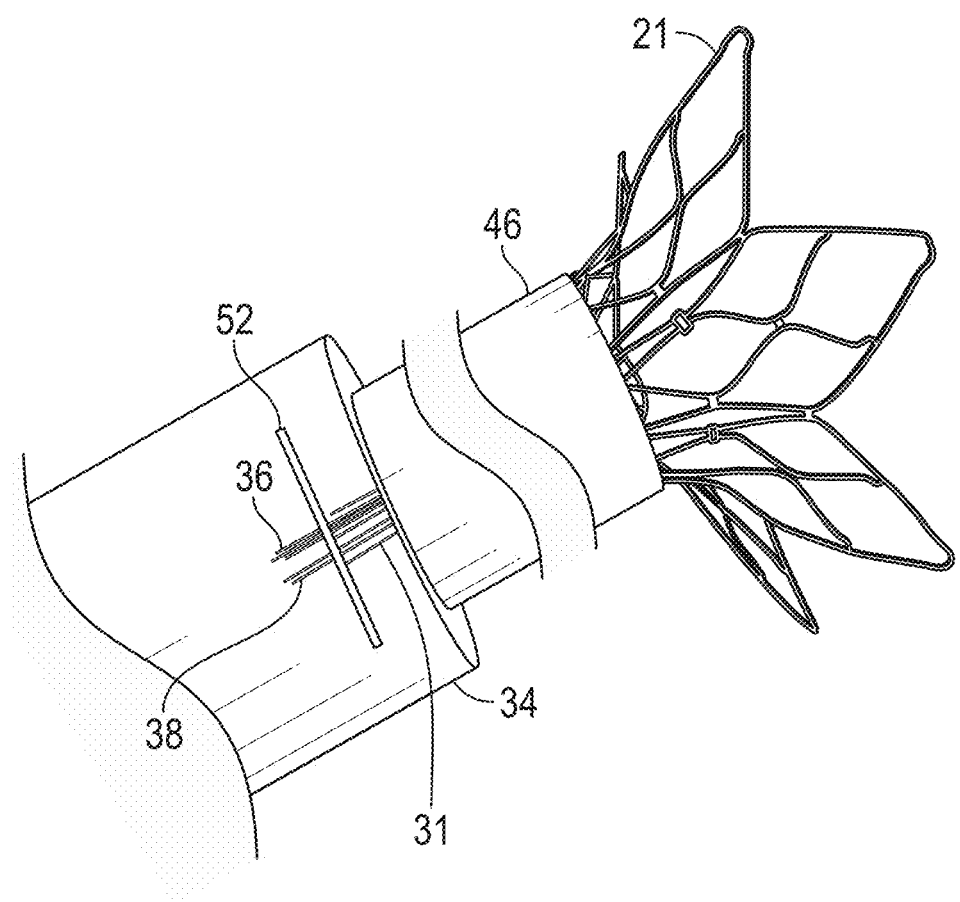
Figure 24A:
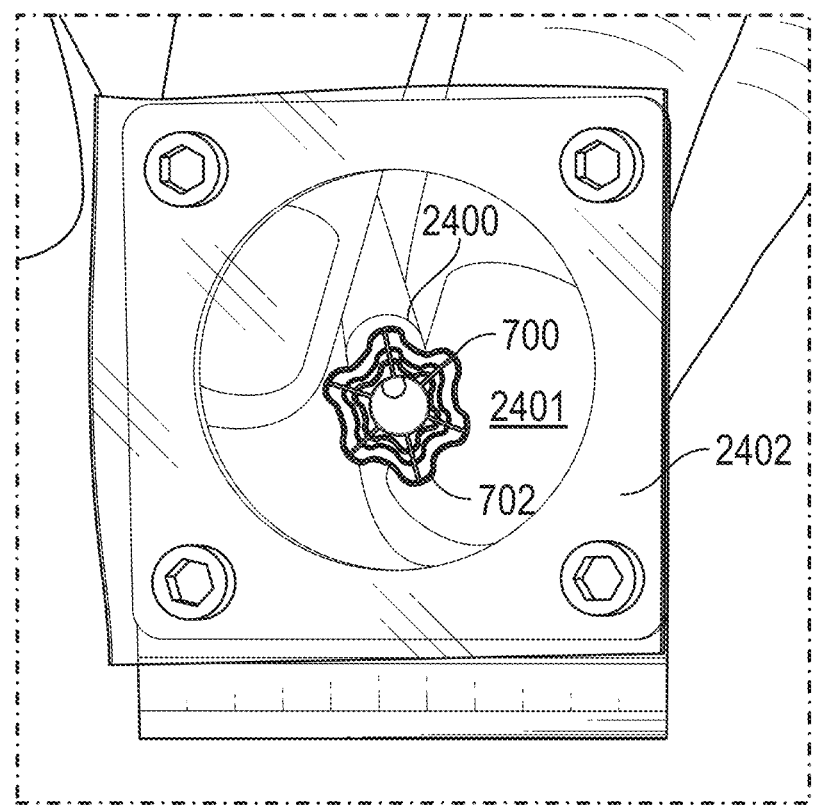
FIGS. 24A-24H are images of a device prepared and used in accordance with examples provided herein.
Figure 24B:
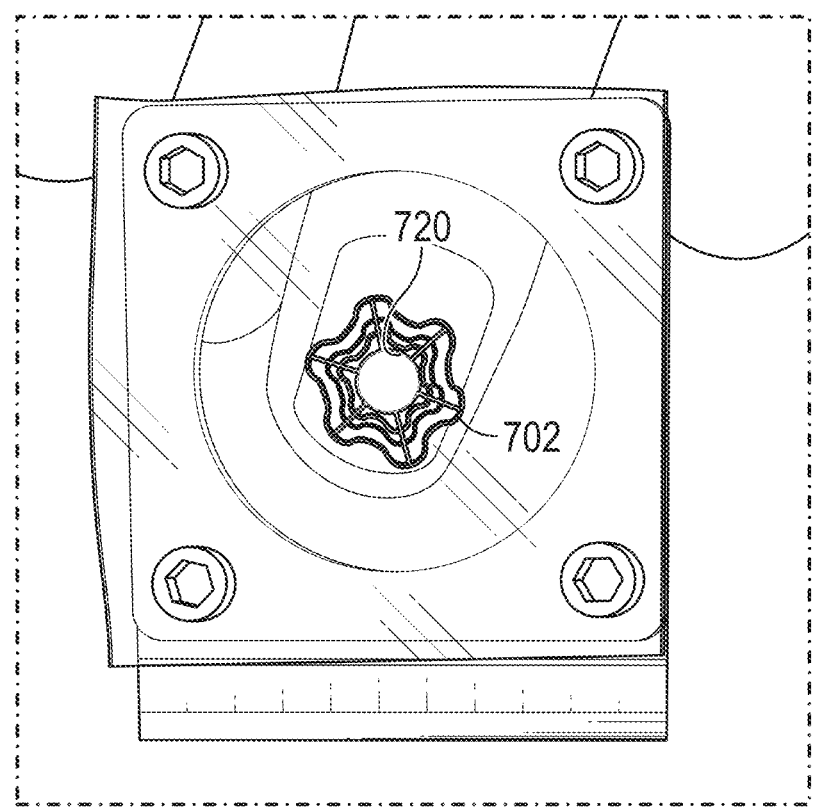
Figure 24C:
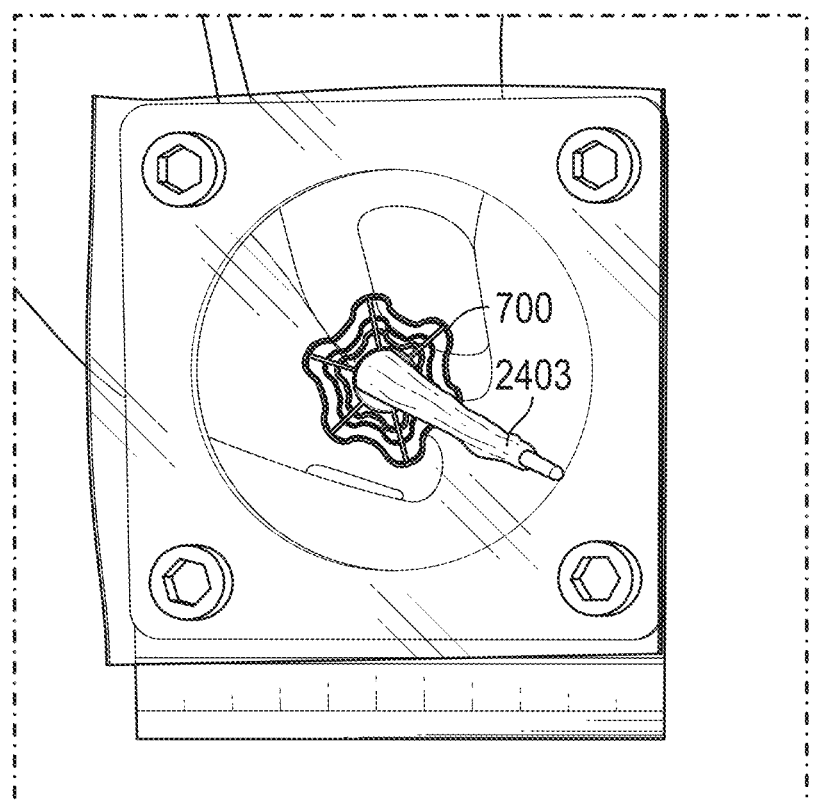
Figure 24D:
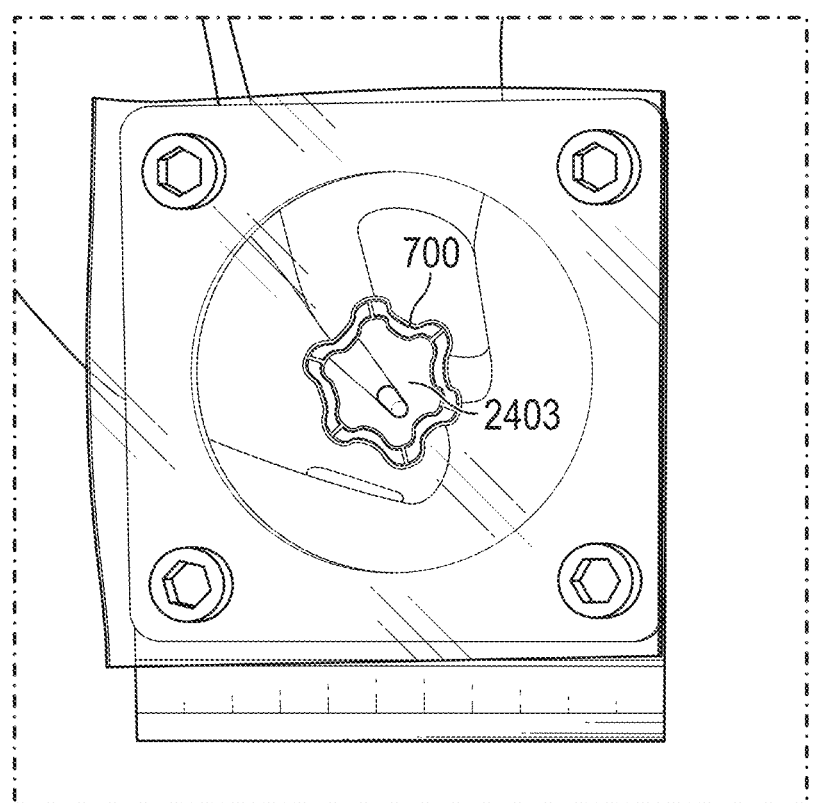
Figure 24E:
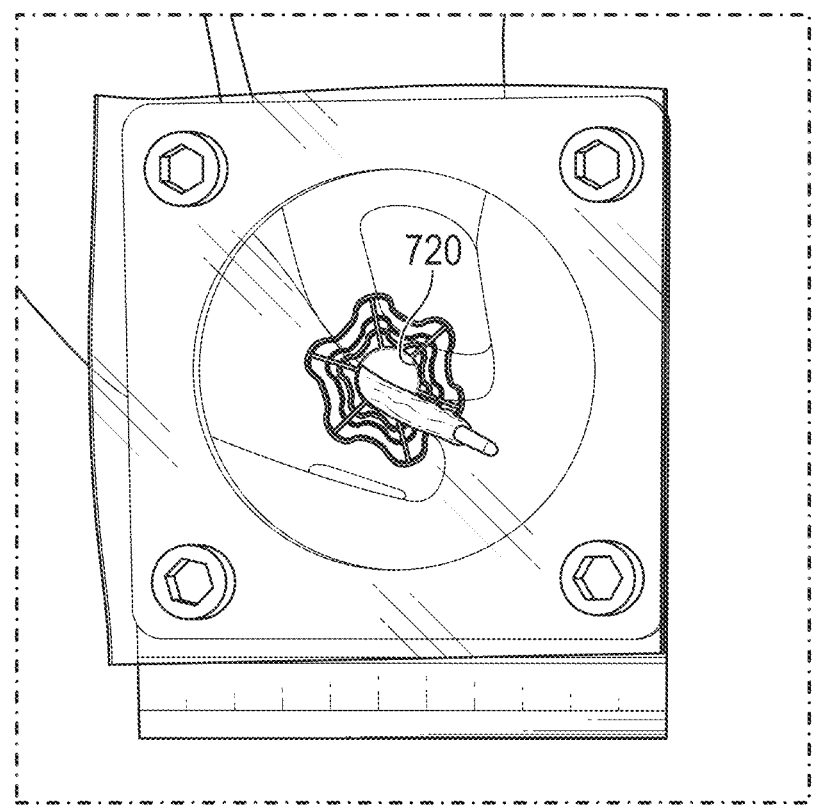
Figure 24F:
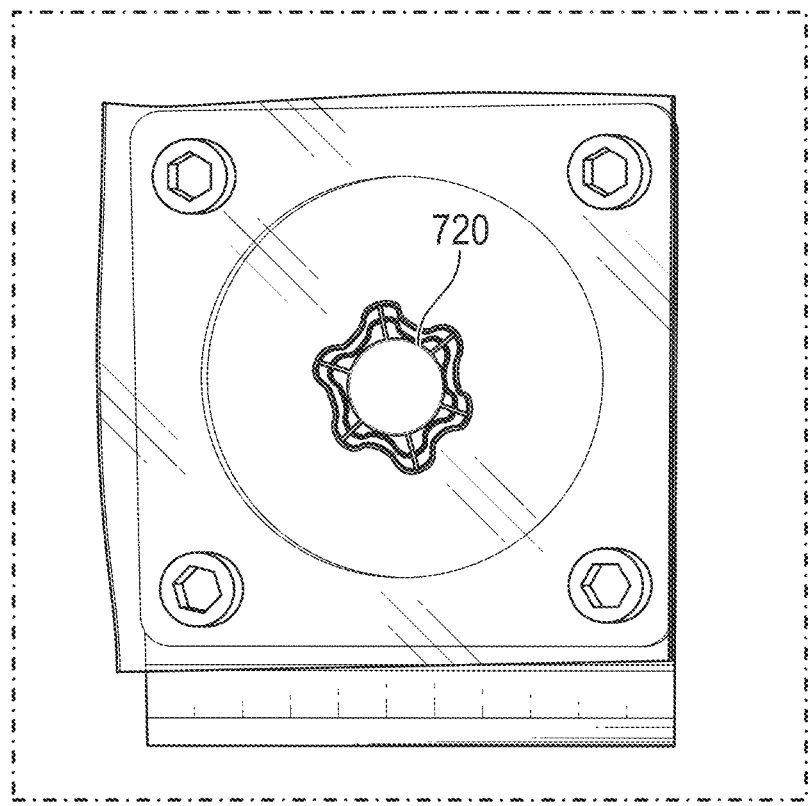
Figure 24G:
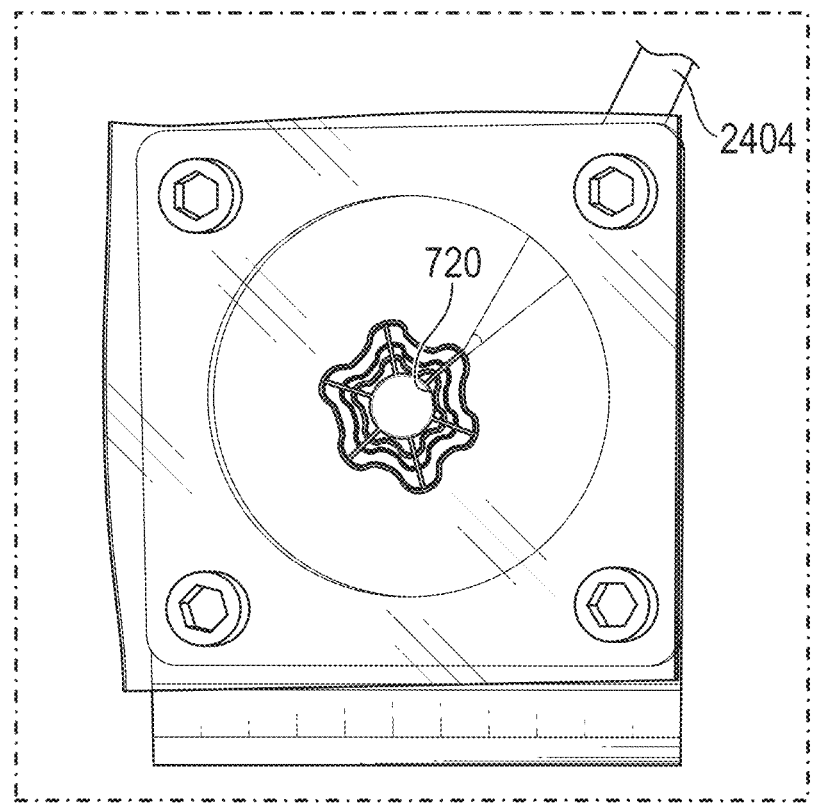
Figure 24H:
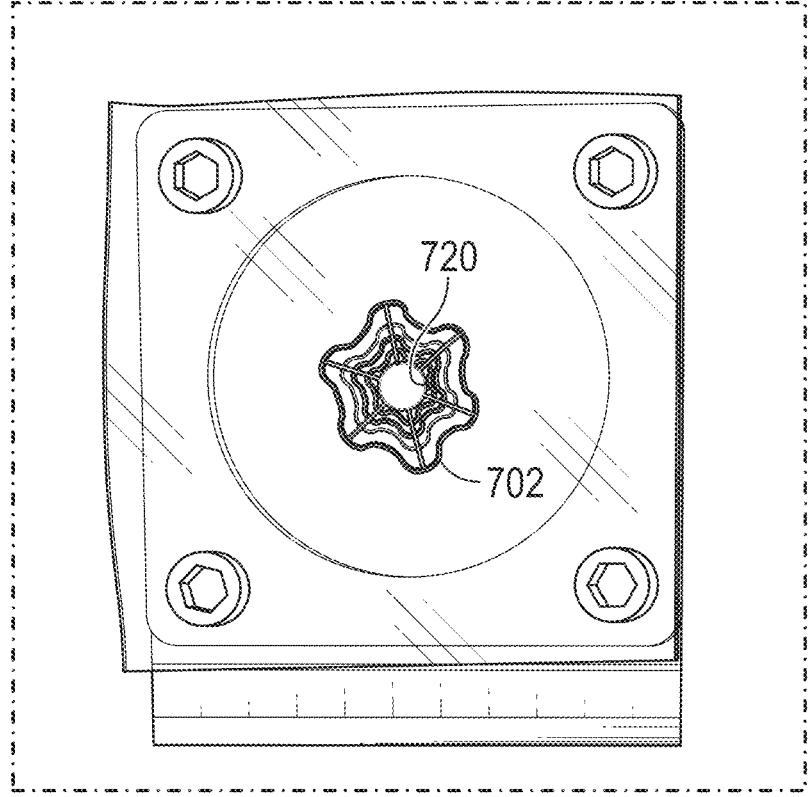

Reference is now made to FIGS. 23C-23E, which collectively show a technique for removing device 21 from subject 20, in accordance with some examples provided herein. It is noted that many of the details shown in FIGS. 23C-23E are provided by way of example only, and that many variations of the illustrated technique are included within the scope of the present disclosure.

In FIG. 23C, sheath 46 is advanced until the distal end of the sheath is close to proximal portion 44 of device 21. Subsequently, control wires 36 attached to device 21 are pulled, as indicated by the arrow 54 shown in FIG. 23C, such that an inward radial force is exerted on proximal portion 44. The inward radial force causes proximal portion 44 to at least partially collapse, as shown in FIG. 23D. Following the collapse of the proximal portion of device 21, as shown in FIG. 23E, sheath 46 is advanced distally over device 21 while catheter 31 is held in place, drawing the proximal portion of device 21 into the distal end of the sheath. (In passing over device 21, the sheath may at least partly pass through the interatrial septum.) As sheath 46 continues to pass over device 21 from the position shown in FIG. 23E, the catheter may be pulled proximally while holding the sheath in place, pulling device 21 further into the sheath until the sheath collapses distal portion 40 of device 21, such that device 21 becomes entirely collapsed within the sheath. Subsequently, the sheath, containing catheter 31 and device 21, may be removed from the subject.

In some examples, sheath 46 is advanced while proximal portion 44 is collapsing, such that, as proximal portion 44 continues to collapse, the catheter passes over device 21, until the distal end of the catheter crosses through the septum and reaches the distal portion of device 21. (In such examples, the state shown in FIG. 23D may not actually come to transpire, because sheath 46 covers the proximal portion of device 21 before the proximal portion 44 of device 21 is fully collapsed.) Then, as the pulling of device 21 by catheter 31 via wires 36 continues while sheath 46 is held in place or is pushed forward, the distal end of the catheter exerts a force on the distal portion 40 of device 21, such that the distal portion of device 21 collapses, and device 21 is drawn into the catheter. In such examples, due to the sheath being advanced over device 21 while wires 36 are pulled, device 21 may be relatively unlikely to be pulled into the right atrium before collapsing into the sheath.

FIGS. 23C-23E show a nonlimiting example in which catheter 31 extends to a stopper 52 contained inside of control handle 34, wires 36 passing through stopper 52. As the wires are pulled, stopper 52 inhibits or prevents catheter 31 from moving proximally, such that most of the pulling force acts on proximal portion 44, rather than on catheter 31. Although flexible, catheter 31 is resistant to buckling, such that the pulling force is effectively transferred to proximal portion 44. In some examples, two separate tubes run through a single lumen, or two separate lumens, of catheter 31, one of these tubes holding control wires 36, and the other of these tubes holding signal wires 38. In another embodiment, control wires 36 as well as the signal wires 38, when present, run through a separate individual lumens disposed in the wall of catheter 31, leaving an enlarged central multipurpose lumen 39, as shown in FIG. 23 A. Such tubes may provide additional resistance to buckling, such that the pulling force exerted on the wires is effectively transmitted to device 21. In such embodiments, stopper 52 may be used to inhibit or prevent the wire-holding tubes from moving proximally as the wires are pulled.

In some examples, proximal portion 44 may be provided in a malleable shape-memory phase at body temperature, heat set to a collapsed configuration similar to that shown in FIG. 23D, and deployed in a manner similar to that described with reference to FIGS. 23A-23B. However, instead of self-expanding, proximal portion 44 may be deployed by positioning an hourglass-shaped balloon through device 21, and inflating the balloon to expand the proximal portion. Such balloon expansion of proximal portion 44 may be performed after self-expansion of distal portion 40.

It is noted that the apparatus and methods such as described with reference to FIGS. 23A-23E may also be used for applications in which device 21 is to be permanently implanted. In such applications, during the implantation procedure, wires 36 may be used to facilitate the retrieval or repositioning of device 21, in the event that the device was not placed at the proper location. Subsequently, upon confirmation that device 21 is properly situated, wires 36 may be detached from device 21, and removed from the subject.

Accordingly, provided herein is an interatrial shunt for placement at an atrial septum of a patient's heart. The interatrial shunt may be configured similarly as one or more of device 200 described with reference to FIGS. 2A-2E; device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; and device 28 described with reference to FIGS. 23A-23E. For example, the interatrial shunt may include a body that includes first and second regions coupled in fluid communication by a neck region, e.g., such as included in device 200 described with reference to FIGS. 2A-2E; device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E. The body may include a shape-memory material, e.g., in a manner such as described elsewhere herein. The body may define a passageway through the neck region for blood to flow between a first atrium and a second atrium, e.g., in a manner such as device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E. The first and second regions may be superelastic at body temperature, and the neck region may be malleable at body temperature, e.g., in a manner such as described elsewhere herein. A flow area of the passageway through the neck region may be adjusted in vivo, e.g., in a manner such as described elsewhere herein.

The first and second regions that are superelastic may include NITINOL having an austenitic finish temperature (Af) between 5-20° C., e.g., in a manner such as described elsewhere herein. The neck region that is malleable may include NITINOL having an austenitic finish temperature (Af) between 45-60° C., e.g., in a manner such as described elsewhere herein. The neck region may be mechanically expandable, e.g., in a manner such as described elsewhere herein. The neck region may be thermally contractible, e.g., in a manner such as described elsewhere herein.

Also provided herein is an interatrial shunt for placement at an atrial septum of a patient's heart for adjustably regulating fluid flow therethrough. The interatrial shunt may be configured similarly as one or more of device 200 described with reference to FIGS. 2A-2E; device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; and device 28 described with reference to FIGS. 23A-23E. For example, the interatrial shunt may include a first expandable end region configured to be placed in a first atrium of the heart, and a second expandable end region configured to be placed in a second atrium of the heart, e.g., such as included in device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E. The first and second expandable end regions may include self-expanding superelastic material, e.g., in a manner such as described elsewhere herein. The interatrial shunt may include a neck region between the first and second expandable end regions, e.g., such as included in device 200 described with reference to FIGS. 2A-2E; device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E. The neck region may be configured for placement at the atrial septum, e.g., in a manner such as device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E. The neck region may include malleable shape-memory material, e.g., in a manner such as described elsewhere herein. The interatrial shunt may define a passageway through the neck region for blood to flow between the first atrium and the second atrium, e.g., in a manner such as device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E. The neck region may be heat treated to exhibit different shape memory properties than the first and second expandable end regions such that a cross-sectional area of the passageway is adjustable in vivo, e.g., in a manner such as described elsewhere herein, for example but not limited to a manner such as described with reference to FIGS. 10A-10C.

The malleable shape-memory material may be configured to be expanded in vivo such that the passageway expands from the cross-sectional area to a second cross-sectional area larger than the cross-sectional area, e.g., in a manner such as described elsewhere herein. The malleable shape-memory material may be configured to be contracted in vivo such that the passageway contracts from the second cross-sectional area to a third cross-sectional area smaller than the second cross-sectional area, e.g., in a manner such as described elsewhere herein. The cross-sectional area may be between 4.9 to 28.3 mm$^2$ and the second cross-sectional area and the third cross-sectional area may be between 15.9 to 78.6 mm$^2$. For example, for any of device 200 described with reference to FIGS. 2A-2E; device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E, the cross-sectional area may be between 4.9 to 28.3 mm$^2$ and the second cross-sectional area and the third cross-sectional area may be between 15.9 to 78.6 mm$^2$.

The malleable shape-memory material may include NITINOL having an austenitic finish temperature (Af) between 45-60° C., e.g., in a manner such as described elsewhere herein. The self-expanding superelastic material may include NITINOL having an austenitic finish temperature (Af) between 5-20° C., e.g., in a manner such as described elsewhere herein. The malleable shape-memory material may be mechanically expandable, e.g., in a manner such as described elsewhere herein. The malleable shape-memory material may be thermally contractible, e.g., in a manner such as described elsewhere herein. The cross-sectional area of the neck region may be smaller than respective cross-sectional areas of at least one of the first and second expandable end regions, e.g., in a manner such as described for device 200 described with reference to FIGS. 2A-2E; device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E. The first and second expandable end regions may extend into the first and second atria, respectively, such that respective ends of the first and second expandable end regions may not contact the atrial septum, e.g., in a manner such as device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E.

The first and second expandable end regions and the neck region may comprise a diabolo-shaped shunt, e.g., in a manner such as device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E. The neck region may include a cylindrical shunt, e.g., in a manner such as device 1110 described with reference to FIGS. 11A-11B; device 1210 described with reference to FIGS. 12A-12B; or device 1300 described with reference to FIGS. 13A-13B. The cylindrical shunt may be outside of the diabolo-shaped shunt, e.g., in a manner such as device 1110 described with reference to FIGS. 11A-11B. The cylindrical shunt may be formed of the malleable shape-memory material such that the cylindrical shunt radially constrains a dimension of the diabolo-shaped shunt at the neck region, and the diabolo-shaped shunt may self-expand at the neck region responsive to the malleable shape memory material expanding to a second cross-sectional area, e.g., in a manner such as device 1110 described with reference to FIGS. 11A-11B. The cylindrical shunt may be inside of the diabolo-shaped shunt, e.g., in a manner such as device 1210 described with reference to FIGS. 12A-12B, or device 1300 described with reference to FIGS. 13A-13B. The cylindrical shunt may not be directly coupled to the diabolo-shaped shunt and the neck region, e.g., in a manner such as device 1210 described with reference to FIGS. 12A-12B, or device 1300 described with reference to FIGS. 13A-13B. The device may further include an encapsulant indirectly and elastically coupling the cylindrical shunt to the diabolo-shaped shunt, e.g., in a manner such as device 1210 described with reference to FIGS. 12A-12B. Contraction of the cylindrical shunt may not cause contraction of the diabolo-shaped shunt at the neck region, e.g., in a manner such as device 1210 described with reference to FIGS. 12A-12B, or device 1300 described with reference to FIGS. 13A-13B. The diabolo-shaped shunt and the cylindrical shunt may be integrally formed from a common frame, e.g., in a manner such as described elsewhere herein. The first and second expandable end regions and the neck region may be integrally formed from a common frame, e.g., in a manner such as described elsewhere herein. The first and second expandable end regions and the neck region may be at least partially encapsulated with a biocompatible material, e.g., in a manner such as described elsewhere herein.

Also provided herein is an interatrial shunt for adjustably regulating fluid flow in a heart having a first atrium, a second atrium, and an atrial septum. The interatrial shunt may be configured similarly as one or more of device 200 described with reference to FIGS. 2A-2E; device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; and device 28 described with reference to FIGS. 23A-23E. For example, the interatrial shunt may include a first region that includes a self-expanding superelastic material configured to be placed in the first atrium, e.g., such as included in device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E. The first region may be superelastic at body temperature, e.g., in a manner such as described elsewhere herein. The interatrial shunt may include a second region that includes a malleable shape-memory material configured to be placed through an opening in the atrial septum so as to provide fluid flow from the first atrium to the second atrium, e.g., such as included in device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E. The second region may be malleable at body temperature, e.g., in a manner such as described elsewhere herein. The malleable shape-memory material may have a first cross-sectional area, e.g., in a manner such as described elsewhere herein. The malleable shape-memory material may be expandable from the first cross-sectional area to a second cross-sectional area, e.g., in a manner such as described elsewhere herein. The malleable shape-memory material may be contractible from the second cross-sectional area to a third cross-sectional area, e.g., in a manner such as described elsewhere herein.

The self-expanding superelastic material may include NITINOL having an austenitic finish temperature (Af) between 5-20° C., and the malleable shape-memory material may include NITINOL having an austenitic finish temperature (Af) between 45-60° C., e.g., in a manner such as described elsewhere herein. The malleable shape-memory material may be mechanically expandable and thermally contractible, e.g., in a manner such as described elsewhere herein. The interatrial shunt may include a third region that includes a second self-expanding superelastic material, is configured to be placed in the second atrium, and is coupled to the second region, e.g., such as included in device 700 described with reference to FIGS. 7, 8A-8D, 9A-9B, and 10A-10C; device 1110 described with reference to FIGS. 11A-11B; device 1210 described with reference to FIGS. 12A-12B; device 1300 described with reference to FIGS. 13A-13B; or device 28 described with reference to FIGS. 23A-23E.

Working Example

The following example is intended to be purely illustrative, and not limiting of the present invention.

FIGS. 24A-24H are sequential images of a device prepared and used in accordance with examples provided herein. More specifically, the diabolo-shaped shunt frame device 700 described with reference to FIG. 7 was formed from NITINOL with an initial austenitic finish temperature below 20° C., so that it would be in austenitic superelastic phase at body temperature of 37° C. The superelastic device 700 was heat-set to the shape shown in FIG. 7, within a jig that formed a neck diameter of 4 mm. Subsequently, the shunt was changed from a purely self-expanding, superelastic austenitic phase to a configuration where at least some elements of the frame exhibited malleable shape-memory martensitic phase physical properties, with all dimensions, including the neck diameter, remaining the same, by reheating the device to above 500° C. in an oven for a suitable duration. At the time of FIG. 24A, within a tank of 37° C. water, a transparent membrane 2401 is suspended in tooling 2402 to simulate an atrial septum, and shunt frame device 700 is deployed from behind the opening in membrane 2401 via sheath 2400 in a manner such as described elsewhere herein. It should be noted that the distal flange 702 (toward the viewer) has self-expanded from its crimped configuration in the delivery sheath 2400, indicating that this component is at least in part in an austenitic superelastic phase at the 37° C. temperature of the water bath, in accordance with the example set forth in FIG. 8A. At the time of FIG. 24B, following deployment across the transparent membrane, the neck 720 of device 700 has an initial cross-sectional area corresponding to its heat set minimum diameter of approximately 4 mm. At the time of FIG. 24C, commercially available angioplasty balloon 2403 is inserted through the neck of device 700. At the time of FIG. 24D, balloon 2403 is inflated to a diameter of approximately 7 mm at a pressure and for a duration sufficient to deform the neck of device 700. At the time of FIG. 24E, the balloon 2403 is deflated. At the time of FIG. 24F, it may be seen that neck 720 of device 700 remains at a diameter of approximately 7 mm after balloon 2403 is withdrawn, in accordance with the example set forth in FIG. 8B. At the time of FIG. 24G, neck 720 is bathed in heated saline via rapid injection through a catheter 2404, in accordance with the example set forth in FIG. 8C. At the time of FIG. 24H, after the heating shown in FIG. 24G, neck 720 has been returned to its approximately 4 mm heat set diameter, in accordance with the example set forth in FIG. 8D, demonstrating that the neck region 720 of device 700 exhibits the desired martensitic shape-memory properties. Operations such as described with reference to FIGS. 24C-24G may be repeated any suitable number of times so as to increase and reduce the dimensions of neck 720 as desired, while first and third portions 710, 730 securely retain device 700 in the opening through membrane 2401 simulating the atrial septum. Similar operations may be performed on other devices provided herein, e.g., so as to adjust the flow rate of such devices or to permit repositioning of the devices. Accordingly, it may be understood that one or more dimensions of the present devices suitably may be increased and decreased in vivo.

While various illustrative embodiments of the invention are described above, it will be apparent to one skilled in the art that various changes and modifications may be made therein without departing from the invention. For example, although examples of the present devices are described as having two or three components, it should be understood that the present devices may include any suitable number of components that respectively include a self-expanding superelastic material or a malleable shape-memory material. The appended claims are intended to cover all such changes and modifications that fall within the true spirit and scope of the invention.

What is claimed is:

1. A shunt for implantation within an atrial septum to treat a heart condition, the shunt comprising:
    a single, metallic frame comprising a first end region, a second end region, and a middle region disposed therebetween, the first and second end regions each configured to self-expand upon deployment such that the middle region is positioned in an opening in the atrial septum, the single, metallic frame being heat treated such that the middle region is expandable and/or contractible in vivo; and
    a biocompatible material coating the first end region, the second end region, and the middle region to define a passageway to permit blood to flow through the atrial septum via the shunt,
    wherein a cross-sectional flow area in the passageway is smallest at the middle region, and
    wherein the middle region is heat treated to exhibit different shape memory properties than the first and second end regions.

2. The shunt of claim 1, wherein the middle region comprises a plastically deformable material.

3. The shunt of claim 1, wherein the middle region is configured to be contracted in vivo via mechanical contraction.

4. The shunt of claim 1, wherein the middle region is configured to be contracted in vivo via thermal contraction.

5. The shunt of claim 1, wherein the middle region is configured to expanded in vivo via mechanical expansion.

6. A shunt for implantation within an atrial septum to treat a heart condition, the shunt comprising:
    a single, metallic frame comprising a first end region, a second end region, and a middle region disposed therebetween, the first and second end regions each configured to self-expand upon deployment such that the middle region is positioned in an opening in the atrial septum, the single, metallic frame being heat treated such that the middle region is expandable and/or contractible in vivo;

a biocompatible material coating the first end region, the second end region, and the middle region to define a passageway to permit blood to flow through the atrial septum via the shunt; and one or more sensors configured to measure pressure or blood flow through the passageway or both, wherein a cross-sectional flow area in the passageway is smallest at the middle region.

7. The shunt of claim 1, wherein the middle region is expandable in vivo such that a clinical procedure tool may pass through the passageway.

8. The shunt of claim 1, wherein the middle region is contractible in vivo after removal of a clinical procedure tool from the passageway.

9. The shunt of claim 1, wherein the middle region is malleable at body temperature and comprises NITINOL having an austenitic finish temperature between 45-60° C.

10. The shunt of claim 9, wherein the middle region is mechanically expandable and thermally contractible.

11. The shunt of claim 1, wherein the first end region and the second end region are superelastic and comprise NITINOL having an austenitic finish temperature between 5-20° C.

12. The shunt of claim 1, wherein the first and second end regions comprise self-expanding superelastic material and the middle region comprises malleable shape-memory material.

13. A shunt for implantation within an atrial septum to treat a heart condition, the shunt comprising:

a single, metallic frame comprising a first end region, a second end region, and a middle region disposed therebetween, the first and second end regions each configured to self-expand upon deployment such that the middle region is positioned in an opening in the atrial septum, the single, metallic frame being heat treated such that the middle region is expandable and/or contractible in vivo; and a biocompatible material coating the first end region, the second end region, and the middle region to define a passageway to permit blood to flow through the atrial septum via the shunt, wherein a cross-sectional flow area in the passageway is smallest at the middle region, wherein the first and second end regions comprise self-expanding superelastic material and the middle region comprises malleable shape-memory material, and wherein the malleable shape-memory material comprises NITINOL having an austenitic finish temperature (Af) between 45-60° C.

14. The shunt of claim 11, wherein the self-expanding superelastic material comprises NITINOL having an austenitic finish temperature (Af) between 5-20° C.

15. The shunt of claim 1, wherein the first and second end regions are superelastic at body temperature and the middle region is malleable at body temperature.

16. The shunt of claim 13, wherein the middle region is heat treated to exhibit different shape memory properties than the first and second end regions.

17. The shunt of claim 1, wherein the first and second end regions and the middle region comprise a diabolo-shaped shunt.

18. The shunt of claim 17, wherein the middle region comprises a cylindrical shunt.

19. The shunt of claim 18, wherein the cylindrical shunt is outside of the diabolo-shaped shunt.

20. The shunt of claim 1, wherein an inner diameter of the passageway at the middle region is 4-7 mm.

21. The shunt of claim 1, wherein the passageway is sized and shaped to permit a sufficient amount of blood to flow through the atrial septum via the shunt to treat pulmonary artery hypertension (PAH).

22. The shunt of claim 1, wherein the passageway is sized and shaped to permit a sufficient amount of blood to flow through the atrial septum via the shunt to treat heart failure (HF).

23. A method for treating a heart condition, the method comprising:

delivering a shunt to an opening in the atrial septum in a contracted state, the shunt comprising a frame having first and second end regions and a middle region disposed therebetween, the frame heat treated to be adjustable in vivo, the shunt further comprising a biocompatible material coating the first and second end regions and the middle region to define a passageway; and deploying the shunt within the opening such that the shunt transitions to an expanded state wherein the first end region self-expands and is disposed in a first atrium, the second end region self-expands and is disposed in a second atrium, and the middle region is disposed at the atrial septum to permit blood to flow through the atrial septum via the passageway, wherein a cross-sectional flow area in the passageway is smallest at the middle region and the middle region is adjustable in vivo from a first diameter to a second diameter different than the first diameter, wherein the middle region is heat treated to exhibit different shape memory properties than the first and second end regions.

24. The method of claim 23, wherein the first end region, the second end region, and the middle region of the frame are formed from a single metallic frame.

25. The method of claim 23, wherein the middle region comprises a plastically deformable material.

26. The method of claim 23, further comprising expanding the middle region in vivo via mechanical expansion.

27. The method of claim 23, further comprising contracting the middle region in vivo via thermal contraction.

28. The method of claim 23, further comprising permitting a sufficient amount of blood to flow through the atrial septum via the passageway of the shunt to treat pulmonary artery hypertension (PAH).

29. The method of claim 23, further comprising permitting a sufficient amount of blood to flow through the atrial septum via the passageway of the shunt to treat heart failure (HF).

* * * * *

UNITED STATES PATENT AND TRADEMARK OFFICE
CERTIFICATE OF CORRECTION

| | |
|---|---|
| PATENT NO. | : 11,458,287 B2 |
| APPLICATION NO. | : 17/660384 |
| DATED | : October 4, 2022 |
| INVENTOR(S) | : Nir Nae et al. |

It is certified that error appears in the above-identified patent and that said Letters Patent is hereby corrected as shown below:

On the Title Page

Item (12) delete "Eigler et al." and insert --Nae et al.--

Item (72) please correct the order of the inventors as follows:
(72) Inventors: Nir Nae, Binyamina, (IL); Neal Eigler, Agoura Hills, CA (US); Nathan Bukhdruker, Haifa (IL); James S. Whiting, Los Angeles, CA (US); Lior Rosen, Or Akiva (IL); Erez Rozenfeld, Shoham (IL); Werner Hafelfinger, Thousand Oaks, CA (US); Tamir Ben-David, Tel Aviv (IL)

Signed and Sealed this
Twenty-seventh Day of August, 2024

Katherine Kelly Vidal
*Director of the United States Patent and Trademark Office*